(12) United States Patent
Wu et al.

(10) Patent No.: US 8,648,173 B2
(45) Date of Patent: Feb. 11, 2014

(54) INHIBITION OF TUMOR METASTASIS BY ANTI NEUROPILIN 2 ANTIBODIES

(75) Inventors: Yan Wu, Foster City, CA (US); Wei-Ching Liang, Foster City, CA (US); Ryan Jefferson Watts, San Mateo, CA (US); Anil Durgadas Bagri, San Carlos, CA (US)

(73) Assignee: Genentech, Inc., South San Francsico, CA (US)

( * ) Notice: Subject to any disclaimer, the term of this patent is extended or adjusted under 35 U.S.C. 154(b) by 432 days.

(21) Appl. No.: 12/598,537

(22) PCT Filed: May 17, 2007

(86) PCT No.: PCT/US2007/069179
§ 371 (c)(1),
(2), (4) Date: Mar. 19, 2010

(87) PCT Pub. No.: WO2008/143665
PCT Pub. Date: Nov. 27, 2008

(65) Prior Publication Data
US 2010/0172921 A1 Jul. 8, 2010

(51) Int. Cl.
*C07K 16/00* (2006.01)
(52) U.S. Cl.
USPC .................. 530/387.3; 530/387.7; 424/133.1
(58) Field of Classification Search
None
See application file for complete search history.

(56) References Cited

U.S. PATENT DOCUMENTS 7,994,286 B2 * 8/2011 Watts et al. ................ 530/387.1

FOREIGN PATENT DOCUMENTS

| EP | 0 817648 B1 | 1/1998 |
| WO | WO 98/45331 A2 | 10/1998 |
| WO | WO 98/45332 A2 | 10/1998 |
| WO | 99/29729 * | 6/1999 |

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Brown et al (J. Immunol. May 1996; 156(9):3285-3291.*
Vajdos et al (J. Mol. Biol., Jul. 5, 2002;320(2); 415-428.*
Essell (J. NIH Res. 1995 7:46.*
Spitler (Cancer Biotherapy, 1995, 10:1-3).*
Boon (Adv. Can. Res. 1992 58:177-210).*
Achen et al., *Br J Cancer* 94 (2006), 1355-1360.
Adamis et al., *Arch. Ophthalmol.* 114:66-71 (1996).
Bielenberg et al., *J Clin Invest* 114, 1260-1271 (2004).
Borgstrom et al., *Cancer Res.* 56:4032-4039 (1996).
Chen et al., *Cancer Res* 65, 9004-9011 (2005).
Favier et al., *Blood* 108, 1243-1250 (2006).
Ferrara et al., *Nat Med* 9, 669-676 (2003).
Folkman et al.. *J. Biol. Chem.*, 267:10931-10934 (1992).
Folkman et al., *Nature* 339:58 (1989).
Folkman *Nat Med* 1(1):27-31 (1995).
Garner A., "Vascular diseases", In: Pathobiology of Ocular Disease. A Dynamic Approach, Garner A., Klintworth GK, eds., 2nd Edition (Marcel Dekker, NY, 1994), pp. 1625-1710.
He et al., *J. Natl Cancer Inst*, vol. 94, No. 11, pp. 819-825, (2002).
Heldin, "Dimerzation of cell surface receptors in signal transduction", *Cell* vol. 80, pp. 213-223, (1995).
Karpanen et al.. *Faseb Journal*, 20, pp. 1462-1472, (2001).
Kim et al. *Nature* vol. 362, pp. 841-844 (1993).
Klagsbrun et al., *Annu. Rev. Physiol*, 53:217-239 (1991).
Krishnan et al., *Cancer Res* 63, 713-722 (2003).
Liang et al., *J11401 Biol* 366, 815-829 (2007).
Liang et al., *JBiol Chem* 281, 951-961 (2006).
Macchiarini et al., *Lancet* 340:145-146 (1992).
Mandriota et al., *EMBO J* 20, 672-682 (2001).
Massague, *Cell* 127, 679-695 (2006).
Melnyk et al., *Cancer Res.* 56:921-924 (1996).
Murga et al., *Blood* 105, 1992-1999 (2005).
Nathanson, *Cancer* 98,413-423 (2003).
Pan et al., *Cancer Cell* 11, 53-67 (2007).
Shinkai et al., *J Biol Chem* 273, 31283-31288 (1998).
Skobe et al., *Nat Med* 7, 192-198 (2001).
Soker et al., *J Cell Biochem* 85, 357-368 (2002).
Stacker et al., *Faseb J* 16, 922-934 (2002).
Stacker et al., *Nat Rev Cancer* 2, 573-583 (2002).
Takashima et al., *Proc Natl Acad Sci USA* 99, 3657-3662 (2002).
Waltenberger et al., J. *Biol Chem* 269, 26988-26995 (1994)).
Wang et al., *JBiol Chem* 278, 48848-48860 (2003).
Warren et al., *J. Clin. Invest*. 95:1789-1797 (1995.
Weidner et al., *N. Engl Med* 324:1-6 (1991).
Yuan et al.. *Development* 129, 4797-4806 (2002).

* cited by examiner

*Primary Examiner* — Sheela J Huff
(74) *Attorney, Agent, or Firm* — Janet Martineau; Alissa H. Faris; Arnold & Porter LLP

(57) ABSTRACT

The application provides Nrp2 antagonists, such as anti-Nrp2 antibodies, and their use in the prevention and treatment of tumor metastasis.

20 Claims, 31 Drawing Sheets

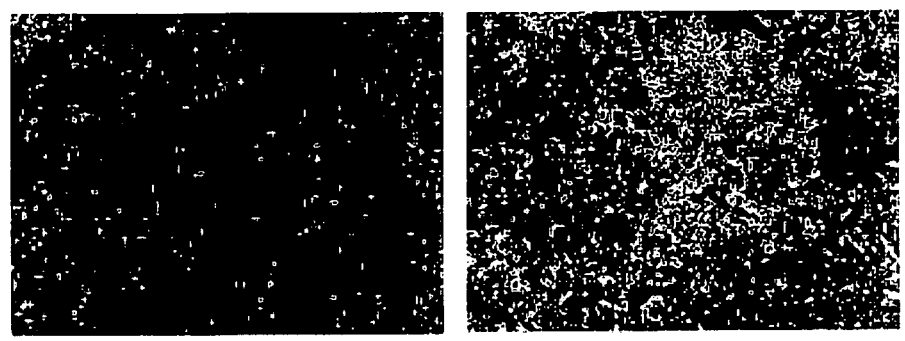
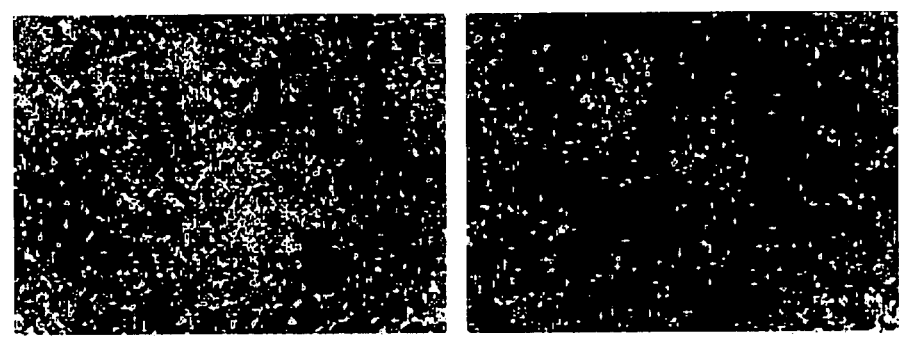
Figure 2A

Neuropilin-2 / Prox-1
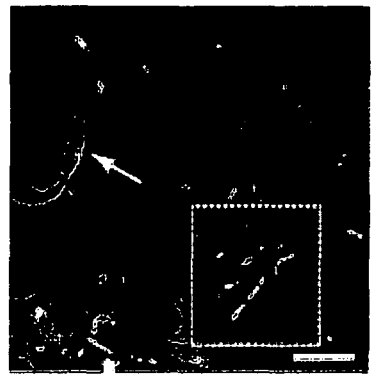 
E12.5 Embryo
Figure 4A

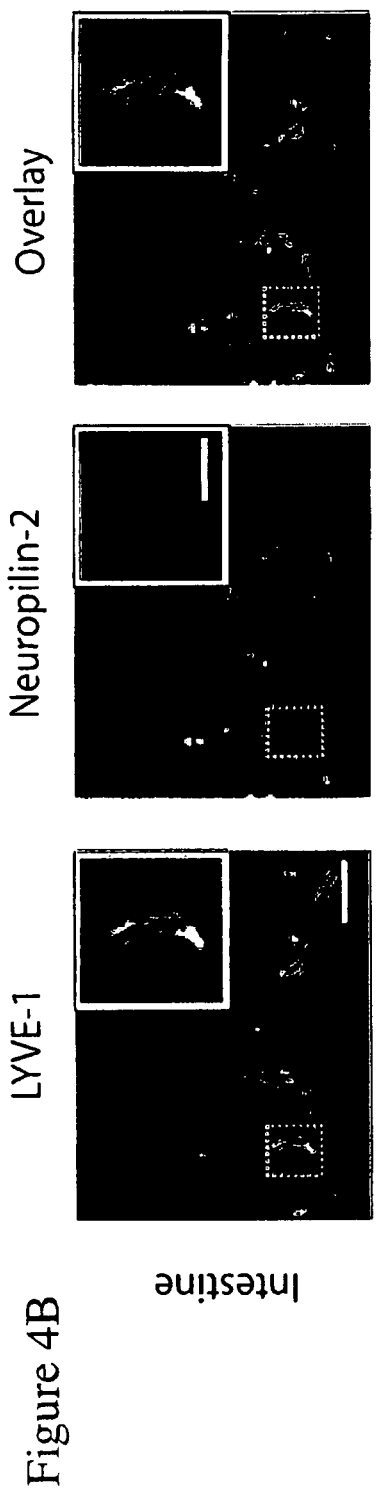
Figure 4B Intestine
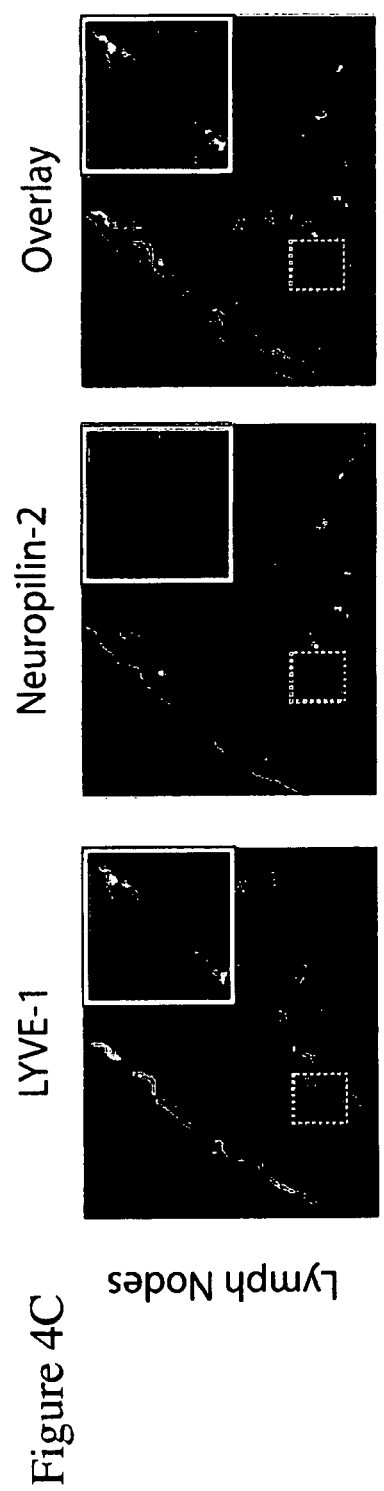
Figure 4C Lymph Nodes

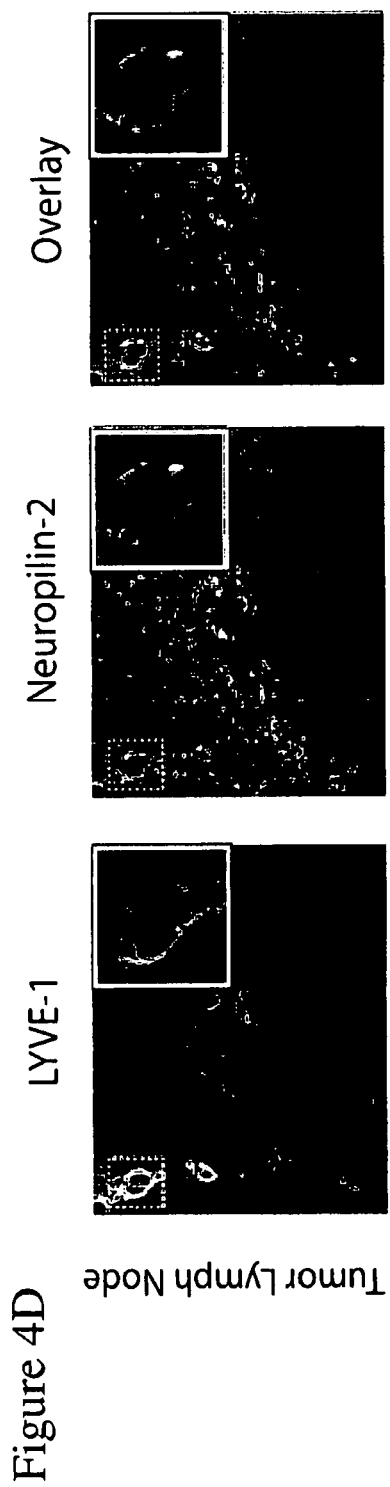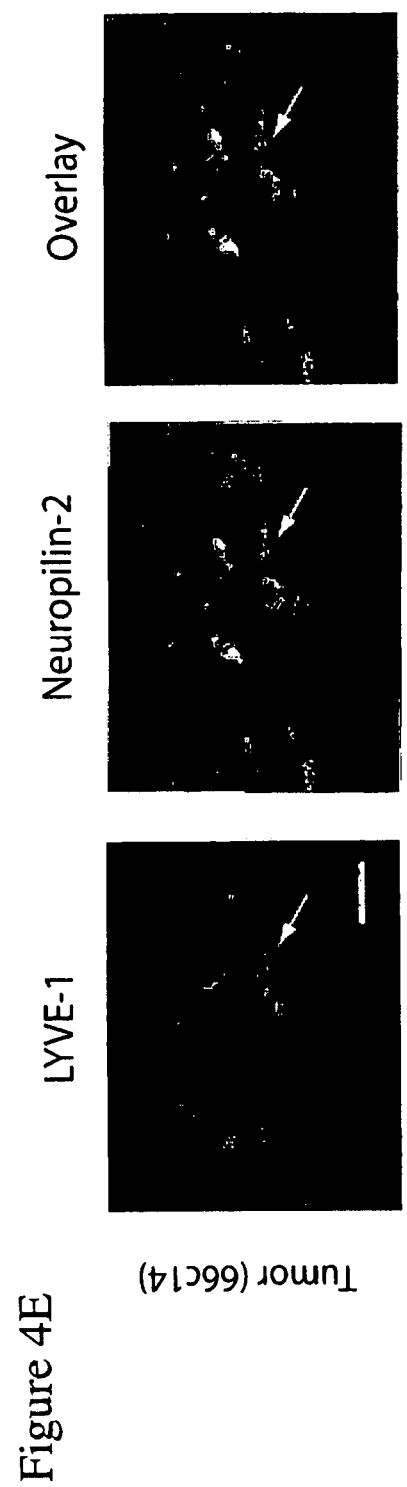
Figure 4D
Figure 4E

C6 tumor cell FACS analysis

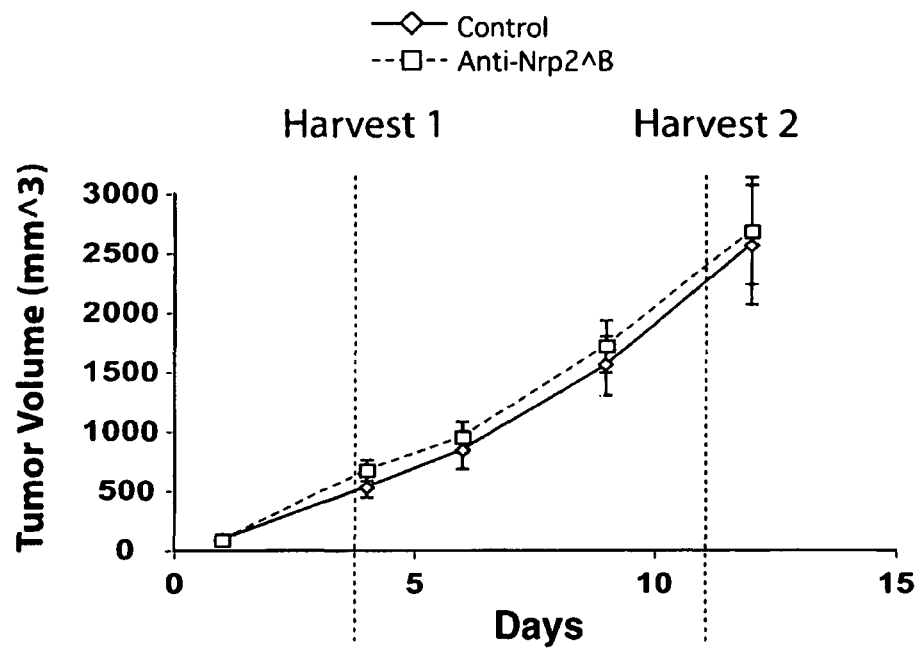
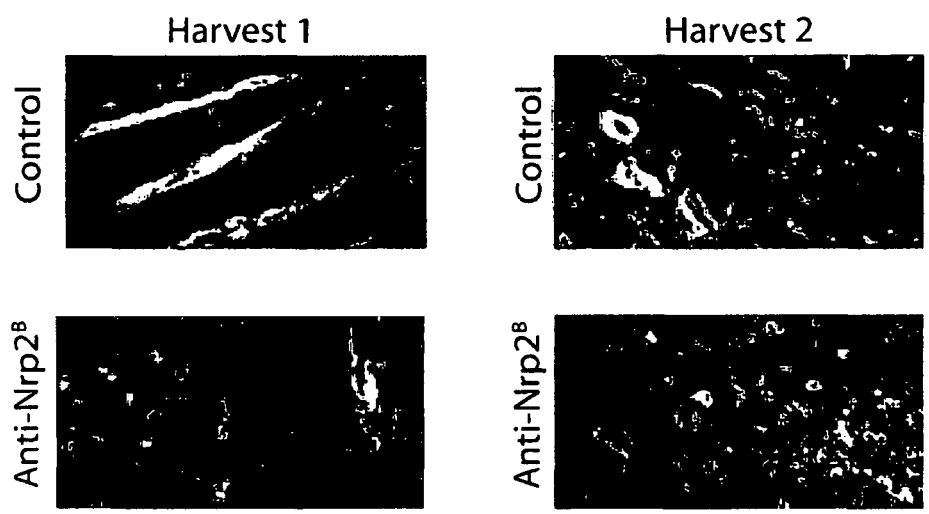
Figure 7D

Anti-NRP2B YW68.4.2 hIgG1 P1 file

DIQMTQSPSSLSASVGDRVTITCRASQDVSTAVAWYQQKPGKAPKLLIYSA
SFLYSGVPSRFSGSGSGTDFTLTISSLQPEDFATYYCQQSYTTPPTFGQGTK
VEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPV
TKSFNRGECEVQLVESGGGLVQPGGSLRLSCAASGFTITSSGIHWVRQAPG
KGLEWVARITPYDGSTDYADSVKGRFTISADTSKNTAYLQMNSLRAEDTA
VYYCARYRGTLLFDYWGQGTLVTVSSASTKGPSVFPLAPSSKSTSGGTAA
LGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSL
SPGK

Figure 10A

Anti-NRP2B YW68.4.2.36 hIgG1 P1 file

DIQMTQSPSSLSASVGDRVTITCRASQDVSTAVAWYQQKPGKAPKLLIYSA
SFLYSGVPSRFSGSGSGTDFTLTISSLQPEDFATYYCQQHYTTPPTFGQGTK
VEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPV
TKSFNRGECEVQLVESGGGLVQPGGSLRLSCAASGFTITSSGIHWVRQAPG
KGLEWVARITPYDGSTDYADSVKGRFTISADTSKNTAYLQMNSLRAEDTA
VYYCARYRGRLLFDYWGQGTLVTVSSASTKGPSVFPLAPSSKSTSGGTAA
LGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLF
PPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKT
TPPVLDSDGSFFLYSKLTVDKSRWQQGNVFSCSVMHEALHNHYTQKSLSL
SPGK

Figure 10B

Anti-NRP2A YW126.20 hIgG1 P1 file

```
DIQMTQSPSSLSASVGDRVTITCRASQSISSYLAWYQQKPGKAPKLLIYGAS
SRASGVPSRFSGSGSGTDFTLTISSLQPEDFATYYCQQRYSYPITFGQGTKV
EIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVT
KSFNRGECEVQLVESGGGLVQPGGSLRLSCAASGFSFSSRRMSWVRQAPG
KGLEWVSTINPYNGYTYYADSVKGRFTISADTSKNTAYLQMNSLRAEDTA
VYYCARSGPGQFGSTGYYFDYWGQGTLVTVSSASTKGPSVFPLAPSSKSTS
GGTAALGCLVKLYFPEPVTVSWNSGALTSGVHTFPAVLQSSGLYSLSSVV
TVPSSSLGTQTYICNVNHKPSNTKVDKKVEPKSCDKTHTCPPCPAPELLGG
PSVFLFPPKPKDTLMISRTREVTCVVVDVSHEDPEVKFNWYVDGVEVHNA
KTKPREEQYNSTYRVVSVLTVLHQDWLNGKEYKCKVSNKALPAPIEKTIS
KAKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHY
TQKSLSLSPGK
```

Figure 11

Light Chain Variable Domain Sequence Alignment of Anti-panNRP2A YW126.20

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | Kabat - CDR L1 | | | | | | | | | | | | |
| | | | | | | | | | | | | | | | | | | | | | | | | | Chothia - CDR L1 | | | | | | | | | | | | |
| | | | | | | | | | | | | | | | | | | | | | | | | | | | | | Contact - CDR L1 | | | | | | | | |
| huKI | D | I | Q | M | T | Q | S | P | S | S | L | S | A | S | V | G | D | R | V | T | I | T | C | R | A | S | Q | S | I | S | N | Y | L | A | W | Y | Q |
| YW126.20 | D | I | Q | M | T | Q | S | P | S | S | L | S | A | S | V | G | D | R | V | T | I | T | C | R | A | S | Q | S | I | S | S | Y | L | A | W | Y | Q |

| Kabat# | 38 | 39 | 40 | 41 | 41 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 |
|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | Kabat - CDR L2 | | | | | | | | | | | | | | | | | | | | | | | |
| | | | | | | | | | | | | | | Chothia - CDR L2 | | | | | | | | | | | | | | | | | | | | | | | |
| | | | | | | | | | | Contact - CDR L2 | | | | | | | | | | | | | | | | | | | | | | | | | | | |
| huKI | Q | K | P | G | K | A | P | K | L | L | I | Y | A | A | S | S | L | E | S | G | V | P | S | R | F | S | G | S | G | S | G | T | D | F | T | L | T |
| YW126.20 | Q | K | P | G | K | A | P | K | L | L | I | Y | G | A | S | S | R | A | S | G | V | P | S | R | F | S | G | S | G | S | G | T | D | F | T | L | T |

| Kabat# | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | Kabat - CDR L3 | | | | | | | | | | | | | | | | | |
| | | | | | | | | | | | | | | | | | Chothia - CDR L3 | | | | | | | | | | | | | | | | | |
| | | | | | | | | | | | | | | | | | Contact - CDR L3 | | | | | | | | | | | | | | | | | |
| huKI | I | S | S | L | Q | P | E | D | F | A | T | Y | Y | C | Q | Q | Y | N | S | L | P | W | T | F | G | Q | G | T | K | V | E | I | K | R |
| YW126.20 | I | S | S | L | Q | P | E | D | F | A | T | Y | Y | C | Q | Q | R | Y | S | Y | P | I | T | F | G | Q | G | T | K | V | E | I | K | R |

Figure 12

Heavy Chain Variable Domain Sequence Alignment of Anti-panNRP2A YW126.20

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|
| humIII | E | V | Q | L | V | E | S | G | G | G | L | V | Q | P | G | G | S | L | R | L | S | C | A | A | S | G | F | T | F | S | S | Y | A | M | S | W | V | R | Q | A |
| YW126.20 | E | V | Q | L | V | E | S | G | G | G | L | V | Q | P | G | G | S | L | R | L | S | C | A | A | S | G | F | S | F | S | S | R | R | M | S | W | V | R | Q | A |

| Kabat# | 41 | 42 | 43 | 44 | 45 | 46 | 47 | 48 | 49 | 50 | 51 | 52 | A | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|---|---|---|---|---|---|---|---|---|---|---|---|---|---|---|---|---|---|---|---|
| humIII | P | G | K | G | L | E | W | V | S | V | I | S | | G | D | G | G | S | T | Y | Y | A | D | S | V | K | G | R | F | T | I | S | A | D | T | S | K | N | T | A |
| YW126.20 | P | G | K | G | L | E | W | V | S | V | I | | | N | P | Y | N | G | Y | T | Y | Y | A | D | S | V | K | G | R | F | T | I | S | A | D | T | S | K | N | T | A |

| Kabat# | 80 | 81 | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|---|---|---|---|---|---|---|---|---|
| humIII | L | Q | M | N | S | L | R | A | E | D | T | A | V | Y | Y | C | A | R | G | | | | | | | | | | | | | F | D | Y | W | G | Q | G | T |
| YW126.20 | L | Q | M | N | S | L | R | A | E | D | T | A | V | Y | Y | C | A | R | S | G | P | G | Q | F | G | S | I | G | Y | Y | Y | F | E | D | Y | W | G | Q | G | T |

Figure 13

SEQUENCE LISTING

```
<160> NUMBER OF SEQ ID NOS: 7

<210> SEQ ID NO 1
<211> LENGTH: 662
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Thr Pro Pro
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

-continued

```
Phe Asn Arg Gly Glu Cys Glu Val Gln Leu Val Glu Ser Gly Gly
    210                 215                 220
Leu Val Gln Pro Gly Gly Ser Leu Arg Leu Ser Cys Ala Ala Ser Gly
225                 230                 235                 240
Phe Thr Ile Thr Ser Ser Gly Ile His Trp Val Arg Gln Ala Pro Gly
                245                 250                 255
Lys Gly Leu Glu Trp Val Ala Arg Ile Thr Pro Tyr Asp Gly Ser Thr
            260                 265                 270
Asp Tyr Ala Asp Ser Val Lys Gly Arg Phe Thr Ile Ser Ala Asp Thr
        275                 280                 285
Ser Lys Asn Thr Ala Tyr Leu Gln Met Asn Ser Leu Arg Ala Glu Asp
    290                 295                 300
Thr Ala Val Tyr Tyr Cys Ala Arg Tyr Arg Gly Thr Leu Leu Phe Asp
305                 310                 315                 320
Tyr Trp Gly Gln Gly Thr Leu Val Thr Val Ser Ser Ala Ser Thr Lys
                325                 330                 335
Gly Pro Ser Val Phe Pro Leu Ala Pro Ser Ser Lys Ser Thr Ser Gly
            340                 345                 350
Gly Thr Ala Ala Leu Gly Cys Leu Val Lys Asp Tyr Phe Pro Glu Pro
        355                 360                 365
Val Thr Val Ser Trp Asn Ser Gly Ala Leu Thr Ser Gly Val His Thr
    370                 375                 380
Phe Pro Ala Val Leu Gln Ser Ser Gly Leu Tyr Ser Leu Ser Ser Val
385                 390                 395                 400
Val Thr Val Pro Ser Ser Leu Gly Thr Gln Thr Tyr Ile Cys Asn
                405                 410                 415
Val Asn His Lys Pro Ser Asn Thr Lys Val Asp Lys Lys Val Glu Pro
            420                 425                 430
Lys Ser Cys Asp Lys Thr His Thr Cys Pro Pro Cys Pro Ala Pro Glu
        435                 440                 445
Leu Leu Gly Gly Pro Ser Val Phe Leu Phe Pro Pro Lys Pro Lys Asp
    450                 455                 460
Thr Leu Met Ile Ser Arg Thr Pro Glu Val Thr Cys Val Val Val Asp
465                 470                 475                 480
Val Ser His Glu Asp Pro Glu Val Lys Phe Asn Trp Tyr Val Asp Gly
                485                 490                 495
Val Glu Val His Asn Ala Lys Thr Lys Pro Arg Glu Glu Gln Tyr Asn
            500                 505                 510
Ser Thr Tyr Arg Val Val Ser Val Leu Thr Val Leu His Gln Asp Trp
        515                 520                 525
Leu Asn Gly Lys Glu Tyr Lys Cys Lys Val Ser Asn Lys Ala Leu Pro
    530                 535                 540
Ala Pro Ile Glu Lys Thr Ile Ser Lys Ala Lys Gly Gln Pro Arg Glu
545                 550                 555                 560
Pro Gln Val Tyr Thr Leu Pro Pro Ser Arg Glu Glu Met Thr Lys Asn
                565                 570                 575
Gln Val Ser Leu Thr Cys Leu Val Lys Gly Phe Tyr Pro Ser Asp Ile
            580                 585                 590
Ala Val Glu Trp Glu Ser Asn Gly Gln Pro Glu Asn Asn Tyr Lys Thr
        595                 600                 605
Thr Pro Pro Val Leu Asp Ser Asp Gly Ser Phe Phe Leu Tyr Ser Lys
    610                 615                 620
Leu Thr Val Asp Lys Ser Arg Trp Gln Gln Gly Asn Val Phe Ser Cys
625                 630                 635                 640
```

```
Ser Val Met His Glu Ala Leu His Asn His Tyr Thr Gln Lys Ser Leu
            645                 650                 655

Ser Leu Ser Pro Gly Lys
            660

<210> SEQ ID NO 2
<211> LENGTH: 662
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Val Gln Leu Val Glu Ser Gly Gly Gly
    210                 215                 220

Leu Val Gln Pro Gly Gly Ser Leu Arg Leu Ser Cys Ala Ala Ser Gly
225                 230                 235                 240

Phe Thr Ile Thr Ser Ser Gly Ile His Trp Val Arg Gln Ala Pro Gly
                245                 250                 255

Lys Gly Leu Glu Trp Val Ala Arg Ile Thr Pro Tyr Asp Gly Ser Thr
            260                 265                 270

Asp Tyr Ala Asp Ser Val Lys Gly Arg Phe Thr Ile Ser Ala Asp Thr
        275                 280                 285

Ser Lys Asn Thr Ala Tyr Leu Gln Met Asn Ser Leu Arg Ala Glu Asp
    290                 295                 300

Thr Ala Val Tyr Tyr Cys Ala Arg Tyr Arg Gly Arg Leu Leu Phe Asp
305                 310                 315                 320

Tyr Trp Gly Gln Gly Thr Leu Val Thr Val Ser Ser Ala Ser Thr Lys
                325                 330                 335
```

Gly Pro Ser Val Phe Pro Leu Ala Pro Ser Ser Lys Ser Thr Ser Gly
                340                 345                 350

Gly Thr Ala Ala Leu Gly Cys Leu Val Lys Asp Tyr Phe Pro Glu Pro
            355                 360                 365

Val Thr Val Ser Trp Asn Ser Gly Ala Leu Thr Ser Gly Val His Thr
370                 375                 380

Phe Pro Ala Val Leu Gln Ser Ser Gly Leu Tyr Ser Leu Ser Ser Val
385                 390                 395                 400

Val Thr Val Pro Ser Ser Ser Leu Gly Thr Gln Thr Tyr Ile Cys Asn
                405                 410                 415

Val Asn His Lys Pro Ser Asn Thr Lys Val Asp Lys Lys Val Glu Pro
            420                 425                 430

Lys Ser Cys Asp Lys Thr His Thr Cys Pro Pro Cys Pro Ala Pro Glu
        435                 440                 445

Leu Leu Gly Gly Pro Ser Val Phe Leu Phe Pro Pro Lys Pro Lys Asp
450                 455                 460

Thr Leu Met Ile Ser Arg Thr Pro Glu Val Thr Cys Val Val Val Asp
465                 470                 475                 480

Val Ser His Glu Asp Pro Glu Val Lys Phe Asn Trp Tyr Val Asp Gly
                485                 490                 495

Val Glu Val His Asn Ala Lys Thr Lys Pro Arg Glu Glu Gln Tyr Asn
            500                 505                 510

Ser Thr Tyr Arg Val Val Ser Val Leu Thr Val Leu His Gln Asp Trp
        515                 520                 525

Leu Asn Gly Lys Glu Tyr Lys Cys Lys Val Ser Asn Lys Ala Leu Pro
530                 535                 540

Ala Pro Ile Glu Lys Thr Ile Ser Lys Ala Lys Gly Gln Pro Arg Glu
545                 550                 555                 560

Pro Gln Val Tyr Thr Leu Pro Pro Ser Arg Glu Glu Met Thr Lys Asn
                565                 570                 575

Gln Val Ser Leu Thr Cys Leu Val Lys Gly Phe Tyr Pro Ser Asp Ile
            580                 585                 590

Ala Val Glu Trp Glu Ser Asn Gly Gln Pro Glu Asn Asn Tyr Lys Thr
        595                 600                 605

Thr Pro Pro Val Leu Asp Ser Asp Gly Ser Phe Phe Leu Tyr Ser Lys
610                 615                 620

Leu Thr Val Asp Lys Ser Arg Trp Gln Gln Gly Asn Val Phe Ser Cys
625                 630                 635                 640

Ser Val Met His Glu Ala Leu His Asn His Tyr Thr Gln Lys Ser Leu
                645                 650                 655

Ser Leu Ser Pro Gly Lys
            660

<210> SEQ ID NO 3
<211> LENGTH: 668
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

```
Leu Ala Trp Tyr Gln Gln Lys Pro Gly Lys Ala Pro Lys Leu Leu Ile
         35                  40                  45

Tyr Gly Ala Ser Ser Arg Ala Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg Tyr Ser Tyr Pro Ile
                 85                  90                  95

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys Glu Val Gln Leu Val Glu Ser Gly Gly Gly
     210                 215                 220

Leu Val Gln Pro Gly Gly Ser Leu Arg Leu Ser Cys Ala Ala Ser Gly
225                 230                 235                 240

Phe Ser Phe Ser Ser Arg Arg Met Ser Trp Val Arg Gln Ala Pro Gly
                 245                 250                 255

Lys Gly Leu Glu Trp Val Ser Ile Ile Asn Pro Tyr Asn Gly Tyr Thr
             260                 265                 270

Tyr Tyr Ala Asp Ser Val Lys Gly Arg Phe Thr Ile Ser Ala Asp Thr
         275                 280                 285

Ser Lys Asn Thr Ala Tyr Leu Gln Met Asn Ser Leu Arg Ala Glu Asp
     290                 295                 300

Thr Ala Val Tyr Tyr Cys Ala Arg Ser Gly Pro Gly Gln Phe Gly Ser
305                 310                 315                 320

Thr Gly Tyr Tyr Phe Asp Tyr Trp Gly Gln Gly Thr Leu Val Thr Val
                 325                 330                 335

Ser Ser Ala Ser Thr Lys Gly Pro Ser Val Phe Pro Leu Ala Pro Ser
             340                 345                 350

Ser Lys Ser Thr Ser Gly Gly Thr Ala Ala Leu Gly Cys Leu Val Lys
         355                 360                 365

Leu Tyr Phe Pro Glu Pro Val Thr Val Ser Trp Asn Ser Gly Ala Leu
     370                 375                 380

Thr Ser Gly Val His Thr Phe Pro Ala Val Leu Gln Ser Ser Gly Leu
385                 390                 395                 400

Tyr Ser Leu Ser Ser Val Val Thr Val Pro Ser Ser Ser Leu Gly Thr
                 405                 410                 415

Gln Thr Tyr Ile Cys Asn Val Asn His Lys Pro Ser Asn Thr Lys Val
             420                 425                 430

Asp Lys Lys Val Glu Pro Lys Ser Cys Asp Lys Thr His Thr Cys Pro
         435                 440                 445

Pro Cys Pro Ala Pro Glu Leu Leu Gly Gly Pro Ser Val Phe Leu Phe
```

```
                    450                 455                 460
Pro Pro Lys Pro Lys Asp Thr Leu Met Ile Ser Arg Thr Arg Glu Val
465                 470                 475                 480

Thr Cys Val Val Val Asp Val Ser His Glu Asp Pro Glu Val Lys Phe
                485                 490                 495

Asn Trp Tyr Val Asp Gly Val Glu Val His Asn Ala Lys Thr Lys Pro
            500                 505                 510

Arg Glu Glu Gln Tyr Asn Ser Thr Tyr Arg Val Val Ser Val Leu Thr
        515                 520                 525

Val Leu His Gln Asp Trp Leu Asn Gly Lys Glu Tyr Lys Cys Lys Val
    530                 535                 540

Ser Asn Lys Ala Leu Pro Ala Pro Ile Glu Lys Thr Ile Ser Lys Ala
545                 550                 555                 560

Lys Gly Gln Pro Arg Glu Pro Gln Val Tyr Thr Leu Pro Pro Ser Arg
                565                 570                 575

Glu Glu Met Thr Lys Asn Gln Val Ser Leu Thr Cys Leu Val Lys Gly
            580                 585                 590

Phe Tyr Pro Ser Asp Ile Ala Val Glu Trp Glu Ser Asn Gly Gln Pro
        595                 600                 605

Glu Asn Asn Tyr Lys Thr Thr Pro Pro Val Leu Asp Ser Asp Gly Ser
    610                 615                 620

Phe Phe Leu Tyr Ser Lys Leu Thr Val Asp Lys Ser Arg Trp Gln Gln
625                 630                 635                 640

Gly Asn Val Phe Ser Cys Ser Val Met His Glu Ala Leu His Asn His
                645                 650                 655

Tyr Thr Gln Lys Ser Leu Ser Leu Ser Pro Gly Lys
            660                 665

<210> SEQ ID NO 4
<211> LENGTH: 108
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Asn Tyr
             20                  25                  30

Leu Ala Trp Tyr Gln Gln Lys Pro Gly Lys Ala Pro Lys Leu Leu Ile
         35                  40                  45

Tyr Ala Ala Ser Ser Leu Glu Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Leu Pro Trp
                 85                  90                  95

Thr Phe Gly Gln Gly Thr Lys Val Glu Ile Lys Arg
            100                 105

<210> SEQ ID NO 5
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5
```

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
             20                  25                  30

Leu Ala Trp Tyr Gln Gln Lys Pro Gly Lys Ala Pro Lys Leu Leu Ile
         35                  40                  45

Tyr Gly Ala Ser Ser Arg Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg Ser Tyr Pro Ile
             85                  90                  95

Thr Phe Gly Gln Gly Thr Lys Val Glu Ile Lys Arg
            100                 105

<210> SEQ ID NO 6
<211> LENGTH: 107
<212> TYPE: PRT
<213> ORGANISM: Homo sapiens

<400> SEQUENCE: 6

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Val Ile Ser Gly Asp Gly Gly Ser Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95

Ala Arg Gly Phe Asp Tyr Trp Gly Gln Gly Thr
            100                 105

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ser Phe Ser Ser Arg
             20                  25                  30

Arg Met Ser Trp Val Arg Gln Ala Pro Gly Lys Gly Leu Glu Trp Val
         35                  40                  45

Ser Ile Ile Asn Pro Tyr Asn Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
             85                  90                  95
```

-continued

```
Ala Arg Ser Gly Pro Gly Gln Phe Gly Ser Ile Gly Tyr Tyr Phe Asp
            100                 105                 110
Tyr Trp Gly Gln Gly Thr
        115
```

INHIBITION OF TUMOR METASTASIS BY ANTI NEUROPILIN 2 ANTIBODIES

FIELD OF THE INVENTION

The present invention concerns neuropilin-2 (Nrp2) antagonists, especially anti-Nrp2 antibodies, and their use in the prevention and treatment of tumor metastasis.

BACKGROUND OF THE INVENTION

It is now well established that angiogenesis is implicated in the pathogenesis of a variety of disorders. These include solid tumors and metastasis, atherosclerosis, retrolental fibroplasia, hemangiomas, chronic inflammation, intraocular neovascular diseases such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Folkman et al., *J. Biol. Chem.*, 267:10931-10934 (1992); Klagsbrun et al., *Annu. Rev. Physiol.* 53:217-239 (1991); and Garner A., "Vascular diseases", In: Pathobiology of Ocular Disease. A Dynamic Approach, Garner A., Klintworth G K, eds., 2nd Edition (Marcel Dekker, NY, 1994), pp 1625-1710.

In the case of tumor growth, angiogenesis appears to be crucial for the transition from hyperplasia to neoplasia, and for providing nourishment for the growth and metastasis of the tumor. Folkman et al., *Nature* 339:58 (1989). The neovascularization allows the tumor cells to acquire a growth advantage and proliferative autonomy compared to the normal cells. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. Accordingly, a correlation has been observed between density of microvessels in tumor sections and patient survival in breast cancer as well as in several other tumors. Weidner et al., *N. Engl. J. Med* 324:1-6 (1991); Horak et al., *Lancet* 340:1120-1124 (1992); Macchiarini et al., *Lancet* 340:145-146 (1992). The precise mechanisms that control the angiogenic switch is not well understood, but it is believed that neovascularization of tumor mass results from the net balance of a multitude of angiogenesis stimulators and inhibitors (Folkman *Nat Med* 1(1):27-31 (1995)).

It is currently accepted that metastases are responsible for the vast majority, estimated at 90%, of deaths from solid tumors (Gupta and Massague, *Cell* 127, 679-695 (2006)). The complex process of metastasis involves a series of distinct steps including detachment of tumor cells from the primary tumor, intravasation of tumor cells into lymphatic or blood vessels, and extravasation and growth of tumor cells in secondary sites. Analysis of regional lymph nodes in many tumor types suggests that the lymphatic vasculature is an important route for the dissemination of human cancers. Furthermore, in almost all carcinomas, the presence of tumor cells in lymph nodes is the most important adverse prognostic factor. While it was previously thought that such metastases exclusively involved passage of malignant cells along pre-existing lymphatic vessels near tumors, recent experimental studies and clinicopathological reports (reviewed in Achen et al., *Br J Cancer* 94 (2006), 1355-1360 and Nathanson, *Cancer* 98, 413-423 (2003)) suggest that lymphangiogenesis can be induced by solid tumors and can promote tumor spread. These and other recent studies suggest targeting lymphatics and lymphangiogenesis may be a useful therapeutic strategy to restrict the development of cancer metastasis, which would have a significant benefit for many patients.

VEGFC, a member of the vascular endothelial cell factor (VEGF) family, is one of the best studied mediators of lymphatic development. Overexpression of VEGFC in tumor cells was shown to promote tumor-associated lymphangiogenesis, resulting in enhanced metastasis to regional lymph nodes (Karpanen et al., *Faseb J* 20, 1462-1472 (2001); Mandriota et al., *EMBO J.* 20, 672-682 (2001); Skobe et al., *Nat Med* 7, 192-198 (2001); Stacker et al., *Nat Rev Cancer* 2, 573-583 (2002); Stacker et al., *Faseb J* 16, 922-934 (2002)). VEGFC expression has also been correlated with tumor-associated lymphangiogenesis and lymph node metastasis for a number of human cancers (reviewed in Achen et al., 2006, supra. In addition, blockade of VEGFC-mediated signaling has been shown to suppress tumor lymphangiogenesis and lymph node metastases in mice (Chen et al., *Cancer Res* 65, 9004-9011 (2005); He et al., *J. Natl Cancer Inst* 94, 8190825 (2002); Krishnan et al., *Cancer Res* 63, 713-722 (2003); Lin et al., *Cancer Res* 65, 6901-6909 (2005)).

VEGFC is known to bind at least two cell surface receptor families, the tyrosine kinase VEGF receptors and the neuropilin (Nrp) receptors.

Of the three VEGF receptors, VEGFC can bind VEGFR2 and VEGFR3 leading to receptor dimerization (Shinkai et al., *J Biol Chem* 273, 31283-31288 (1998)), kinase activation and autophosphorylation (Heldin, *Cell* 80, 213-223 (1995); Waltenberger et al., *J. Biol Chem* 269, 26988-26995 (1994)). The phosphorylated receptor induces the activation of multiple substrates leading to angiogenesis and lymphangiogenesis (Ferrara et al., *Nat Med* 9, 669-676 (2003)).

The neuropilin (Nrp) family is comprised of two homologous proteins, neuropilin-1 (Nrp1) and neuropilin-2 (Nrp2). In addition to the VEGF receptors, VEGFC also binds to Nrp2, which was initially identified as class 3 semaphorin receptor and mediator of axon guidance (Favier et al., *Blood* 108, 1243-1250 (2006); Soker et al., *J Cell Biochem* 85, 357-368 (2002)). Multiple lines of evidence implicate Nrp2 in the development of the vascular and lymphatic systems. Homozygous Nrp2 mutants show a severe reduction of small lymphatic vessels and capillaries prenatally (Yuan et al., *Development* 129, 4797-4806 (2002)). Furthermore, the dramatic and embryonic lethal vascular defect seen in homozygous Nrp1 mutant mice is enhanced by loss of Nrp2 function leading to earlier lethality (Takashima et al., *Proc Natl Acad Sci USA* 99, 3657-3662 (2002)). However, the role of Nrp2 in modulating adult vascular and lymphatic biology, and more specifically metastasis is unknown.

Nrps have short intracellular domains that are not known to have any enzymatic or signaling activity. It has been proposed that Nrps function to enhance VEGFR signaling by enhancing ligand-VEGF receptor binding (Favier et al., 2006, supra; Soker et al., 2002, supra). Additionally, sema3F, the semaphorin ligand of Nrp2, has been shown to modulate endothelial cell behavior in vitro and in vivo (Bielenberg et al., *J Clin Invest* 114, 1260-1271 (2004); Favier et al., *Blood* 1243-1250, (2006)). However, recent reports have suggested an alternate possibility that Nrps may function independently of VEGF receptors or semaphorin function to modulate endothelial cell (EC) migration (Murga et al., *Blood* 105, 1992-1999 (2005); Pan et al., *Cancer Cell* 11, 53-67 (2007); Wang et al., *J Biol Chem* 278, 48848-48860 (2003)).

Anti-VEGF neutralizing antibodies suppress the growth of a variety of human tumor cell lines in nude mice (Kim et al., *Nature* 362:841-844 (1993); Warren et al., *J. Clin. Invest.* 95:1789-1797 (1995); Borgstrom et al., *Cancer Res.* 56:4032-4039 (1996); Melnyk et al., *Cancer Res.* 56:921-924 (1996)) and also inhibit intraocular angiogenesis in models of ischemic retinal disorders. Adamis et al., *Arch. Opthalmol.* 114:66-71 (1996). Therefore, anti-VEGF monoclonal antibodies or other inhibitors of VEGF action are promising candidates for the treatment of tumors and various intraocular neovascular disorders. Such antibodies are described, for example, in EP 817,648 published Jan. 14, 1998; and in WO98/45331 and WO98/45332, both published Oct. 15, 1998. One of the anti-VEGF antibodies, bevacizumab, has been approved by the FDA for use in combination with a chemotherapy regimen to treat metastatic colorectal cancer (CRC) and non-samll cell lung cancer (NSCLC). And bevacizumab is being investigated in many ongoing clinical trials for treating various cancer indications.

Other anti-VEGF antibodies and anti-Nrp1 antibodies are also known, and described, for example, in Liang et al., *J Mol Biol* 366, 815-829 (2007); Pan et al., *Cancer Cell* 11, 53-67 (2007; and Liang et al., *J Biol Chem* 281, 951-961 (2006)).

SUMMARY OF THE INVENTION

The present invention is based, at least in part, on experimental results obtained with a high-affinity function-blocking antibody to Nrp2. Results obtained with this antibody indicate that Nrp2 plays a role in modulating lymphatic endothelial cell (LEC) migration, and that its function extends beyond its previously assigned role as an enhancer of VEGF receptor activation. In addition, the results demonstrate that blocking Nrp2 leads to an inhibition of lymphangiogenesis and a dramatic reduction in lymph node and distal organ metastasis.

In one aspect, the invention concerns a method for inhibiting lymphatic endothelial cell migration, comprising administering to a mammalian subject in need an effective amount of a neuropilin-2 (Nrp2) antagonist.

In another aspect, the invention concerns a method for inhibiting tumoral lymphangiogenesis, comprising administering to a tumor-bearing mammalian subject an effective amount of a neuropilin-2 (Nrp2) antagonist.

In yet another aspect, the invention concerns a method for inhibiting tumor metastasis, comprising administering to a tumor-bearing mammalian subject an effective amount of a neuropilin-2 (Nrp2) antagonist.

In all embodiments, the mammalian subject preferably is a human patient, such as a human cancer patient, who may have been diagnosed or may be at risk of developing metastasis.

In one embodiment, the cancer is selected from the group consisting of carcinoma, lymphoma, blastoma, sarcoma, and leukemia.

In another embodiment, the cancer is selected from the group consisting of squamous cell cancer, small-cell lung cancer, non-small cell lung cancer, adenocarcinoma of the lung, squamous carcinoma of the lung, cancer of the peritoneum, hepatocellular cancer, gastric cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, B-cell lymphoma, chronic lymphocytic leukemia (CLL); acute lymphoblastic leukemia (ALL); Hairy cell leukemia; chronic myeloblastic leukemia; post-transplant lymphoproliferative disorder (PTLD), abnormal vascular proliferation associated with phakomatoses, edema associated with brain tumors, and Meigs' syndrome.

In yet another embodiment, B-cell lymphoma is selected from the group consisting of low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia.

Without limitation, the Nrp2 antagonist can be an anti-Nrp2 antibody, including anti-Nrp2B and anti-Nrp2A antibodies, such as, for example, antibodies YW68.4.2, YW68.4.2.36, YW126.20, and fragments and variants, such as affinity matured variants thereof.

In another aspect, the invention concerns an anti-Nrp2B antibody comprising the heavy and/or light chain variable region sequence of an antibody selected from the group consisting of YW68.4.2, YW68.4.2.36, and a fragment or variant thereof.

In yet another aspect, the invention concerns an anti-Nrp2A antibody comprising the heavy and/or light chain variable region sequences of YW126.20, or a fragment or variant thereof.

The invention further concerns a composition comprising an antibody of the claimed invention in admixture with a pharmaceutically acceptable carrier.

In a further aspect, the invention concerns a pharmaceutical composition for the prevention or treatment of tumor metastasis comprising an effective amount of an Nrp2 antagonist in admixture with a pharmaceutically acceptable carrier.

In other aspects, the invention concerns Nrp2 antagonists for use in the prevention or treatment of tumor metastasis, and the use of Nrp2 antagonists, such as anti-Nrp2 antibodies in in the prevention or treatment of tumor metastasis.

(D) (P=0.005) tumors, indicating a reduction in functional lymphatics with in these treated tumors. (E) Percent of animals with SLNs containing □-gal expressing C6 tumor cells at various time-points after tumor implantation in the ears of control (black) and Anti-Nrp2$^B$ treated (red) mice. Anti-Nrp2$^3$ treatment results in a delay of arrival of cells at the SLN (p=0.006). N=7 animals per treatment condition per time-point.

FIG. 9. Expression of Nrp2 in different human malignancies. (A-F) Affymetrix HG-U133A and B GeneChip® microarray data for Nrp2 expression in normal colon and colorectal adenocarcinoma (A), normal head and neck tissues and head and neck squamous cell carcinoma (B), normal pancreas and pancreatic adenocarcinoma (C), normal skin and malignant melanoma (D), normal thyroid and papillary thyroid carcinoma (E), and normal breast and Her2-infiltrating ductal adenocarcinoma (F). Each datapoint represents one patient.

FIG. 10. Amino acid sequences of anti-Nrp2$^B$ antibody YW68.4.2 and YW68.4.2.36 (SEQ ID NOs:1 and 2, respectively).

FIG. 11. Amino acid sequence of anti-Nrp2A antibody YW126.20 Fab fragment (SEQ ID NO: 3).

FIG. 12. Alignment of anti-Nrp2A antibody YW126.20 light chain variable domain sequence (SEQ ID NO: 5) with human κ1 sequence (SEQ ID NO: 4).

FIG. 13. Alignment of anti-Nrp2A antibody YW126.20 heavy chain variable domain sequence (SEQ ID NO: 7) with human III (hum III) sequence (SEQ ID NO: 6).

Figure 14:
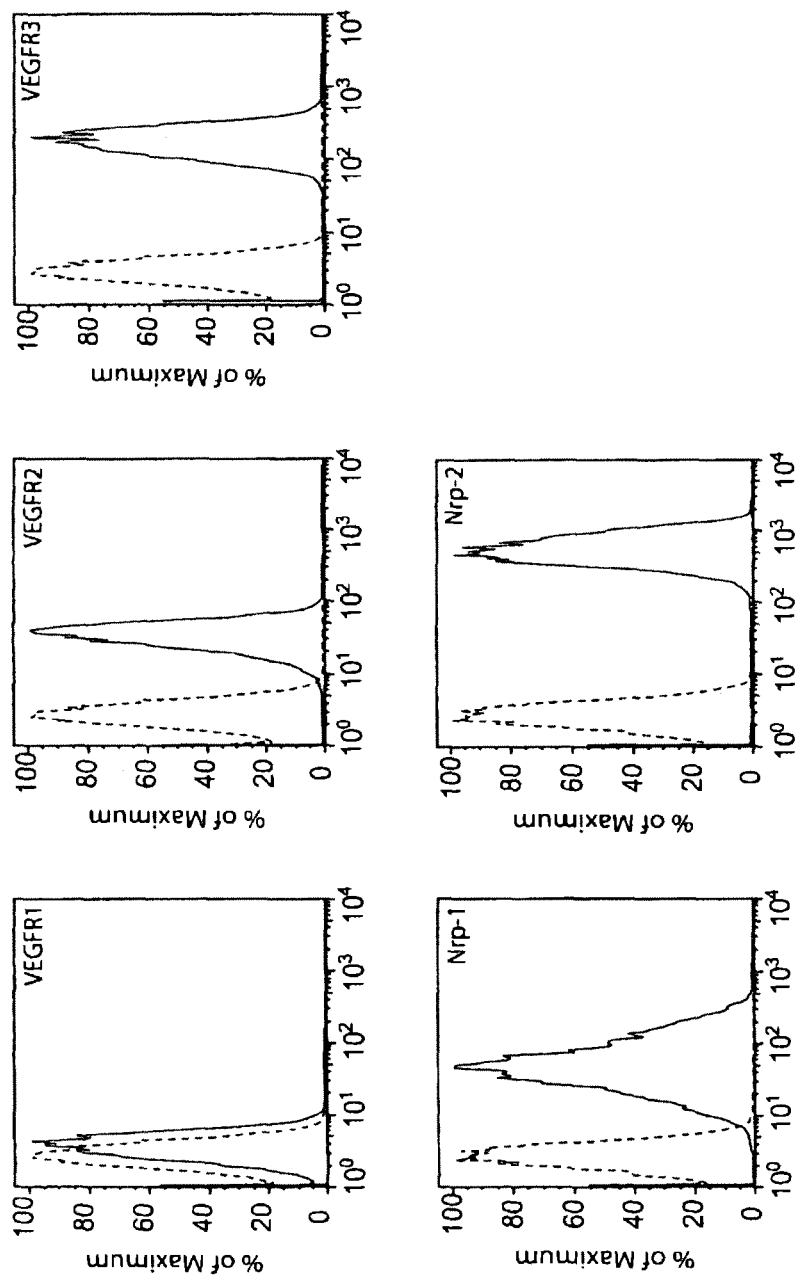

FIG. 14. FACS analysis of VEGF axis receptors' levels on the surface of in vitro cultured LECs. FACS analysis of Nrp1, Nrp2, VEGFR1, VEGFR2 ad VEGFR3 on cultured LECs.

Figure 15B:
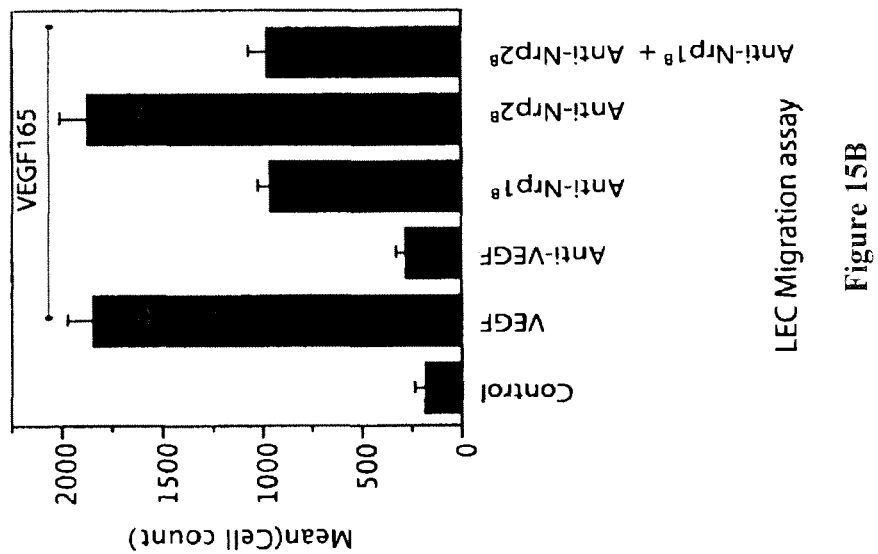
Figure 15A:
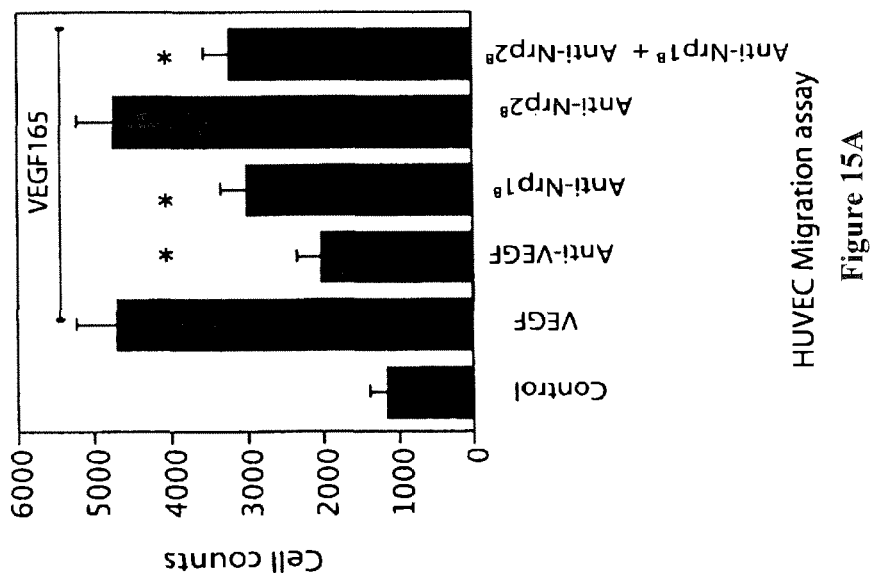

FIG. 15. Anti-Nrp2$^B$ does not block VEGF$_{165}$-induced migration. (A-B) Quantification of HUVEC (A) and LEC (B) migrating in response to 200 ng/ml of VEGF for 18 hours in the presence or absence of Anti-Nrp1$^B$, Anti-Nrp2$^B$ (50 µg/ml) or both antibodies (50 µg/ml). *p<0.05; Error bars represent standard error of the mean.

Figure 16A:
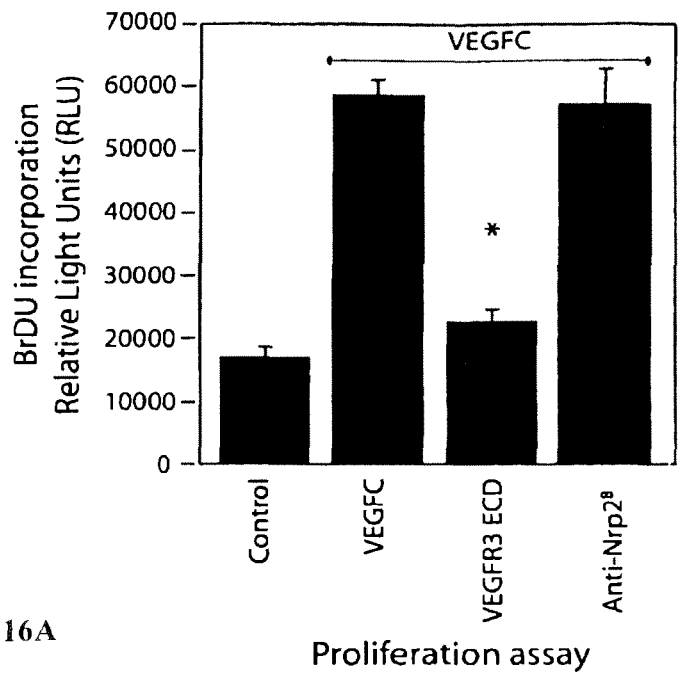
Figure 16B:
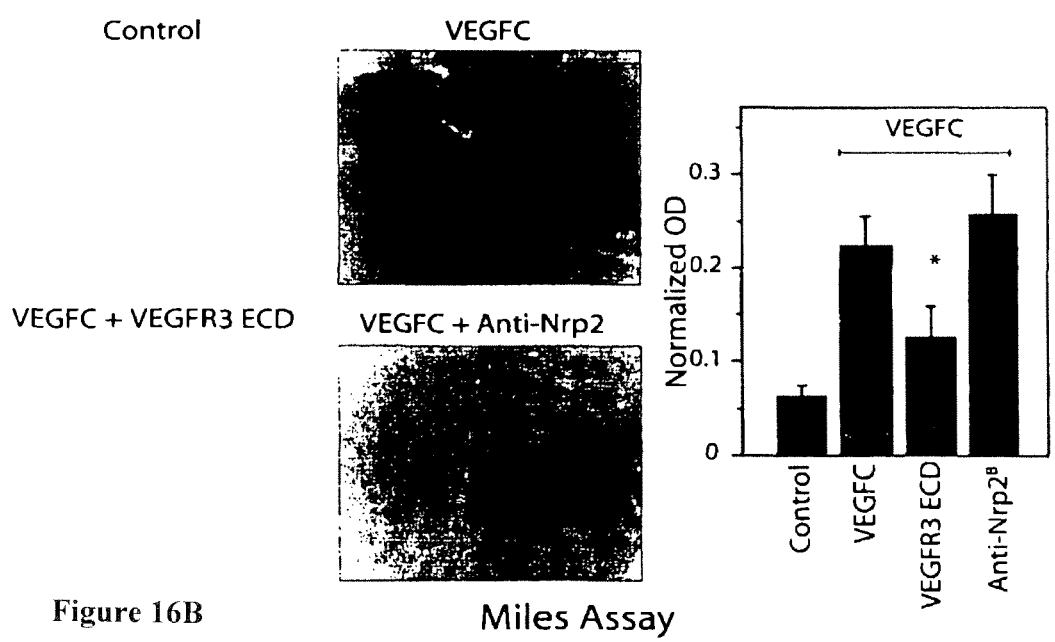

FIG. 16. Effects of Anti-Nrp2$^B$ on VEGFC mediated proliferation and vascular permeability and associated intracellular signaling. (A) Quantification of LEC proliferation induced by 200 ng/ml VEGFC in the presence or absence of Anti-Nrp2$^B$ (50 µg/ml) or VEGFR3 ECD (50 µg/ml) as determined by BrdU incorporation (n=6 per condition). (B) Mouse skin vascular permeability assay. Images were taken from the skin of the same animal. Blue stain represents Evan's blue leakage from the vasculature in response to intradermal delivery of VEGFC after systemic treatment with Anti-Nrp2$^B$ (10 mg/kg) or VEGFR3 ECD (25 mg/kg). Quantification of the Evan's blue dye extracted from skin samples in the permeability assay. Values shown are the average of 6 independent experiments. *p<0.05; Error bars represent standard error of the mean.

Figure 17A:
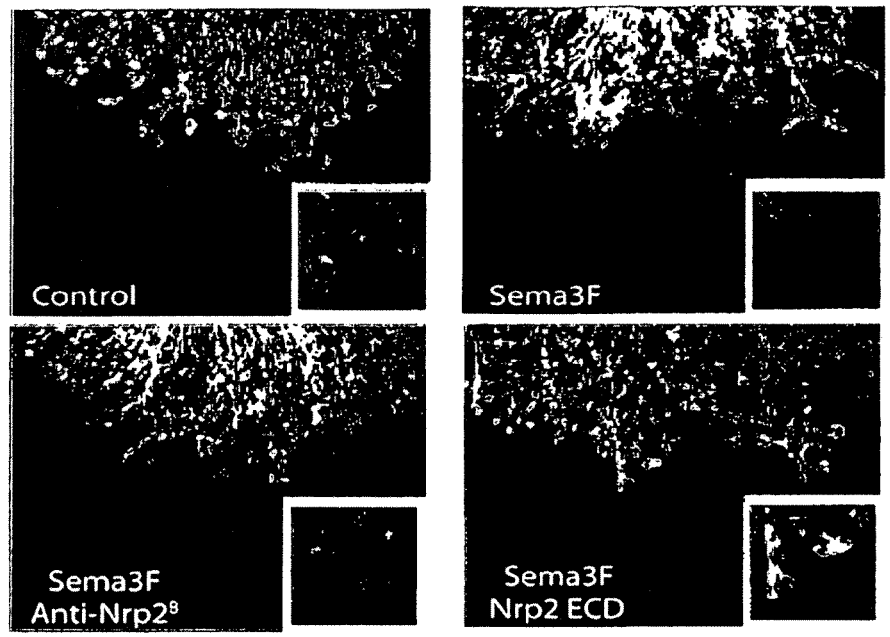
Figure 17B:

FIG. 17. Anti-Nrp2$^B$ does not block Sema3F induced growth cone collapse. (A) Images of E 17.5 Hippocampal growth cones stained with rhodamine conjugated phalloidin. Control growth cones show large actin rich structures at the tip of each axon, which are reduced with Sema3F treatment. Anti-Nrp2$^B$ (50 µm/ml) does not block this collapse. In contrast, Nrp2 ECD (10 ug/ml) does block this collapse. (B) Quality control for anti-Nrp2 immunohistochemistry. Image shows a phage-derived clone that recognized Nrp2 that works in IHC on fresh frozen sections. Nrp2 protein expression is similar to Nrp2 expression as seen using in situ hybridization (Chen et al., Neuron 19, 547-559 (1997)). This antibody was subsequently used for IHC on fresh frozen tumor sections. (Scale bar main images=µm and for inset images=µm.

Figure 18A:
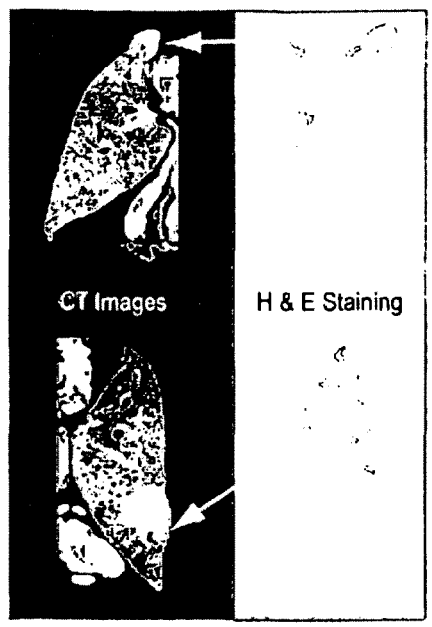
Figure 18B:
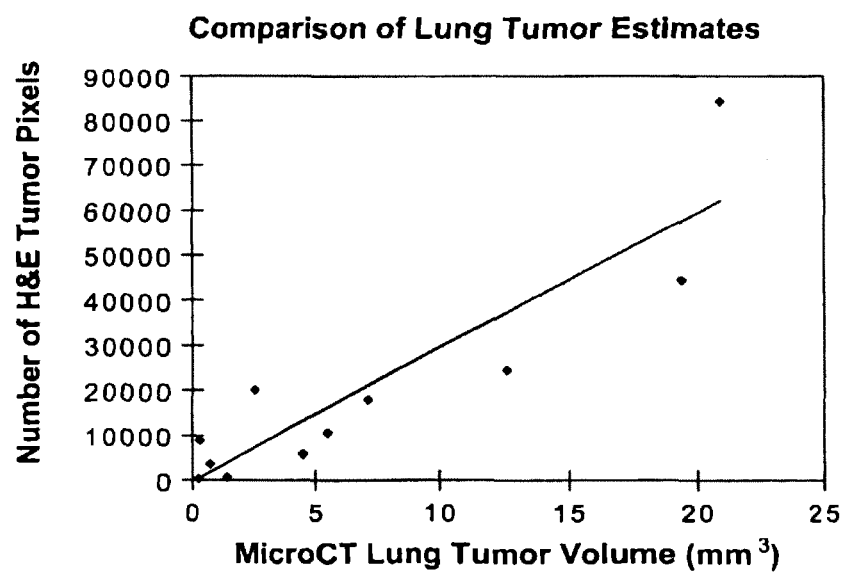

FIG. 18. (A) Micro-CT images of lungs (B) Comparison of lung tumor volume estimates.

DETAILED DESCRIPTION OF THE INVENTION

Definitions

The terms "Neuropilin", "NRP" or "Nrp" are used interchangeably and refer collectively to neuropilin-1 (NRP1, Nrp1), neuropilin-2 (NRP2, Nrp2) and their isoforms and variants, as described in Rossignol et al. (2000) Genomics 70:211-222. Neuropilins are 120 to 130 kDa non-tyrosine kinase receptors. There are multiple NRP-1 and NRP-2 splice variants and soluble isoforms. The basic structure of neuropilins comprises five domains: three extracellular domains (a1a2, b1b2 and c), a transmembrane domain, and a cytoplasmic domain. The a1a2 domain is homologous to complement components C1r and C1s (CUB), which generally contains four cysteine residues that form two disculfid bridges. The b1b2 domain is homologous to coagulation factors V and VIII. The central portion of the c domain is designated as MAM due to its homology to meprin, A5 and receptor tyrosine phosphatase µ proteins. The a1a2 and b1b2 domains are responsible for ligand binding, whereas the c domain is critical for homodimerization or heterodimerization. Gu et al. (2002) J. Biol. Chem. 277:18069-76; He and Tessier-Lavigne (1997) Cell 90:739-51.

"Neuropilin mediated biological activity" refers in general to physiological or pathological events in which neuropilin-1 and/or neuropilin-2 plays a substantial role. Non-limiting examples of such activities are axon guidance during embryonic nervous system development or neuron-regeneration, angiogenesis (including vascular modeling), tumorgenesis and tumor metastasis.

"Neuropilin-2 mediated biological activity" or "Nrp2 mediated biological activity," as used herein, refers in general to physiological or pathological events in which Nrp2 plays a substantial role, such as, for example, enhancing VEGF receptor activation, and, in particular, the ability to modulate lymphatic endothelial cell (EC) migration, role in adult lymphangiogenesis, especially tumoral lymphangiogenesis and tumor metastasis.

The term "antibody" is used in the broadest sense and specifically covers monoclonal antibodies (including full length monoclonal antibodies), polyclonal antibodies, multi-specific antibodies (e.g., bispecific antibodies), and antibody fragments so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352:624-628 and Marks et al. (1991) *J. Mol. Biol.* 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) *Proc. Natl. Acad. Sci. USA* 81:6851-6855).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al. (1986) *Nature* 321:522-525; Riechmann et al. (1988) *Nature* 332:323-329; and Presta (1992) *Curr. Op. Struct. Biol.* 2:593-596.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1\times10^{-7}$ M, preferably no more than about $1\times10^{-8}$ M and most preferably no more than about $1\times10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In a preferred embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions (CDRs; ie., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) *J. Mol. Biol.* 196:901-917). In some instances, a complementarity determining region can include amino acids from both a CDR region defined according to Kabat and a hypervariable loop. For example, the CDRH1 of the heavy chain of antibody 4D5 includes amino acids 26 to 35.

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, eg. NNK, NNS, XYZ, DVK and the like. A "non-random codon set", as used herein, thus refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al. (1999) *J. Mol. Biol.* 296:57-86); Garrard & Henner (1993) *Gene* 128:103). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

The "Fab" fragment contains a variable and constant domain of the light chain and a variable domain and the first constant domain (CH1) of the heavy chain. F(ab')$_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in *The Pharmacology of Monoclonal Antibodies*, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_1$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

The expression "linear antibodies" refers to the antibodies described in Zapata et al. (1995 Protein Eng, 8(10):1057-1062). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

As used herein, "library" refers to a plurality of antibody or antibody fragment sequences (for example, polypeptides of the invention), or the nucleic acids that encode these sequences, the sequences being different in the combination of variant amino acids that are introduced into these sequences according to the methods of the invention.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman (1992) *Curr. Opin. Struct. Biol.* 3:355-362, and references cited therein. In a monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells (1991) *Methods: A companion to Methods in Enzymology* 3:205-0216.

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

As used herein, "solvent accessible position" refers to a position of an amino acid residue in the variable regions of the heavy and light chains of a source antibody or antigen binding fragment that is determined, based on structure, ensemble of structures and/or modeled structure of the antibody or antigen binding fragment, as potentially available for solvent access and/or contact with a molecule, such as an antibody-specific antigen. These positions are typically found in the CDRs and on the exterior of the protein. The solvent accessible positions of an antibody or antigen binding fragment, as defined herein, can be determined using any of a number of algorithms known in the art. Preferably, solvent accessible positions are determined using coordinates from a 3-dimensional model of an antibody, preferably using a computer program such as the InsightII program (Accelrys, San Diego, Calif.). Solvent accessible positions can also be determined using algorithms known in the art (e.g., Lee and Richards (1971) *J. Mol. Biol.* 55, 379 and Connolly (1983) *J. Appl. Cryst.* 16, 548). Determination of solvent accessible positions can be performed using software suitable for protein modeling and 3-dimensional structural information obtained from an antibody. Software that can be utilized for these purposes includes SYBYL Biopolymer Module software (Tripos Associates). Generally and preferably, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios (1994) *Comput. Chem.* 18(4): 377-386.

An "angiogenic factor or agent" is a growth factor which stimulates the development of blood vessels, e.g., promote angiogenesis, endothelial cell growth, stabiliy of blood vessels, and/or vasculogenesis, etc. For example, angiogenic factors, include, but are not limited to, e.g., VEGF and members of the VEGF family, PlGF, PDGF family, fibroblast growth factor family (FGFs), TIE ligands (Angiopoietins), ephrins, Del-1, fibroblast growth factors: acidic (aFGF) and basic (bFGF), Follistatin, Granulocyte colony-stimulating factor (G-CSF), Hepatocyte growth factor (HGF)/scatter factor (SF), Interleukin-8 (IL-8), Leptin, Midkine, neuropilins, Placental growth factor, Platelet-derived endothelial cell growth factor (PD-ECGF), Platelet-derived growth factor, especially PDGF-BB or PDGFR-beta, Pleiotrophin (PTN), Progranulin, Proliferin, Transforming growth factor-alpha (TGF-alpha), Transforming growth factor-beta (TGF-beta), Tumor necrosis factor-alpha (TNF-alpha), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, e.g., Klagsbrun and D'Amore (1991) *Annu. Rev. Physiol.* 53:217-39; Streit and Detmar (2003) *Oncogene* 22:3172-3179; Ferrara & Alitalo (1999) *Nature Medicine* 5(12):1359-1364; Tonini et al. (2003) *Oncogene* 22:6549-6556 (e.g., Table 1 listing known angiogenic factors); and, Sato (2003) *Int. Clin. Oncol.* 8:200-206.

An "anti-angiogenesis agent" or "angiogenesis inhibitor" refers to a small molecular weight substance, an polynucleotide, an polypeptide, an isolated protein, a recombinant protein, an antibody, or conjugates or fusion proteins thereof, that inhibits angiogenesis, vasculogenesis, or undesirable vascular permeability, either directly or indirectly. It should be understood that theanti-angiogenesis agent includes those agents that bind and block the angiogenic activity of the angiogenic factor or its receptor. For example, an anti-angiogenesis agent is an antibody or other antagonist to an angiogenic agent as defined above, e.g., antibodies to VEGF-A or to the VEGF-A receptor (e.g., KDR receptor or Flt-1 receptor), anti-PDGFR inhibitors such as Gleevec™ (Imatinib Mesylate). Anti-angiogensis agents also include native angiogenesis inhibitors, e.g., angiostatin, endostatin, etc. See, e.g., Klagsbrun and D'Amore (1991) *Annu. Rev. Physiol,* 53:217-39; Streit and Detmar (2003) *Oncogene* 22:3172-3179 (e.g., Table 3 listing anti-angiogenic therapy in malignant melanoma); Ferrara & Alitalo (1999) *Nature Medicine* 5(12): 1359-1364; Tonini et al. (2003) *Oncogene* 22:6549-6556 (e.g., Table 2 listing known antiangiogenic factors); and, Sato (2003) *Int. J. Clin. Oncol.* 8:200-206 (e.g., Table 1 listing anti-angiogenic agents used in clinical trials).

The term "VEGF" or "VEGF-A" as used herein refers to the 165-amino acid human vascular endothelial cell growth factor and related 121-, 189-, and 206-amino acid human vascular endothelial cell growth factors, as described by Leung et al. (1989) *Science* 246:1306, and Houck et al. (1991) *Mol. Endocrin,* 5:1806, together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF$_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

An "anti-VEGF antibody" is an antibody that binds to VEGF with sufficient affinity and specificity. Preferably, the anti-VEGF antibody of the invention can be used as a therapeutic agent in targeting and interfering with diseases or conditions wherein the VEGF activity is involved. An anti-VEGF antibody will usually not bind to other VEGF homologues such as VEGF-B or VEGF-C, nor other growth factors such as PlGF, PDGF or bFGF. A preferred anti-VEGF antibody is a monoclonal antibody that binds to the same epitope as the monoclonal anti-VEGF antibody A4.6.1 produced by hybridoma ATCC HB 10709. More preferably the anti-VEGF antibody is a recombinant humanized anti-VEGF monoclonal antibody generated according to Presta et al. (1997) *Cancer Res.* 57:4593-4599, including but not limited to the antibody known as bevacizumab (BV; Avastin™).

The anti-VEGF antibody "Bevacizumab (By)", also known as "rhuMAb VEGF" or "Avastin®, is a recombinant humanized anti-VEGF monoclonal antibody generated according to Presta et al. (1997) *Cancer Res.* 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of Bevacizumab, including most of the framework regions, is derived from human IgG1, and about 7% of the sequence is derived from the murine antibody A4.6.1. Bevacizumab has a molecular mass of about 149,000 daltons and is glycosylated.

The terms "VEGFC" and "VEGF-C" are used interchangeably, and refer to a 419-amino acid human polypeptide (SwissProt: VEGFC_HUMAN P49767), and non-human mammalian orthologs thereof, first described by Joukov et al., *EMBO J* 15, 290-98 (1996), and *EMBO J* 15, 1751 (1996).

The term "Nrp2 antagonist" is used herein to refer to a molecule capable of neutralizing, blocking, inhibiting, abrogating, reducing or interfering with the ability of Nrp2 to modulate lymphatic endothelial cell (EC) migration, or adult lymphangiogenesis, especially tumoral lymphangiogenesis and tumor metastasis.

A "VEGF antagonist" refers to a molecule capable of neutralizing, blocking, inhibiting, abrogating, reducing or interfering with VEGF activities including, but not limited to, its binding to one or more VEGF receptors. VEGF antagonists include, without limitation, anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases. The term "VEGF antagonist," as used herein, specifically includes molecules, including antibodies, antibody fragments, other binding polypeptides, peptides, and non-peptide small molecules, that bind to neuropilin-1 and/or neuropilin-2 (Nrp-1 and/or Nrp-2) and are capable of neutralizing, blocking, inhibiting, abrogating, reducing or interfering with VEGF activities including, but not limited to, anti-Nrp1 and anti-Nrp2 antibodies and antibodies cross-reacting with Nrp1 and Nrp2, provided they are capable of neutralizing, blocking, inhibiting, abrogating, reducing or interfering with VEGF activities. Thus, the term "VEGF activities" specifically includes neuropilin mediated biological activities (as hereinabove defined) of VEGF.

A "semaphorin antagonists" refers to a molecule capable of neutralizing, blocking, inhibiting, abrogating, reducing or interfering with semaphorin activities including, but not limited to, its binding to one or more semaphorin receptors. Semaphorin antagonists include, without limitation, anti-semaphorin antibodies and antigen-binding fragments thereof, receptor molecules and derivatives which bind specifically to semaphorin thereby sequestering its binding to one or more receptors, anti-semaphorin receptor antibodies and semaphorin receptor antagonists such as small molecule inhibitors of semaphorins. The term "semaphorin antagonist," as used herein, specifically includes molecules, including antibodies, antibody fragments, other binding polypeptides, peptides, and non-peptide small molecules, that bind to neuropilin-1 and/or neuropilin-2 (Nrp-1 and/or Nrp-2) and are capable of neutralizing, blocking, inhibiting, abrogating, reducing or interfering with semaphorin activities including, but not limited to, anti-Nrp1 and anti-Nrp2 antibodies and antibodies cross-reacting with Nrp1 and Nrp2, provided they are capable of neutralizing, blocking, inhibiting, abrogating, reducing or interfering with semaphorin activities. Thus, the term "semaphorin activities" specifically includes neuropilin mediated biological activities (as hereinabove defined) of class 3 semaphorins. Such biological activities include, for example, neurite growth inhibitory effect during embryonic nervous system development and neuron-regeneration.

"Treatment" refers to both therapeutic treatment and prophylactic or preventative measures. Those in need of treatment include those already with the disorder as well as those in which the disorder is to be prevented.

A "disorder" is any condition that would benefit from treatment. For example, mammals who suffer from or need prophylaxis against abnormal angiogenesis (excessive, inappropriate or uncontrolled angiogenesis) or vascular permeability. This includes chronic and acute disorders or diseases including those pathological conditions which predispose the mammal to the disorder in question. Non-limiting examples of disorders to be treated herein include malignant and benign tumors; non-leukemias and lymphoid malignancies; and, in particular, tumor (cancer) metastasis.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

The term "anti-neoplastic composition" refers to a composition useful in treating cancer comprising at least one active therapeutic agent, e.g., "anti-cancer agent." Examples of therapeutic agents (anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HERUEGFR inhibitor (e.g., erlotinib (Tarceva™), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1 I and calicheamicin omegaII (see, e.g., Agnew (1994) Chem. Intl. Ed. Engl. 33:183-186); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); Ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva™)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187), and pharmaceutically acceptable salts, acids or derivatives of any of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman (1986) "Prodrugs in Cancer Chemotherapy" *Biochemical*

Society Transactions, 14, pp. 375-382, 615th Meeting Belfast and Stella et al. (1985). "Prodrugs: A Chemical Approach to Targeted Drug Delivery," Directed Drug Delivery, Borchardt et al, (ed.), pp. 247-267, Humana Press. The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "small molecule" is defined herein to have a molecular weight below about 500 Daltons.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

MODES FOR CARRYING OUT THE INVENTION

In one aspect, the present invention is based on experimental data demonstrating that blocking Nrp2 function inhibits tumor metastasis.

A key event in the multi-step process of metastasis involves the egress of a tumor cell away from the primary tumor mass. For solid tumors, the lymphatic system often provides a route for the departing cells. VEGF is known to be a key modulator of lymphangiogenesis and metastasis in many tumor models, and inhibition of the VEGF axis is considered a promising strategy for inhibiting the development of metastasis. Before the present invention, Nrp2, a co-receptor for VEGFC, has not been deemed a target for inhibiting tumor metastasis, possibly due to the lack of lymphatic system defects in adult Nrp2 mutant mice.

The studies underlying the present invention, which are presented in the examples below, support an important role of Nrp2 in tumor lymphangiogenesis and metastasis, only in part by modulating VEGFR3 signaling. Additionally, the data set forth in the Examples demonstrate the presence of functional lymphatic vessels within tumors and show that treating with Anti-Nrp2$^B$ results in a reduction of these functional lymphatics.

Nrp2 Regulated Selective VEGFC Functions, in Part Through a Mechanism Independent Of VEGF Receptor Activation Induction of cellular migration and proliferation are two of the central cellular functions of VEGFC described to date (Joukov et al., Embo J 16, 3898-3911 (1997)). Thus, the present finding that blocking Nrp2 with Anti-Nrp2$^B$ blocked LEC migration but not proliferation (FIGS. 2, 3) was surprising. This selectivity has been recently reported with Nrp2 siRNA knockdown experiments, but was attributed to experimental technical limitations (Favier et al., Blood 108, 1243-1250 (2006)). The data presented herein show that Nrp2's functional selectivity was also noted in vivo, where Anti-Nrp2$^B$ treatment resulted in a reduction of VEGFC driven lymphangiogenesis but not vascular permeability (FIGS. 2, 3). These observations suggest that inhibition with Anti-Nrp2$^B$ does not simply function by disrupting VEGFC signaling. However, it has been determined that blocking Nrp2 did result in a modest reduction in VEGF receptor phosphorylation (FIG. 3) supporting a mechanism where one of Nrp2's roles is to enhance VEGF receptor function. This raised the possibility that different VEGFC-induced physiological events may require different levels of VEGF receptor activation. Thus, a decrease in receptor activation may be sufficient to affect migration, but not proliferation or vascular permeability.

To test this, the VEGFC dose response of VEGF receptor phosphorylation was compared to the dose response of LEC migration (FIG. 3). Doses of VEGFC that led to a receptor phosphorylation level equivalent to that seen with Anti-Nrp2$^B$ treatment did not reduce or inhibit migration. This indicated that the decrease in receptor activation alone did not account for the function blocking effects of Anti-Nrp2$^B$.

Therefore, other mechanisms were investigated by which blocking Nrp2 may selectively affect migration such as modulation of adhesion or motility. Anti-Nrp2$^B$ treatment did not have any effect on LEC mediated adhesion or migration induced by VEGF$_{165}$ (FIG. 2), HGF (FIG. 3) or FGF-2, indicating that it did not generally affect migration by disrupting motility. Additionally, it has been proposed that sema3F, another ligand of Nrp2, may modulate LEC or EC migration, acting as a chemorepellant (Bielenberg et al., J Clin Invest 114, 1260-1271 (2004); Favier et al., Blood 108, 1243-1250 (2006)). However, the Anti-Nrp2$^B$ antibody did not inhibit or potentiate the binding of sema3F to Nrp2 (FIG. 1) or the functional effects of sema3F on responsive neurons FIG. 17).

Thus, it is unlikely that the reduction in VEGFC induced migration by Anti-Nrp2$^B$ can be explained by modulation of sema3F function.

The effect of Anti-Nrp2$^B$ on the formation of the Nrp2/VEGF receptor complex has also been evaluated. In contrast to Nrp1, Nrp2 forms a complex with VEGFR2 and VEGFR3 in the absence of ligand (Favier et al., 2006, supra; Karpanen et al., *Faseb J* 20, 1462-1472 (2006)). Importantly, Anti-Nrp2$^B$ strongly inhibits the formation of these complexes. This observation, in addition to the fact that Nrp2 is significant for more than just augmentation of VEGF receptor function, supports a model in which Nrp2 provides additional functionality to specifically modulate migration, potentially conveying additional machinery to the VEGF receptor complex.

Nrp2 Plays an Important Role in Modulating Adult Lymphangiogenesis.

Analysis of Nrp2 KO mice demonstrates that Nrp2 is a modulator of developmental lymphangiogenesis, presumably via its role as a VEGFC co-receptor (Yuan et al., 2002, supra). However, these mutant mice form functional lymphatics after birth, indicating that either the defect represents a delay rather than inhibition of lymphatic growth or that there is functional compensation by another molecular mediator. Therefore, the role of Nrp2 in maintaining mature lymphatics and modulating adult lymphangiogenesis has not been not known. Expression analysis (FIG. 4) does not support a role of Nrp2 in maintaining lymphatics. Interestingly, Nrp2 is strongly expressed in lymphatics that are present in tumors and within LNs adjacent to tumors, suggesting that Nrp2 may play a role in activated or growing lymphatics. In vitro observations demonstrate that Anti-Nrp2$^B$ is an effective tool in evaluating the role of Nrp2 in these processes. Therefore, Anti-Nrp2$^B$ was tested in vivo using the corneal micropocket assay (FIG. 2). Anti-Nrp2$^B$ effectively blocked the VEGFC induced lymphangiogenesis, surprisingly equivalently to VEGFR3 ECD. Interestingly, Anti-Nrp2$^B$ demonstrated selective inhibitory function in vivo as well, failing to affect VEGFC induced vascular permeability. This corresponds with the in vitro observations that Nrp2 specifically modulates migration, a process important for lymphangiogenesis, but unlikely to play a role in vascular permeability. Finally, these Anti-Nrp2$^B$ treated normal adult animals did not demonstrate any changes to intestinal lymphatics, confirming Nrp2 does not play a role in maintenance of mature lymphatics.

Nrp2 Inhibition Leads to a Reduction in Functional Lymphatics within the Tumor and a Reduction in Metastasis—Likely by Inhibiting Tumor Cells from Leaving the Main Tumor Mass Via the Lymphatic Route.

Inhibition of the VEGFC axis, most often by the use of VEGFR3 ECD, is one of the more commonly utilized strategies for reducing metastasis (Chen et al., 2005. supra; He et al., 2002, supra; Krishnan et al., 2003, supra; Lin et al., 2005, supra). VEGFC can facilitate metastasis potentially by initiating lymphangiogenesis, thereby increasing the surface area of tumor cells in contact with LECs, by modulating LEC adhesive properties or cytokine expression or by increasing vascular permeability (Alitalo and Carmeliet, *Cancer Cell* 1, 219-227 (2002)). As Anti-Nrp2$^B$ modulates selective VEGFC mediated functions including inhibiting VEGFC induced adult lymphangiogenesis, next, the effects of blocking Nrp2 on metastasis were investigated. In order to minimize confounding variables and to unambiguously evaluate the role of Anti-Nrp2$^B$ on metastasis, we picked models where blocking Nrp2 does not affect primary tumor growth and further harvested all animals at the same time-point in the study (Withers and Lee, *Semin Radiat Oncol* 16, 111-119 (2006)).

In both 66c14 as well as C6 tumor models, Anti-Nrp2$^B$ treatment resulted in a significant reduction of metastatic lung nodules by visual inspection (FIGS. 5, 6). This was confirmed by the more sensitive and quantitative micro-CT technique (Li et al., *Technol Cancer Res Treat* 5, 147-155 (2006)). Comparison of Anti-Nrp2$^B$ and VEGFR3 ECD treatments was not possible in 66c14 tumors due to a reduction in primary tumor size with VEGFR3 treatment. However, this analysis was conducted in C6 tumors as their growth was not affected by VEGFR3 ECD treatment. As with the corneal micropocket assay, Anti-Nrp2$^B$ treatment resulted in an equivalent block of metastasis when compared to VEGFR3 ECD.

Figure 7A:
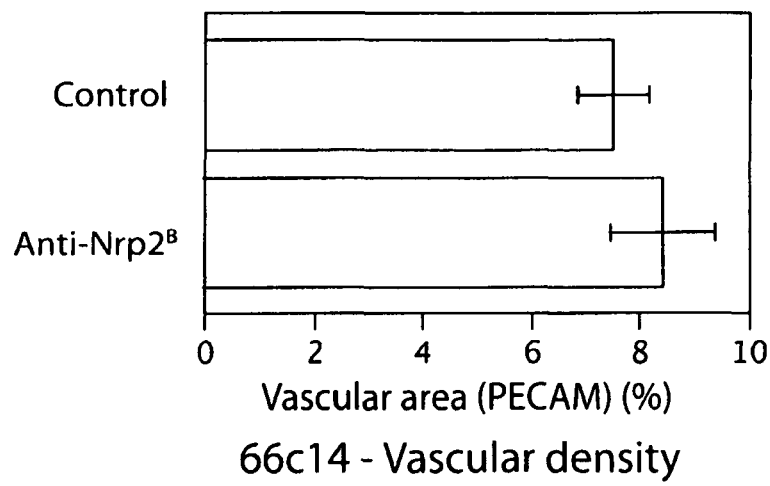
FIG. 7. Anti-Nrp2$^B$ treatment results in a reduction of tumor lymphatic vessels. (A, B) Quantification of vascular vessel density (A) as detected by PECAM-1 IHC and lymphatic vessel density (B) as detected by LYVE-1 IHC in 66c14 tumors treated with control antibody or Anti-Nrp2$^B$. Vessel density was determined from 6 representative images from each of 6 tumors per group, evaluated for mean pixel number by ImageJ. (C) Representative mages of PECAM-1 stained vessels (top row) and LYVE-1 stained lymphatic vessels (middle and bottom rows) in C6 tumors treated with control antibody (left column), VEGFR3 ECD (middle column) or Anti-Nrp2$^B$ (right column). The boxed areas outlined in the middle row are displayed in the bottom row at higher magnification. Quantification of vascular (top graph) and lymphatic (bottom graph) vessel density is to the right of these images. (D) LYVE-1 stained tumors from Anti-Nrp2$^B$ treated animals (bottom panels) harvested at day 4 (Harvest 1) and day 11 (Harvest 2) demonstrate disruption of lymphatic vessels in comparison to control treated animals (top panels). The harvest dates relative to growth curves are shown to the left. Error bars represent standard error of the mean. Scale bar ***.
Figure 7B:
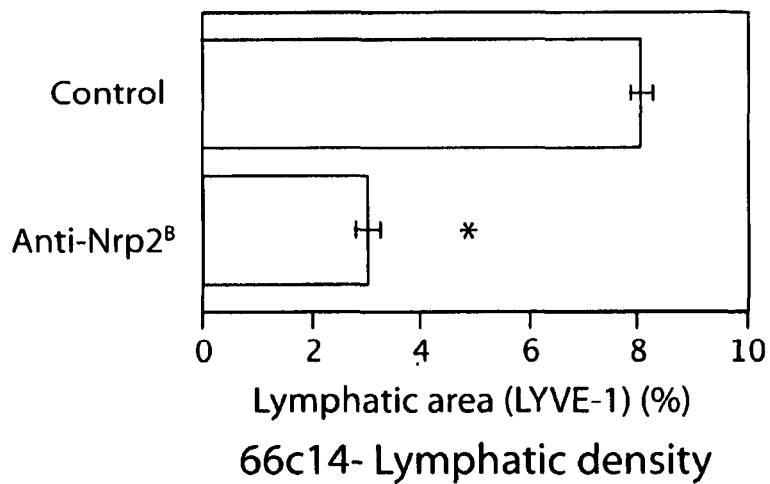
Figure 7C:
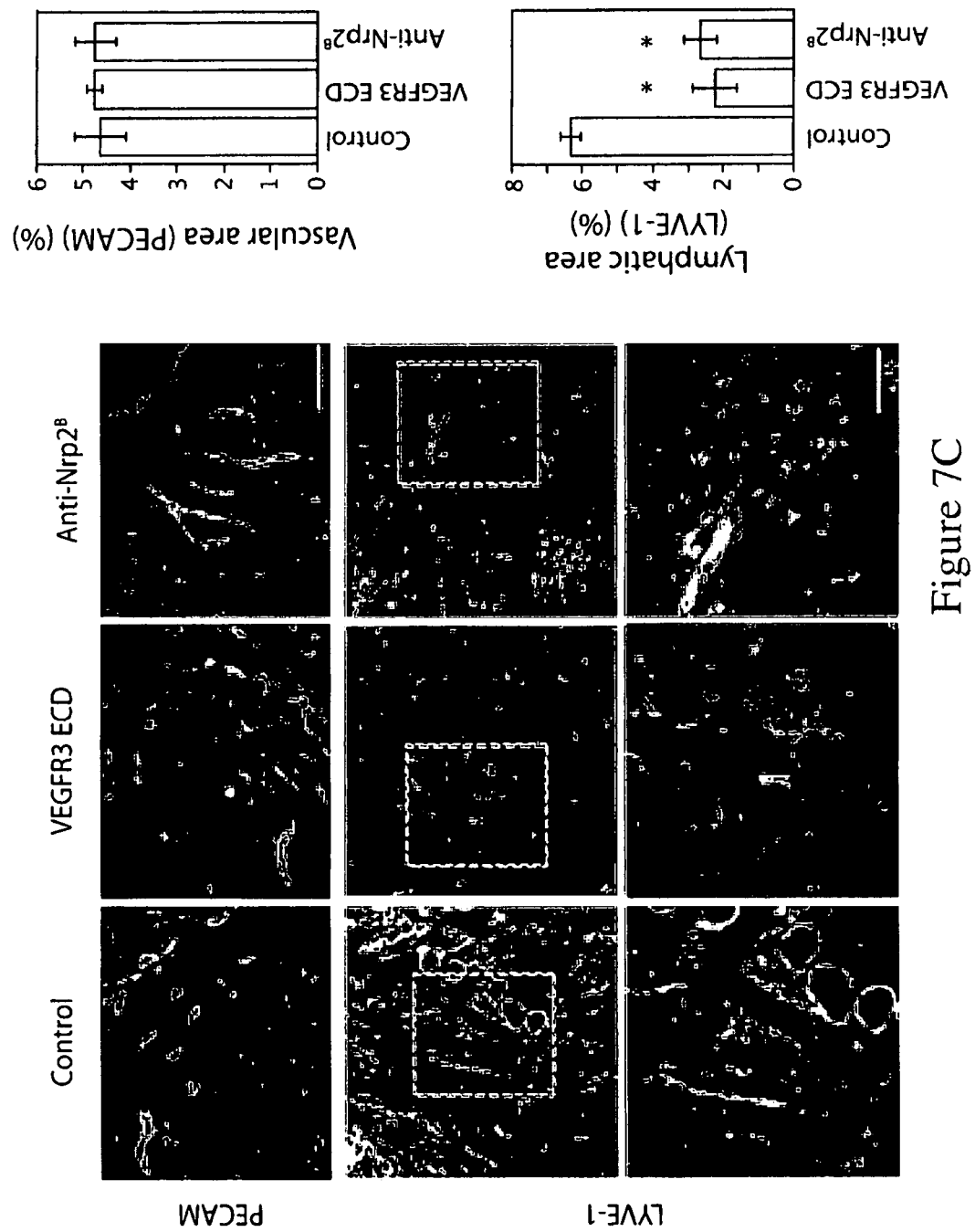
Figure 8A:
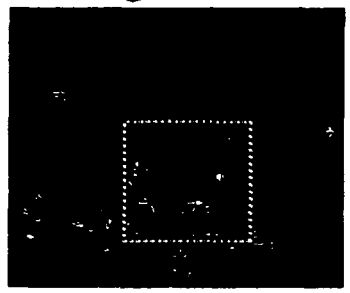
FIG. 8. Anti-Nrp2$^B$ treatment results in a reduction of functional tumor lymphatic vessels and leads to a delay in metastasis to the primary lymph node. (A,B) Polystyrene fluorescent micro-beads (green) are seen exclusively in lymphatic vessels labeled by LYVE-1 IHC (red) after intradermal lymphangiography. The boxed area in A is shown at higher magnification in B. (C-D) Anti-Nrp2$^B$ treatment results in a reduction of evans blue within C6 (C) (P=0.035) and 66c14
Figure 8B:
Figure 8C:
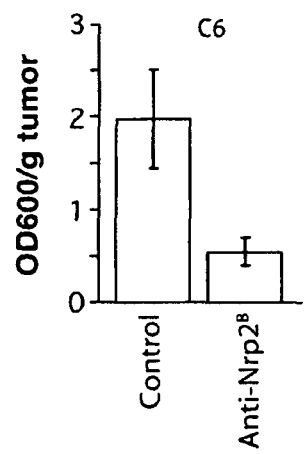
Figure 8D:
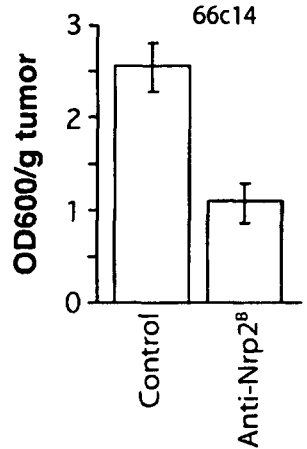
Figure 8E:
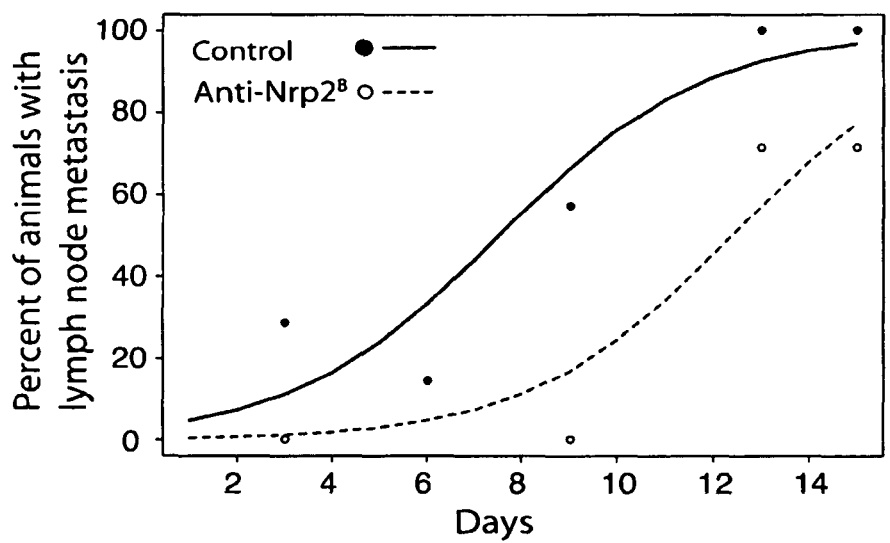
Figure 9A:
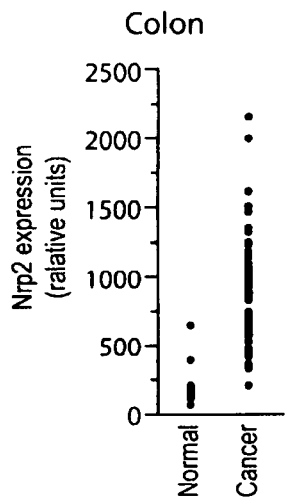
Figure 9B:
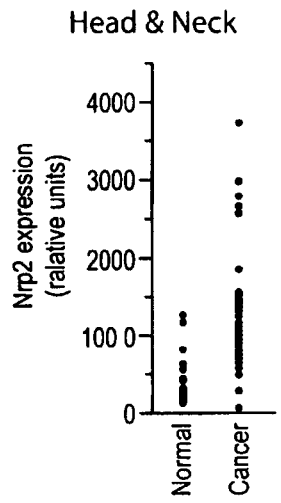
Figure 9C:
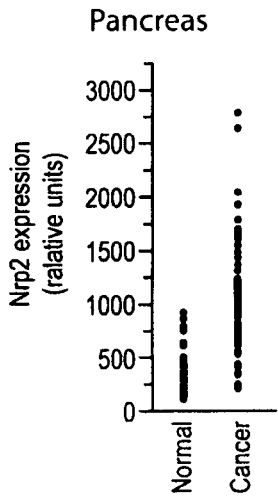
Figure 9D:
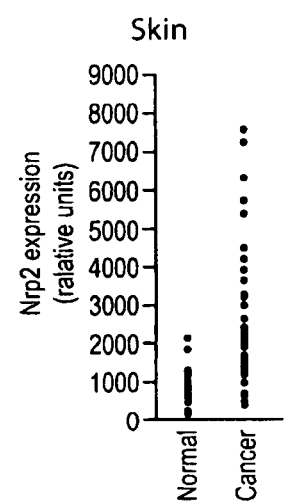
Figure 9E:
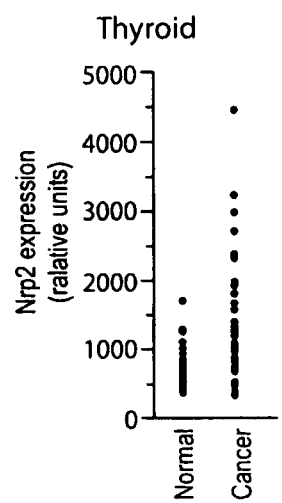
Figure 9F:
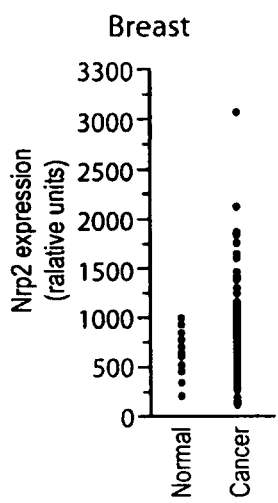

Histologic analysis of the primary tumor indicated that we were not primarily affecting tumor cells. Thus, we evaluated the two potential metastatic routes that were available to tumor cells: blood vessels and lymphatics (FIG. 7). Treatment with Anti-Nrp2$^B$ did not affect the structure or density of blood vessels. Based on the in vitro and corneal micropocket in vivo data, it was hypothesized that blocking Nrp2 should result in a reduction of tumor lymphatics. Anti-Nrp2$^B$ treatment did dramatically reduce the density of lymphatics, and again, to an equivalent degree as VEGFR3 ECD treatment. However, these two treatments did differ in the morphology of the resulting lymphatics. VEGFR3 ECD treatment led to the formation of sparse lymphatic networks lined by unhealthy appearing lymphatic cells. Anti-Nrp2$^B$ treatment, on the other hand, led to the development of short vessels and pockets of isolated healthy appearing lymphatic cells. These differences further support a model where Nrp2 does not simply act to augment VEGF receptor activation, but also brings unique functionality to mediate VEGFC biology. These results also demonstrate that for the experimental paradigms tested, Anti-Nrp2$^B$ acts to inhibit lymphangiogenesis (FIG. 7). However, it cannot be ruled out that Anti-Nrp2' also disrupts more established lymphatic vessels within tumors.

We also sought to determine if intratumoral lymphatics were functional and therefore competent to facilitate metastasis. Lymphangiography was used to identify rare functional intratumoral lymphatics (FIG. 8). The technique used was not adequately analytical to determine the proportion of intratumoral lymphatics that were functional. However, they are likely to represent a small fraction of the total lymphatic population (Padera et al., *Mol Imaging* 1, 9-15 (2002)). As it was possible that we were reducing total lymphatic density while sparing functional vessels (which may have different sensitivity to Anti-Nrp2$^B$), we evaluated the effects of blocking Nrp2 on the formation of functional lymphatic vessels. Anti-Nrp2$^B$ reduced the formation of functional vessels, thereby more directly linking the effects on tumor lymphatics with the observed reduction in metastasis.

Finally, to confirm the consequence of reducing functional lymphatics, the effects of Anti-Nrp2$^B$ on metastasis to the SLN were evaluated. The SLN is the first tissue that tumor cells encounter after departing from the tumor via the lymphatics. Thus, it represents one of the earliest steps in distant organ metastasis (Stracke and Liotta, *In Vivo* 6, 309-316 (1992)). As predicted, Anti-Nrp2$^B$ treatment resulted in a delay of the development of SLN micrometastasis, consistent with the idea that fewer cells were effluxing from the primary tumor mass. This is consistent with evidence that VEGFC increases metastasis by inducing lymphatic hyperplasia and increased delivery of cancer cells to lymph nodes (Hoshida et al., *Cancer Research* 66, 8065-8075 (2006)). Thus, the weight of evidence points to a mechanism by which blocking Nrp2 leads to a reduction in functional tumor lymphatics, thereby preventing tumor cells from initiating the metastatic process by exiting from the primary tumor mass.

Nrp2 as a Metastasis Target.

Numerous clinico-pathologic studies have reported that expression of VEGFC and VEGFR3 correlate with lymph node metastasis and distal metastasis in a number of human cancers (extensively reviewed in Stacker et al., *Nat Rev Cancer,* 2002, supra; Stacker et al., *Faseb* 2002, supra, and He et al., 2004, supra). However, there is limited information related to Nrp2 expression and its relation to metastasis. Indeed, links have only been made between Nrp2 expression and malignancy, particularly in pancreatic cancer (Cohen et al., *Biochem Biophys Res Commun* 284, 395-403 (2001); Fukahi et al., *Clin Cancer Res* 10, 581-590 (2004)) and lung cancer (Kawakami et al., *Cancer* 95, 2196-2201 (2002); Lantuejoul et al., *J Pathol* 200, 336-347 (2003)). It was similarly found that Nrp2 was expressed at higher levels compared to their respective control tissues, not only in pancreatic, but also in colonic adenocarcinoma, head and neck squamous cell carcinoma, melanoma, papillary thyroid carcinoma and infiltrating ductal adenocarcinoma of the breast (FIG. 9). More importantly, when these tumors were subdivided into metastatic and non-metastatic groups, Nrp2 expression was noted to be statistically higher in the metastatic group in most of these tumor types. Interestingly, these tumor types all have confirmed intratumoral lymphangiogenesis that furthermore has been correlated with lymph node metastasis (Achen et al., 2006, supra; Achen and Stacker, *Int J Cancer* 119, 1755-1760 (2006)). This indicates that the discussed experimental findings are expected to extend to human patients with a variety of tumor types.

In conclusion, the data discussed herein and presented in the Examples below show that Nrp2 plays a role in modulating VEGFC driven cellular migration and provide evidence that Nrp2 may act through multiple mechanisms including enhancing VEGF receptor activation and mechanisms independent of VEGF receptor signaling. Additionally, blocking Nrp2 function using anti-Nrp2$^B$ results in a dramatic reduction of VEGFC induced lymphangiogenesis in adult mice. This treatment also results in a reduction of metastasis, likely via a reduction in the development of functional lymphatics. These data, along with analysis of Nrp2 expression in a number of human tumors, suggest that Nrp2 is a valid target to modulate metastasis.

Production of Anti-Nrp2 Antibodies

The invention herein includes the production and use of anti-NRP2 antibodies. Exemplary methods for generating antibodies are described in more detail in the following sections.

Anti-NRP2 antibodies are selected using an NRP2 antigen derived from a mammalian species. Preferably the antigen is human NRP2 (hNRP2). However, NRP2s from other species such as murine NRP2 (mNRP2) can also be used as the target antigen. The NRP2 antigens from various mammalian species may be isolated from natural sources. In other embodiments, the antigen is produced recombinantly or made using other synthetic methods known in the art.

The antibody selected will normally have a sufficiently strong binding affinity for the NRP2 antigen. For example, the antibody may bind hNRP2 with a $K_d$ value of no more than about 5 nM, preferably no more than about 2 nM, and more preferably no more than about 500 pM. Antibody affinities may be determined by a surface plasmon resonance based assay (such as the BIAcore assay as described in Examples); enzyme-linked immunoabsorbent assay (ELISA); and competition assays (e.g. RIA's), for example.

Also, the antibody may be subject to other biological activity assays, e.g., in order to evaluate its effectiveness as a therapeutic. Such assays are known in the art and depend on the target antigen and intended use for the antibody. Examples include the HUVEC inhibition assay (as described in the Examples below); tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062).

To screen for antibodies which bind to a particular epitope on the antigen of interest, a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al. (1995) *J. Biol. Chem.* 270:1388-1394, can be performed to determine whether the antibody binds an epitope of interest.

Generation of Anti-NRP2 Antibodies from Synthetic Antibody Phage Libraries

In a preferred embodiment, the anti-NRP2 antibodies are selected using a unique phage display approach. The approach involves generation of synthetic antibody phage libraries based on single framework template, design of sufficient diversities within variable domains, display of polypeptides having the diversified variable domains, selection of candidate antibodies with high affinity to target NRP antigen, and isolation of the selected antibodies.

Details of the phage display methods can be found, for example, in WO03/102157 published Dec. 11, 2003.

In one aspect, the antibody libraries can be generated by mutating the solvent accessible and/or highly diverse positions in at least one CDR of an antibody variable domain. Some or all of the CDRs can be mutated using the methods provided herein. In some embodiments, it may be preferable to generate diverse antibody libraries by mutating positions in CDRH1, CDRH2 and CDRH3 to form a single library or by mutating positions in CDRL3 and CDRH3 to form a single library or by mutating positions in CDRL3 and CDRH1, CDRH2 and CDRH3 to form a single library.

A library of antibody variable domains can be generated, for example, having mutations in the solvent accessible and/or highly diverse positions of CDRH1, CDRH2 and CDRH3. Another library can be generated having mutations in CDRL1, CDRL2 and CDRL3. These libraries can also be used in conjunction with each other to generate binders of desired affinities. For example, after one or more rounds of selection of heavy chain libraries for binding to a target antigen, a light chain library can be replaced into the population of heavy chain binders for further rounds of selection to increase the affinity of the binders.

Preferably, a library is created by substitution of original amino acids with variant amino acids in the CDRH3 region of the variable region of the heavy chain sequence. The resulting library can contain a plurality of antibody sequences, wherein the sequence diversity is primarily in the CDRH3 region of the heavy chain sequence.

In one aspect, the library is created in the context of the humanized antibody 4D5 sequence, or the sequence of the framework amino acids of the humanized antibody 4D5 sequence. Preferably, the library is created by substitution of at least residues 95-100a of the heavy chain with amino acids encoded by the DVK codon set, wherein the DVK codon set is used to encode a set of variant amino acids for every one of these positions. An example of an oligonucleotide set that is useful for creating these substitutions comprises the sequence (DVK)$_7$. In some embodiments, a library is created by substitution of residues 95-100a with amino acids encoded by both DVK and NNK codon sets. An example of an oligonucleotide set that is useful for creating these substitutions comprises the sequence (DVK)$_6$ (NNK). In another embodiment, a library is created by substitution of at least residues 95-100a with amino acids encoded by both DVK and NNK codon sets. An example of an oligonucleotide set that is useful for creating these substitutions comprises the sequence (DVK)$_5$ (NNK). Another example of an oligonucleotide set that is useful for creating these substitutions comprises the sequence (NNK)$_6$. Other examples of suitable oligonucleotide sequences can be determined by one skilled in the art according to the criteria described herein.

In another embodiment, different CDRH3 designs are utilized to isolate high affinity binders and to isolate binders for a variety of epitopes. The range of lengths of CDRH3 generated in this library is 11 to 13 amino acids, although lengths different from this can also be generated. H3 diversity can be expanded by using NNK, DVK and NVK codon sets, as well as more limited diversity at N and/or C-terminal.

Diversity can also be generated in CDRH1 and CDRH2. The designs of CDR-H1 and H2 diversities follow the strategy of targeting to mimic natural antibodies repertoire as described with modification that focus the diversity more closely matched to the natural diversity than previous design.

For diversity in CDRH3, multiple libraries can be constructed separately with different lengths of H3 and then combined to select for binders to target antigens. The multiple libraries can be pooled and sorted using solid support selection and solution sorting methods as described previously and herein below. Multiple sorting strategies may be employed. For example, one variation involves sorting on target bound to a solid, followed by sorting for a tag that may be present on the fusion polypeptide (eg. anti-gD tag) and followed by another sort on target bound to solid. Alternatively, the libraries can be sorted first on target bound to a solid surface, the eluted binders are then sorted using solution phase binding with decreasing concentrations of target antigen. Utilizing combinations of different sorting methods provides for minimization of selection of only highly expressed sequences and provides for selection of a number of different high affinity clones.

High affinity binders for the target NRP2 antigen can be isolated from the libraries. Limiting diversity in the H1/H2 region decreases degeneracy about $10^4$ to $10^5$ fold and allowing more H3 diversity provides for more high affinity binders. Utilizing libraries with different types of diversity in CDRH3 (eg. utilizing DVK or NVT) provides for isolation of binders that may bind to different epitopes of a target antigen.

Of the binders isolated from the pooled libraries as described above, it has been discovered that affinity may be further improved by providing limited diversity in the light chain. Light chain diversity is generated in this embodiment as follows in CDRL1: amino acid position 28 is encoded by RDT; amino acid position 29 is encoded by RKT; amino acid position 30 is encoded by RVW; amino acid position 31 is encoded by ANW; amino acid position 32 is encoded by THT; optionally, amino acid position 33 is encoded by CTG; in CDRL2: amino acid position 50 is encoded by KBG; amino acid position 53 is encoded by AVC; and optionally, amino acid position 55 is encoded by GMA; in CDRL3: amino acid position 91 is encoded by TMT or SRT or both; amino acid position 92 is encoded by DMC; amino acid position 93 is encoded by RVT; amino acid position 94 is encoded by NHT; and amino acid position 96 is encoded by TWT or YKG or both.

In another embodiment, a library or libraries with diversity in CDRH1, CDRH2 and CDRH3 regions is generated. In this embodiment, diversity in CDRH3 is generated using a variety of lengths of H3 regions and using primarily codon sets XYZ and NNK or NNS. Libraries can be formed using individual oligonucleotides and pooled or oligonucleotides can be pooled to form a subset of libraries. The libraries of this embodiment can be sorted against target bound to solid. Clones isolated from multiple sorts can be screened for specificity and affinity using ELISA assays. For specificity, the clones can be screened against the desired target antigens as well as other nontarget antigens. Those binders to the target NRP1 antigen can then be screened for affinity in solution binding competition ELISA assay or spot competition assay. High affinity binders can be isolated from the library utilizing XYZ codon sets prepared as described above. These binders can be readily produced as antibodies or antigen binding fragments in high yield in cell culture.

In some embodiments, it may be desirable to generate libraries with a greater diversity in lengths of CDRH3 region. For example, it may be desirable to generate libraries with CDRH3 regions ranging from about 7 to 19 amino acids.

High affinity binders isolated from the libraries of these embodiments are readily produced in bacterial and eukaryotic cell culture in high yield. The vectors can be designed to readily remove sequences such as gD tags, viral coat protein component sequence, and/or to add in constant region sequences to provide for production of full length antibodies or antigen binding fragments in high yield.

A library with mutations in CDRH3 can be combined with a library containing variant versions of other CDRs, for example CDRL1, CDRL2, CDRL3, CDRH1 and/or CDRH2. Thus, for example, in one embodiment, a CDRH3 library is combined with a CDRL3 library created in the context of the humanized 4D5 antibody sequence with variant amino acids at positions 28, 29, 30, 31, and/or 32 using predetermined codon sets. In another embodiment, a library with mutations to the CDRH3 can be combined with a library comprising variant CDRH1 and/or CDRH2 heavy chain variable domains. In one embodiment, the CDRH1 library is created with the humanized antibody 4D5 sequence with variant amino acids at positions 28, 30, 31, 32 and 33. A CDRH2 library may be created with the sequence of humanized antibody 4D5 with variant amino acids at positions 50, 52, 53, 54, 56 and 58 using the predetermined codon sets.

Anti-NRP2 Antibody Mutants

The anti-NRP2 antibody generated from phage libraries can be further modified to generate antibody mutants with improved physical, chemical and or biological properties over the parent antibody. Where the assay used is a biological activity assay, the antibody mutant preferably has a biological activity in the assay of choice which is at least about 10 fold better, preferably at least about 20 fold better, more preferably at least about 50 fold better, and sometimes at least about 100 fold or 200 fold better, than the biological activity of the parent antibody in that assay. For example, an anti-NRP1 antibody mutant preferably has a binding affinity for NRP which is at least about 10 fold stronger, preferably at least about 20 fold stronger, more preferably at least about 50 fold stronger, and sometimes at least about 100 fold or 200 fold stronger, than the binding affinity of the parent anti-NRP antibody.

To generate the antibody mutant, one or more amino acid alterations (e.g. substitutions) are introduced in one or more of the hypervariable regions of the parent antibody. Alternatively, or in addition, one or more alterations (e.g. substitutions) of framework region residues may be introduced in the parent antibody where these result in an improvement in the binding affinity of the antibody mutant for the antigen from the second mammalian species. Examples of framework region residues to modify include those which non-covalently bind antigen directly (Amit et al. (1986) *Science* 233:747-753); interact with/effect the conformation of a CDR (Chothia et al. (1987) *J. Mal. Biol.* 196:901-917); and/or participate in the $V_L$-$V_H$ interface (EP 239 400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant will comprise additional hypervariable region alteration(s).

The hypervariable region residues which are altered may be changed randomly, especially where the starting binding affinity of the parent antibody is such that such randomly produced antibody mutants can be readily screened.

One useful procedure for generating such antibody mutants is called "alanine scanning mutagenesis" (Cunningham and Wells (1989) *Science* 244:1081-1085). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. The ala-mutants produced this way are screened for their biological activity as described herein.

Normally one would start with a conservative substitution such as those shown below under the heading of "preferred substitutions". If such substitutions result in a change in biological activity (e.g. binding affinity), then more substantial changes, denominated "exemplary substitutions" in the following table, or as further described below in reference to amino acid classes, are introduced and the products screened.
Preferred Substitutions:

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Even more substantial modifications in the antibodies biological properties are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr, asn, gln;
(3) acidic: asp, glu;
(4) basic: his, lys, arg;
(5) residues that influence chain orientation: gly, pro; and
(6) aromatic: trp, tyr, phe.

Non-conservative substitutions will entail exchanging a member of one of these classes for another class.

In another embodiment, the sites selected for modification are affinity matured using phage display (see above).

Nucleic acid molecules encoding amino acid sequence mutants are prepared by a variety of methods known in the art. These methods include, but are not limited to, oligonucleotide-mediated (or site-directed) mutagenesis, PCR mutagenesis, and cassette mutagenesis of an earlier prepared mutant or a non-mutant version of the parent antibody. The preferred method for making mutants is site directed mutagenesis (see, e.g., Kunkel (1985) *Proc. Natl. Acad. Sci. USA* 82:488).

In certain embodiments, the antibody mutant will only have a single hypervariable region residue substituted. In other embodiments, two or more of the hypervariable region residues of the parent antibody will have been substituted, e.g. from about two to about ten hypervariable region substitutions.

Ordinarily, the antibody mutant with improved biological properties will have an amino acid sequence having at least 75% amino acid sequence identity or similarity with the amino acid sequence of either the heavy or light chain variable domain of the parent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e same residue) or similar (i.e. amino acid residue from the same group based on common side-chain properties, see above) with the parent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

Following production of the antibody mutant, the biological activity of that molecule relative to the parent antibody is determined. As noted above, this may involve determining the binding affinity and/or other biological activities of the antibody. In a preferred embodiment of the invention, a panel of antibody mutants is prepared and screened for binding affinity for the antigen such as NRP1 or a fragment thereof. One or more of the antibody mutants selected from this initial screen are optionally subjected to one or more further biological activity assays to confirm that the antibody mutant(s) with enhanced binding affinity are indeed useful, e.g. for preclinical studies.

The antibody mutant(s) so selected may be subjected to further modifications, oftentimes depending on the intended use of the antibody. Such modifications may involve further alteration of the amino acid sequence, fusion to heterologous polypeptide(s) and/or covalent modifications such as those elaborated below. With respect to amino acid sequence alterations, exemplary modifications are elaborated above. For example, any cysteine residue not involved in maintaining the proper conformation of the antibody mutant also may be substituted, generally with serine, to improve the oxidative stability of the molecule and prevent aberrant cross linking. Conversely, cysteine bond(s) may be added to the antibody to improve its stability (particularly where the antibody is an antibody fragment such as an Fv fragment). Another type of amino acid mutant has an altered glycosylation pattern. This may be achieved by deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Vectors, Host Cells and Recombinant Methods

The anti-Nrp2 antibodies of the invention can be produced recombinantly, using techniques and materials readily obtainable.

For recombinant production of an anti-NRP2 antibody, the nucleic acid encoding it is isolated and inserted into a replicable vector for further cloning (amplification of the DNA) or for expression. DNA encoding the antibody is readily isolated or synthethized using conventional procedures (e.g., by using oligonucleotide probes that are capable of binding specifically to DNAs encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, Ipp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al. (1979) *Nature* 282:39). The trp1 gene provides a selection marker for a mutant strain of yeast lacking the ability to grow in tryptophan, for example, ATCC No. 44076 or PEP4-1. Jones (1977) *Genetics* 85:12. The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg (1990) *Bio/Technology* 8:135. Stable multi-copy expression vectors for secretion of mature recombinant human serum albumin by industrial strains of *Kluyveromyces* have also been disclosed. Fleer et al. (1991) *Bio/Technology* 9:968-975.

(iv) Promoter Component

Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al. (1982) *Nature* 297:598-601 on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv (1982) *Nature* 297:17-18 on enhancing elements for activation of eukaryotic promoters. The enhancer may be spliced into the vector at a position 5' or 3' to the antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wick-*

*eramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al. (1977) *J. Gen Virol.* 36:59); baby hamster kidney cells (BHK, ATCC CCL 10); Chinese hamster ovary cells/-DHFR(CHO, Urlaub et al. (1980) *Proc. Natl. Acad. Sci. USA* 77:4216); mouse sertoli cells (TM4, Mather (1980) *Biol. Reprod.* 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al. (1982) *Annals N.Y. Acad, Sci.* 383:44-68); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al. (1979) *Meth. Enz.* 58:44, Barnes et al. (1980) *Anal. Biochem.* 102:255, U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Antibody Purification

When using recombinant techniques, the antibody can be produced intracellularly, in the periplasmic space, or directly secreted into the medium. It the anyway is produced intracellularly, as a first step, the particulate debris, either host cells or lysed fragments, is removed, for example, by centrifugation or ultrafiltration. Carter et al. (1992) *Blo/Technology* 10:163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al. (1983) *J. Immunol. Meth.* 62:1-13). Protein G is recommended for all mouse isotypes and for human γ3 (Guss et al. (1986) *EMBO J.* 5:15671575). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Formulations

Therapeutic formulations of the antibody are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to further provide an immunosuppressive agent, an anticancer agent, an anti-angiogenic agent, an anti-neoplastic agent, a cytotoxic agent and/or a chemotherapeutic agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Therapeutic Uses

It is contemplated that the antibodies of the present invention may be used to treat a mammal. In one embodiment, the antibody is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the antibody or may be used to study toxicity of the antibody of interest. In each of these embodiments, dose escalation studies may be performed in the mammal. Where the antibody is an anti-NRP2 antibody, it may be administered to a host rodent in a solid tumor model, for example.

In addition, or in the alternative, the antibody is used to treat a human, e.g. a patient suffering from a disease or disorder who could benefit from administration of the antibody.

The present invention encompasses the prevention and treatment of tumoral lymphangiogenesis, the prevention and treatment of tumor metastasis and anti-angiogenic cancer therapy, a novel cancer treatment strategy aimed at inhibiting the development of tumor blood vessels required for providing nutrients to support tumor growth. The invention specifically includes inhibiting the neoplastic growth of tumor at the primary site as well as preventing and/or treating metastasis of tumors at the secondary sites, therefore allowing attack of the tumors by other therapeutics. Examples of cancer to be treated (including prevention) herein include, but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. More particularly, cancers that are amenable to treatment by the antibodies of the invention include breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma, and multiple myeloma.

It is contemplated that when used to treat various diseases such as tumors, the antibodies of the invention can be combined with other therapeutic agents suitable for the same or similar diseases. When used for treating cancer, antibodies of the present invention may be used in combination with conventional cancer therapies, such as surgery, radiotherapy, chemotherapy or combinations thereof.

In certain aspects, other therapeutic agents useful for combination cancer therapy with the antibody of the invention include other anti-angiogenic agents. Many anti-angiogenic agents have been identified and are known in the arts, including those listed by Carmeliet and Jain (2000).

In one aspect, the antibody of the invention is used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof. Alternatively, or in addition, two or more anti-NRP1 antibodies may be co-administered to the patient. In a more preferred embodiment, the anti-NRP1$^A$ or anti-NRP$^B$ antibody of the invention is used in combination with an anti-VEGF antibody to generate additive or synergistic effects. Preferred anti-VEGF antibodies include those that bind to the same epitope as the anti-hVEGF antibody A4.6.1. More preferably the anti-VEGF antibody is bevacizumab or ranibizumab.

In some other aspects, other therapeutic agents useful for combination tumor therapy with the antibody of the invention include antagonist of other factors that are involved in tumor growth, such as EGFR, ErbB2 (also known as Her2) ErbB3, ErbB4, or TNF. Preferably, the anti-NRP1 antibody of the invention can be used in combination with small molecule receptor tyrosine kinase inhibitors (RTKIs) that target one or more tyrosine kinase receptors such as VEGF receptors, FGF receptors, EGF receptors and PDGF receptors. Many therapeutic small molecule RTKIs are known in the art, including, but are not limited to, vatalanib (PTK787), erlotinib (TARCEVA®), OSI-7904, ZD6474 (ZACTIMA®), ZD6126 (ANG453), ZD1839, sunitinib (SUTENT®), semaxanib (SU5416), AMG706, AG013736, Imatinib (GLEEVEC®), MLN-518, CEP-701, PKC-412, Lapatinib (GSK572016), VELCADE®, AZD2171, sorafenib (NEXAVAR®), XL880, and CHIR-265.

The anti-Nrp antibody of the invention, either alone or in combination with a second therpateutic agent (such as an anti-VEGF antibody) can be further used in combination with one or more chemotherapeutic agents. A variety of chemotherapeutic agents may be used in the combined treatment methods of the invention. An exemplary and non-limiting list of chemotherapeutic agents contemplated is provided herein under "Definition".

When the anti-Nrp antibody is co-administered with a second therapeutic agent, the second therapeutic agent may be administered first, followed by the anti-Nrp antibody. However, simultaneous administration or administration of the anti-Nrp antibody first is also contemplated. Suitable dosages for the second therapeutic agent are those presently used and may be lowered due to the combined action (synergy) of the agent and anti-Nrp antibody.

For the prevention or treatment of disease, the appropriate dosage of antibody will depend on the type of disease to be treated, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 μg/kg to 50 mg/kg (e.g. 0.1-20 mg/kg) of antibody is an initial candidate dosage for administration to the patient, whether, for example, by one or more separate administrations, or by continuous infusion. A typical daily dosage might range from about 1 μg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. In a preferred aspect, the antibody of the invention is administered every two to three weeks, at a dose ranged from about 5 mg/kg to about 15 mg/kg. More preferably, such dosing regimen is used in combination with a chemotherapy regimen as the first line therapy for treating metastatic colorectal cancer. In some aspects, the chemotherapy regimen involves the traditional high-dose intermittent administration. In some other aspects, the chemotherapeutic agents are administered using smaller and more frequent doses without scheduled breaks ("metronomic chemotherapy"). The progress of the therapy of the invention is easily monitored by conventional techniques and assays.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat a disease or disorder. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages. Generally, alleviation or treatment of a disease or disorder involves the lessening of one or more symptoms or medical problems associated with the disease or disorder. In the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. In some embodiments, a composition of this invention can be used to prevent the onset or reoccurrence of the disease or disorder in a subject or mammal.

The following examples are intended merely to illustrate the practice of the present invention and are not provided by way of limitation. The disclosures of all patent and scientific literatures cited herein are expressly incorporated in their entirety by reference.

EXAMPLES

Example 1

Generation and Characterization of Anti-Nrp2$^B$ Antibodies

Anti-Nrp2$^B$ was isolated from human synthetic antibody phage libraries as previously described (Lee et al., *J Mol Biol*

340, 1073-1093 (2004)). In brief, phage-displayed synthetic antibody libraries were built on a single human framework by introducing synthetic diversity at solvent-exposed positions within the heavy chain complementarity-determining regions (CDRs). To improve library performance, monovalent and bivalent antigen-binding fragment (Fab) libraries were constructed, and explored different CDR-H3 diversities by varying the amino acid composition and CDR length. The library was then expanded by increasing the variability of CDR-H3 length and using tailored codons that mimicked the amino acid composition of natural CDR-H3 sequences. Using these libraries with completely synthetic CDRs displayed on a single scaffold high affinity antibodies were generated. For further details of strategies and methods for generating synthetic antibody libraries with single template, see, for example, WO03/102157 published Dec. 11, 2003, the entire disclosure of which is expressly incorporated herein by reference.

The selection procedures for anti-Nrp clones consisted of various combinations of solid-supported and solution-binding sortings that are known in the art. In solid-supported sortings, the antibody phage library was panned with target antigen coated on NUNC 96-well Maxisorp immunoplate at concentration of 5 ug/ml. In solution-binding sorting method, phage library was incubated with decreasing concentration of biotinylated antigen in solution, which then was captured by neutravidin coated on the 96-well Maxisorp plate (2-5 μg/ml). Decreasing concentration allowed more stringency in panning to fish for tighter binders.

As the result of combining solid-supported and solution-binding sortings, one clone from a $V_H$ Library (YW68.4) and another from a $V_H V_L$ Library (YW126.20), were identified as NRP-2 binders. A series of in vitro assays were conducted to examine properties and activities of the selected novel anti-NRP antibodies, including binding affinity assays (such as BIAcore) and blocking assays (such as Semaphorin induced growth cone collapse assay and HUVEC assays).

The CDRs of naïve clones were engineered to improve its affinity and stability and anti-Nrp2 antibodies YW68.4.2 and YW68.4.2.36 were generated. CHO cells expressed mNrp2 (a1a2b1b2)-His, hNrp2 (a1a2b1b2)-Fc fusion protein, and insect cells expressed hNrp2 (b1b2) were used for antibody screening and characterization. The $V_L$ and $V_H$ regions of anti-Nrp2$^B$ phage antibody (originally designated YW68.4.2.36) were cloned into mammalian expression vector respectively. Anti-Nrp2$^B$ human IgG1 or mIgG2a was expressed in mammalian CHO cells and purified with protein A affinity column.

The amino acid sequences of anti-Nrp2$^B$ antibodies YW68.4.2, and YW68.4.2.36 are shown in FIG. 10. The amino acid sequence of anti-Nrp2$^A$ antibody YW126.20 is shown in FIG. 11. The alignment of the light chain variable domain sequence of anti-Nrp2$^A$ antibody YW126.20 with human κ1 sequence is shown in FIG. 12. The alignment of anti-Nrp2$^A$ antibody YW126.20 heavy chain variable domain sequence with human III (hum III) sequence is shown in FIG. 13.

Figure 1A:
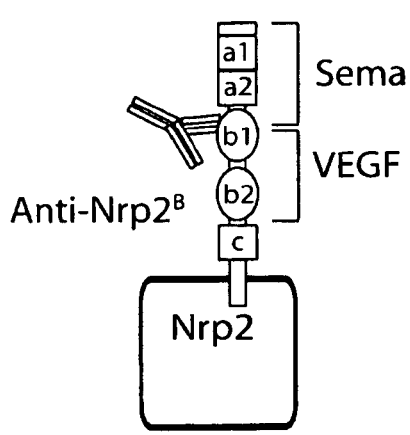
FIG. 1. Characterization of Anti-Nrp2$^B$ mAb. (A) Schematic representation of Sema and VEGF binding regions on Nrp2 relative to Anti-Nrp2$^B$ epitope regions. (B) ELISA assay demonstrating binding of Anti-Nrp2$^B$ to hNrp2 ECD (filled squares) and B1-B2 domains of hNrp2 (filled circles), but not hNrp1 ECD (open squares) or the A1-A2 domains of hNrp2 (open circles). (C) Blocking of VEGFC binding to Nrp2 by Anti-Nrp2$^B$. Increasing amounts of mAb was pre-incubated with plates coated with human Nrp2 ECD (5 µg/ml) for 1-2 hrs, followed by adding pre-titrated biotinylated human VEGFC (1 nM) for 15 min. The percentage of bound VEGFC was detected by streptavidin-HRP conjugates. (D) Blocking of VEGF$_{165}$ binding to Nrp2 by Anti-Nrp2$^B$. (E) Blocking of Sema3F binding to LECs. LEC were incubated with conditioned media containing Sema3F fused to alkaline phosphatase (AP) (REF), in the presence or absence of Anti-Nrp2$^B$. AP activity derived form bound Sema3F-AP was detected colorimetrically with same development times. No binding was observed with AP (left panel). Anti-Nrp2$^B$ did not block Sema3F binding to LECs (middle panels). Nrp2 ECD was used as a positive control for blocking binding (right panel). Scale bar FIG. 2. Anti-Nrp2$^B$ reduces VEGFC-induced function in vitro and in vivo. (A) Representative images of stained LECs migrating in response to 200 ng/ml of VEGFC for 18 hours in the presence or absence of Anti-Nrp2$^B$ (50 µg/ml) or VEGFR3 ECD (50 µg/ml). (B) Quantification of LEC migration in response to 200 ng/ml VEGFC (n=6 for each condition). (C) Quantification of LEC migration in response to 10 ng/ml VEGF$_{165}$ in the presence or absence of Anti-Nrp2$^B$ (50 μg/ml) or VEGFR3 ECD (50 μg/ml). N=6 for each condition. (D) Quantification of the pixel counts from a corneal micropocket assay described in (E). *p<0.05 (E) Representative images of LYVE-1 stained cornea, illustrating the effects of intracorneal placement of 150 ng pellet of VEGFC (P) and systemic treatment with Anti-Nrp2$^B$ (10 mg/kg twice weekly) or VEGFR3 ECD (25 mg/kg twice weekly). LYVE-1 staining has been pseudocolored red to facilitate visualization. *p<0.05; Error bars represent standard error of the mean.
Figure 1B:
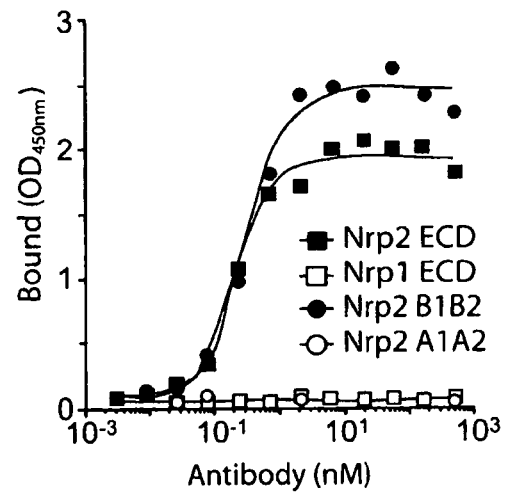
Figure 1C:
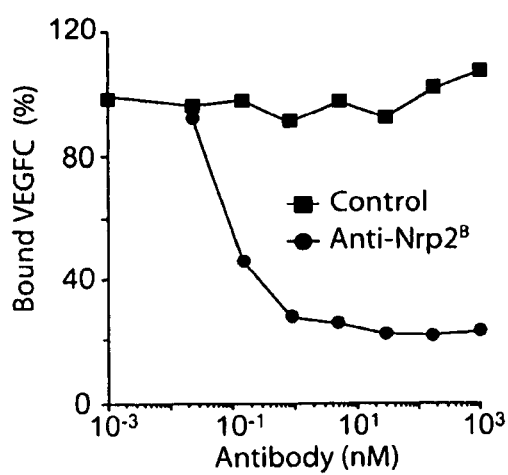
Figure 1D:
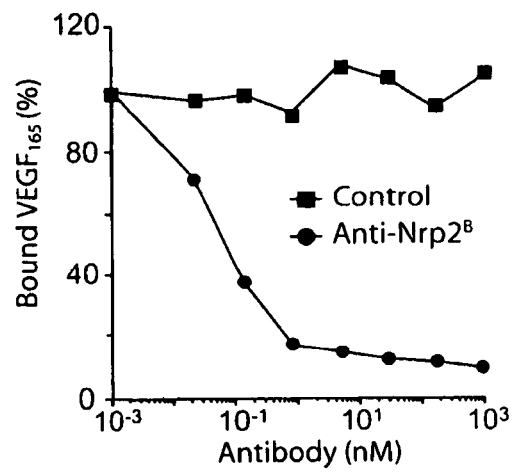
Figure 1E:
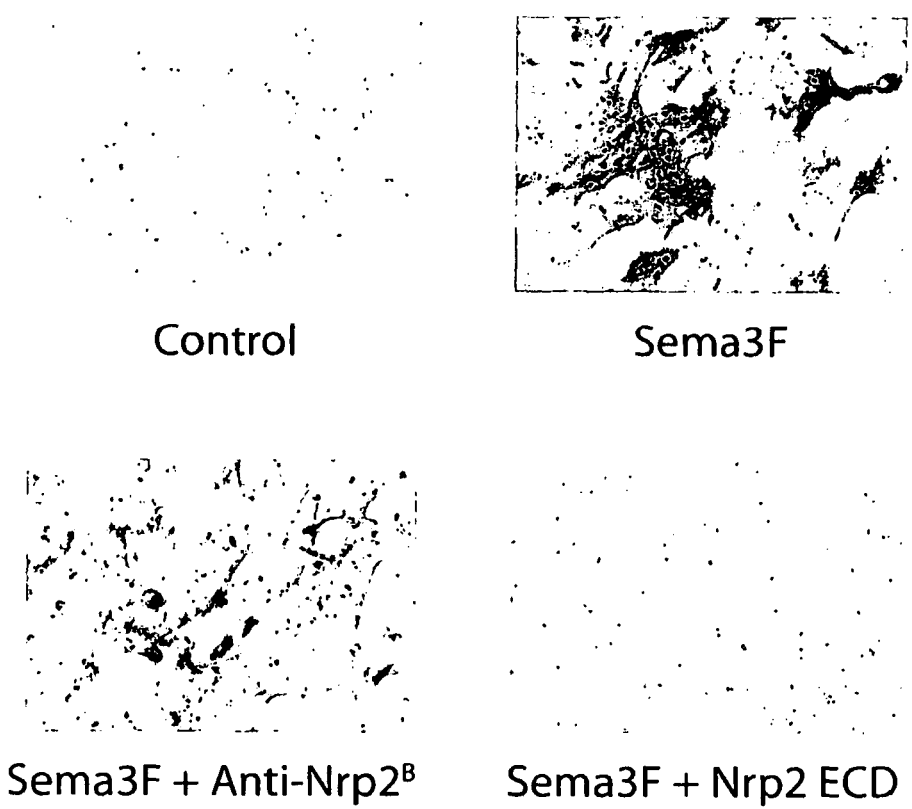

In the following experiments, anti-Nrp2$^B$ antibody YW68.4.2.36 was used, which will be hereinafter referred to as Anti-Nrp2$^B$. This antibody was targeted to the coagulation V/VII factor (b1-b2) domains of Nrp2 (FIG. 1A), as these domains are required for VEGFC binding to neuropilins (Karpanen et al., Faseb J 20, 1462-1472 (2006)). In addition, this antibody binds with similar Affinity to murine and human Nrp2 but does not bind Nrp 1 (FIG. 1B). It has been confirmed that anti-Nrp2$^B$ bids exclusively to the b1-b2 domains and does nto bind t th CUB (a1-a2) domains of human Nrp2, which are primarily responsible for semaphorin binding (Chen et al., Neuron 21, 1283-1290 (1998); Giger et al., Neuron 21, 1079-1092 (1998)).

To determine binding affinities of anti-Nrp2$^B$ IgG1 antibodies, surface plasmon resonance (SRP) measurement with a BIAcore™-3000 instrument was used. First of all, anti-Nrp2$^B$ human IgGs were captured by CM5 biosensor chips coated rabbit anti-human IgG to achieve approximately 200 response units (RU). For kinetics measurements, two-fold serial dilutions of mouse or human Nrp2 (a1a2b1b2) (0.5 nM to 250 nM) were injected separately in PBT buffer (PBS with 0.05% (v/v) Tween 20) at 25° C. with a flow rate of 30 μl/min. Association rates ($k_{on}$) and dissociation rates ($k_{off}$) were calculated using a simple one-to-one Langmuir binding model (BIAcore Evaluation Software version 3.2). The equilibrium dissociation constant ($K_D$) was calculated as the ratio $k_{off}/k_{on}$.

Anti-Nrp2$^B$ binds murine Nrp with a $K_d$ of 4.9 nM and to human Nrp2 with a $K_d$ of 5.3 nM as assessed by surface plasmon resonance measurement.

The ability of Anti-Nrpe to block binding of VEGFC to Nrp2 was tested in both ELISA format and in cell-based binding assays.

For ELISA-based binding specificity tests, three-fold serial dilutions of Anti-Nrp2$^B$ IgGs (0.002 nM to 500 nM) in PBST buffer (PBT buffer with 0.5% (w/v) BSA) were incubated with 1 μg/ml antigen-coated 96-well Maxisorp plates for at least 1 hr, and the plates were washed with PBT buffer. Bound antibodies were detected with anti-human antibody HRP conjugates diluted 1:2500 in PBST buffer, developed with TMB substrate for approximately 5 minutes, quenched with 1M $H_3PO_4$, and read spectrophotometrically at 450 nm.

To evaluate blocking Nrp2 from binding VEGF, three-fold serial dilutions of anti-Nrp2$^B$ IgGs were first incubated with 96-well Maxisorp plate coated NRP2-Fc (5 μg/ml) in PBST buffer for 2 hr, following by adding biotinylated VEGF$_{165}$ or VEGFC (full length) for 15 minutes. The amount of biotinylated VEGF binding to Nrp2 was detected by streptavidin-HRP conjugates.

To assess cellular binding, biotinylated VEGF$_{165}$ or VEGFC binding to LECs was carried out as previously described (Jia et al., J Biol Chem 281, 13493-13502 (2006)) and binding detected by streptavidin-alkaline phosphatase conjugates. Sema3F binding was performed as previously described (Chen et al., 1998, supra).

Anti-Nrp2$^B$ strongly blocked VEGFC binding to Nrp2 (FIG. 1C) and HEK-293 cells transfected with full length Nrp2. As Nrp2 can also bind VEGF (Gluzman-Poltorak et al., J Biol Chem 275, 29922 (2000)), likely utilizing the same domains, the ability of anti-Nrp2$^B$ to block VEGF$_{165}$ binding to Nrp2 was also tested. Anti-Nrp2$^B$ also strongly blocks VEGF$_{165}$ binding to Nrp2 (FIG. 1D) with a similar IC$_{50}$ (0.1 nM). However, Anti-Nrp2$^B$ was not able to block binding of Sema3F to LECs (FIG. 1$^E$) wich strongly express Nrp2 (FIG. 14). These results are consistent with previous observations that the a1-a2 domains are primarily responsible for semaphorin binding and the b1-b2 domains for VEGF binding (FIG. 1A).

Example 2

Anti-Nrp2$^B$ Blocks Selective VEGFC-Mediated Functions In Vitro

Materials and Methods

Cell Cultures

HMVEC-dLyAd—Human Dermal Lymphatic Microvascular Endothelial Cells (LECs) and HUVECS were purchased from Cambrex and cultured in EGM-2 medium (Cambrex). C6 LacZ cells were purchased from ATCC. 66C14 were a kind gift from Dr. Fred R Miller. Tumor cells were cultured in DMEM (Gibco) supplemented with 10% FBS. All cells were maintained at 37° C. in a 5% $CO_2$, 95% humidity incubator.

Cell Proliferation Assay

A 96-well black-clear bottom plate (VWR) was coated with 5 µg/ml Fibronectin (Invitrogen) at 37° C. for 2 hours. LEC's were harvested and resuspended in assay medium (0.1% BSA, EGM-2) 3000 cells/100 ul and added to wells. Cells were incubated at 37° C. for 16 hours. BrdU labeling solution (Cell Proliferation ELISA kit; Roche) was added and the cells were incubated for a further 24 hours at 37° C. BrdU incorporation was determined by chemiluminescence immunoassay. (6 wells per condition).

Results

Figure 2D:
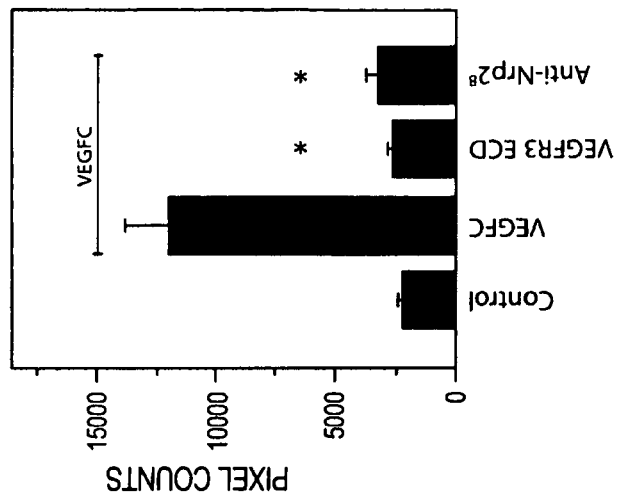
Figure 2C:
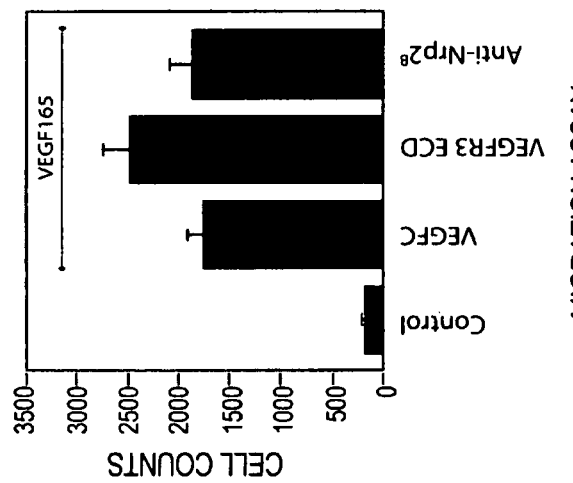
Figure 2B:
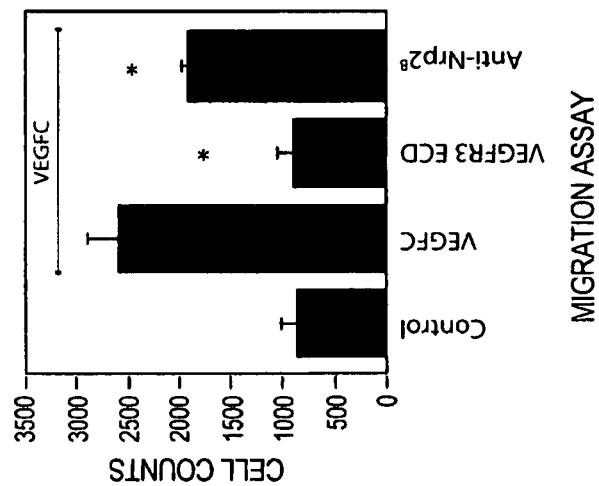

The role of Nrp2 in VEGFC mediated migration and proliferation was examined. These are key cellular activities induced by VEGFC (Joukov et al., *Embo J* 16, 3898-3911 (1997)). LECs have been previously shown to be highly responsive to VEGFC (Makinen et al., *Embo J* 20, 4762-4773 (2001); Veikkola et al., *Faseb* 17, 2006-2013 (2003); Whitehurst et al., *Lymphat Res Biol* 4, 119-142 (2006)). Using a transwell system, human LECs were introduced into the top chamber while VEGFC was added to the bottom chamber to promote migration. LECs that migrated to the bottom were then fixed, stained (FIG. 2A) and quantified (FIG. 2B). VEGFR3 extracellular domain protein (ECD), comprising the first three (ligand binding) Ig domains of VEGFR3 was used as a positive control to block VEGFC driven migration in this and subsequent experiments (Makinen et al., *Nat Med* 7, 199-205 (2001)). To determine whether Nrp2 function was required for LEC migration, Anti-Nrp2$^B$ mAbs were added to cells in the top chamber immediately prior to the addition of VEGFC. Anti-Nrpf was able to significantly reduce VEGFC mediated LEC migration (FIGS. 2A, 2B; p=0.004). The level of inhibition was less than that seen with VEGFR3 ECD, which completely inhibited VEGFC mediated LEC migration (FIGS. 2A, 2B; p<0.001 versus control; p=0.002 versus Anti-Nrp2$^B$). Similar results were obtained using another VEGFC responsive primary cell line, HUVECs.

As Anti-Nrp2$^B$ also blocked $VEGF_{165}$ binding to Nrp2, the role of Nrp2 in modulating $VEGF_{165}$ mediated migration was evaluated. $VEGF_{165}$ strongly induced migration in LECs as previously described (Hirakawa et al., *Am J Pathol* 162, 575-586 (203); Hong et al., *Faseb J* 18, 1111-1113 (2004); Makinen et al., *Embo J* 20, 4762-4773 (2001); Veikkola et al., *Faseb J* 17, 2006-2013 (2003)). A cross-species reactive anti-VEGF antibody (B20.4.1) was used as a positive control to block this VEGF driven migration (Liang et al., *J Biol Chem* 281, 951-961 (2006)). Interestingly, Anti-Nrp2$^B$ did not have any effect on $VEGF_{165}$ mediated migration (FIG. 2C), possibly due to the presence of Nrp1 (FIG. 14). Blocking Nrp1 function utilizing the Anti-Nrp1 mAb, Anti-Nrp1$^B$ (Pan et al., *Cancer Cell* 11, 53-67 (2007)) dramatically reduced VEGF mediated migration, confirming this hypothesis (FIG. 15). Addition of both Anti-Nrp1$^B$ and Anti-Nrp2$^B$ did not result in any further inhibition of migration in comparison to the inhibition seen with Anti-Nrp1$^B$ alone (FIG. 15), indicating that Nrp2 does not play a role in $VEGF_{165}$ mediated migration.

Next, the effect of Anti-Nrp2$^B$ on VEGFC induced LEC proliferation was investigated. Remarkably, Anti-Nrp2$^B$ had no effect on LEC proliferation whereas VEGFR3 ECD provided a strong block (FIG. 16), in agreement with previous reports where Nrp2 siRNA failed to inhibit VEGFC induced proliferation in endothelial cells (Favier et al., *Blood* 108, 1243-1250 (2006)). Thus, Nrp2 appears to be important for VEGFC driven migration but not proliferation.

Then, the ability of Anti-Nrp2$^B$ to modulate semaphorin function was tested. We used the hippocampal neuronal growth cone collapse assay, which previously demonstrated that Nrp2 is required for Sema3F mediated retraction of the actin-rich structures (Pozas et al., 2001). Addition of Anti-Nrp2$^B$ did not have any effect on the semaphorin induced collapse while addition of either recombinant Nrp2 A1A2 domain or Nrp2 ECD inhibited this collapse completely (FIG. 17). This result is consistent with our previous observation that Anti-Nrp2$^B$ does not bind to the semaphoring binding region and does not interfere with Sema3F binding to Nrp2. Thus, Anti-Nrp2$^B$ acts to block specific aspects of Nrp2 function, inhibiting VEGFC but not VEGF or Sema3F mediated cellular responses.

Example 3

Anti-Nrp2$^B$ Blocks VEGFC-Mediated Lymphagiogenesis In Vivo

Materials and Methods

Mouse Corneal Miry Pocket Assay

Adult CD-1 mice (Charles-River) were anesthetized and a pocket of 2×3 mm were created 1 mm from the center of the cornea in the epithelium by micro-dissection as described previously (Polyerini et al., *Methods Enzymol* 198, 440-450 (1991)). Agents to be tested for lymphangiogenic activity were immobilized in an inert hydron pellet (2×2 mm). The pellet was then implanted into the base of the pocket. Animals were treated with control antibody (10 mg/kg), Anti-Nrp2$^B$ (10 mg/kg) or VEGFR3 ECD 25 mg/kg IP twice weekly for 2 weeks. Then animals were sacrificed and corneas dissected. The lymphatics were visualized by whole-mount IHC with anti-LYVE-1 antibody (R&D Systems 1:500). The corneas were photographed and LYVE-1 positive lymphatic vessels arising from the limbus were quantified.

Mouse Skin Vessel Permeability Assay

The backs and flanks of adult C57BL6J female mice were shaved and divided into 4 teat areas. They were then injected i.v. with 150 µl 0.5% Evan's blue solution. 1 hr after the Evan's blue injection, 20 µl of PBS containing BSA or hVEGF (7.5 µg/ml) with or without antibody (0.5 mg/ml) was injected intra dermally, randomly on one of the four zones. 1 hr later, the animals were sacrificed and the skin was dissected out and imaged. Skin samples for each injection zone were cut out and incubated in formamide solution at 55° C. for 48 hrs to extract the blue dye. The absorbance of the solution was then measured with a spectrometer at 600 nm.

Results

Figure 2E:
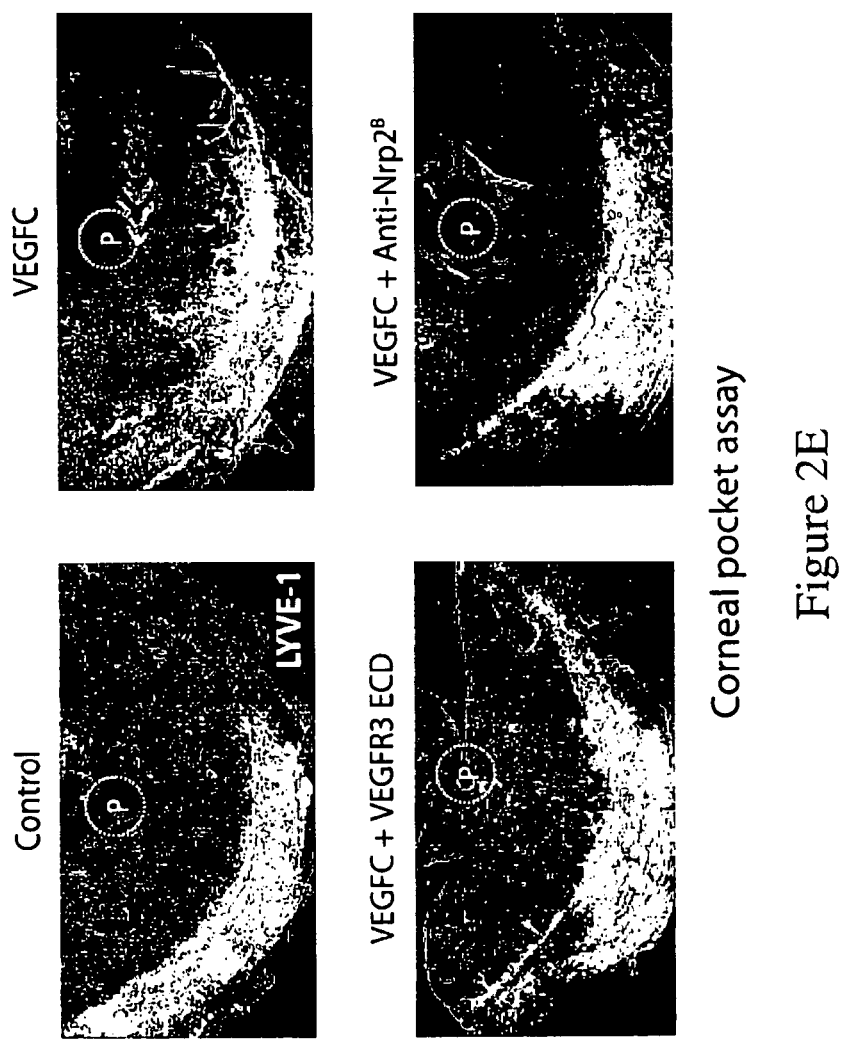

Having observed a significant reduction in LEC migration by blocking Nrp2 in vitro, it was next examined whether Nrp2 was required for modulating VEGFC function in vivo. We studied two well-characterized VEGFC mediated in vivo activities—adult lymphangiogenesis and vascular permeability (Cao et al., *Circ Res* 94, 664-670 (2004); Joukov et al., *J Biol Chem* 273, 6599-6602 (1998); Kubo et al., *Proc Natl Acad Sci USA* 99, 8868-8873 (2002); Saaristo et al., *Faseb J* 16, 1041-1049 (2002)). To study lymphangiogenesis, the murine corneal micropocket assay (Kubo et al., 2002, supra) was utilized. In this assay, a pellet of VEGFC was introduced into the avascular cornea of an adult mouse. Over 14 days, in response to the VEGFC, a dense plexus of lymphatic vessels grew into the cornea from the limbus (FIG. 2E; 12,000 pixels$^2$ with VEGFC treatment versus 2284 pixels$^2$ in control). These vessels were labeled by LYVE-1 immunohistochemistry (IHC) and subsequently quantified (FIG. 2D). Systemic administration of VEGFR3 ECD almost completely blocked this VEGFC induced lymphangiogenesis (2671 pixels$^2$; p<0.001). Anti-Nrp2$^B$ also effectively blocked the corneal lymphangiogenic response (3281 pixels$^2$; p<0.001). This block was similar in degree to the block observed using VEGFR3 ECD (FIGS. 2E, 2D; p=0.67).

In order to evaluate vascular permeability, the miles assay (Brkovic and Sirois, *J Cell Biochem* 100, 727-37 (2007); Eriksson et al., *Circulation* 107, 532-1538 (2003)) was used. This assay uses intradermal injection of VEGFC to induce vascular permeability and intravascular injection of Evans blue dye as a tracer to detect and quantify permeability in cutaneous vessels (FIG. 16). Remarkably, treatment with Anti-Nrp2$^B$ had no effect on VEGFC induced permeability, in contrast to the block observed with VEGFR3 ECD treatment (p=0.038). These results demonstrate that, consistent with what we observe in vitro, Nrp2 appears to be important for selective VEGFC mediated functions in vivo.

Example 4

Anti-Nrp2$^B$ Modulates VEGFC Function by Inhibiting Nrp2/VEGF Receptor Complex Formation Materials and Methods Cell Migration Assay Migration assays were performed using a modified Boyden chamber with 8 µM pore size Falcon 24-multiwell insert system (BD Biosciences). The plates were coated with 5 ug/ml Fibronectin (Invitrogen) for 2 hours at 37° C. Cells in 100 µl assay medium (0.1% BSA, EGM-2) with/without antibodies were added to the upper chamber. Chemoattractant was added to the lower chamber in 500 µl assay medium, and cells were incubated at 37° C. for 16 hours. Cells on the upper membrane were removed with a sponge swab and cells on the lower surface were fixed in 70% ethanol and stained with Sytox green (Molecular Probes). Images were taken of the entire lower surface of the well, and number of migrated cells counted. (6 wells per condition).

FACS Analysis

Confluent LECs were incubated with control Anti-Nrp2$^B$ antibodies (10 µg/ml) for 5 min, 2 hrs or 20 hrs at 37° C. Cells were harvested with enzyme free cell dissociation buffer (Gibco), and incubated with biotinylated antibody at 1:100 in FACS buffer (PBS, 2% FBS, 2 mM EDTA, 0.1% sodium azide) containing 5% normal mouse serum, 2% normal rat serum and 10% 10 µg/ml human IgG. Antibodies were biotinylated using the FluoReporter mini-biotin-xx protein labeling kit (Molecular Probes). Cells were then washed with FACS buffer and stained with streptavidin-PE (BD Biosciences). Data was analyzed with the FacsCalibur system (BD Biosciences).

Cell Adhesion Assay

Subconfluent LECs were pre-incubated in 100 µl Medium 199 with control or Anti-Nrp2$^B$ antibodies (10 µg/ml) for 30 min at 37° C., then plated into NUNC maxisorp flat bottom 96-well plates (eBioscience) coated with 1 µg/ml Fibronectin (Roche) at 10,000 cells per well. Plates were centrifuged for 1 min at 140 g to synchronize contract of cells with substrate, and incubated at 37° C. for 30 min. Plates were then washed 3 times with PBS, and frozen at −80° C. Cell density was determined with the CyQuant kit (Molecular Probes).

VEGF Receptor Signaling Assays

Confluent HUVECs were stimulated for 10 minutes with 200 ng/ml of VEGFC in the presence or absence of control or Anti-Nrp2$^B$ antibodies. The cells were lysed and assayed for many mediators know to play a role if VEGF receptor signaling. VEGFR2 activation was evaluated using total VEGFR2 and phospho-VEGFR2 ELISA assays (DuoSet IC ELISA kit, R&D). VEGFR3 activation was evaluated using a kinase receptor activation assay (KIRA) with an VEGFR3-293 cell line as previously described (Sadick et al., *J Pharm Biomed Anal* 19, 883-891 (1999)). Briefly, stable 293 cell lines expressing full length Flag tagged human hVEGFR3 were assayed for receptor phosphorylation following stimulation. $5 \times 10^4$ cells were starved overnight (DMEM with 0.1% BSA) and then stimulated with 40 ng/ml VEGFA (Genentech South San Francisco, Calif.) or 200 ng/ml VEGFC (Genentech South San Francisco, Calif.) for 8 minutes. Cells were lysed in PBS containing 1% triton and sodium orthovanadate. ELISA plates were coated with capture Flag antibody (Sigma St Louis, Mo.). The plates were coated (PBS+1 ug/ml of antibody) overnight and blocked (PBS+0.5% BSA) for 1 hr. After 3 washes (PBS+0.05% Tween 20), lysates were added for 2 hours, washed three times, followed by addition of phospho-detection antibody 4G10 (Upstate Lake Placed, N.Y.) for 2 hours. Detection was performed with HRP antibody (Amersham Piscataway, N.J.) and TMB substrate. Plates were read at 450 nm. Total AKT, phospho-AKT, total Erk1/2, phospho-Erk1/2, total Src, phospho-Src, total p38 MAPK and phospho-p38 MAPK were evaluated using sandwich ELISA kits from BioSource.

Results

The finding that Anti-Nrp2$^B$ interferes with VEGFC actions was consistent with the fact that it blocks VEGFC binding to Nrp2. In addition, the fact that it blocks only selective functions both in vitro and in vivo was highly unexpected. One possible explanation of why a disruption of LEC migration and lymphangiogenesis but not LEC proliferation or vascular permeability was observed is that Anti-Nrp2$^B$ may generally inhibit migration, possibly by disrupting LEC adhesion to the extracellular matrix. To test this, the effect of Anti-Nrp2$^B$ on migration induced by a number of LEC motogens was evaluated. Anti-Nrp2$^B$ did not have any effect on migration induced by VEGF (FIG. 2C), HGF (FIG. 3B) or FGF. Therefore Anti-Nrp2$^B$ did not generally disrupt LEC migration. Furthermore, Anti-Nrp2$^B$ did not have any effect on LEC adhesion to fibronectin or collagen, two extracellular matrix substrates.

Figure 3A:
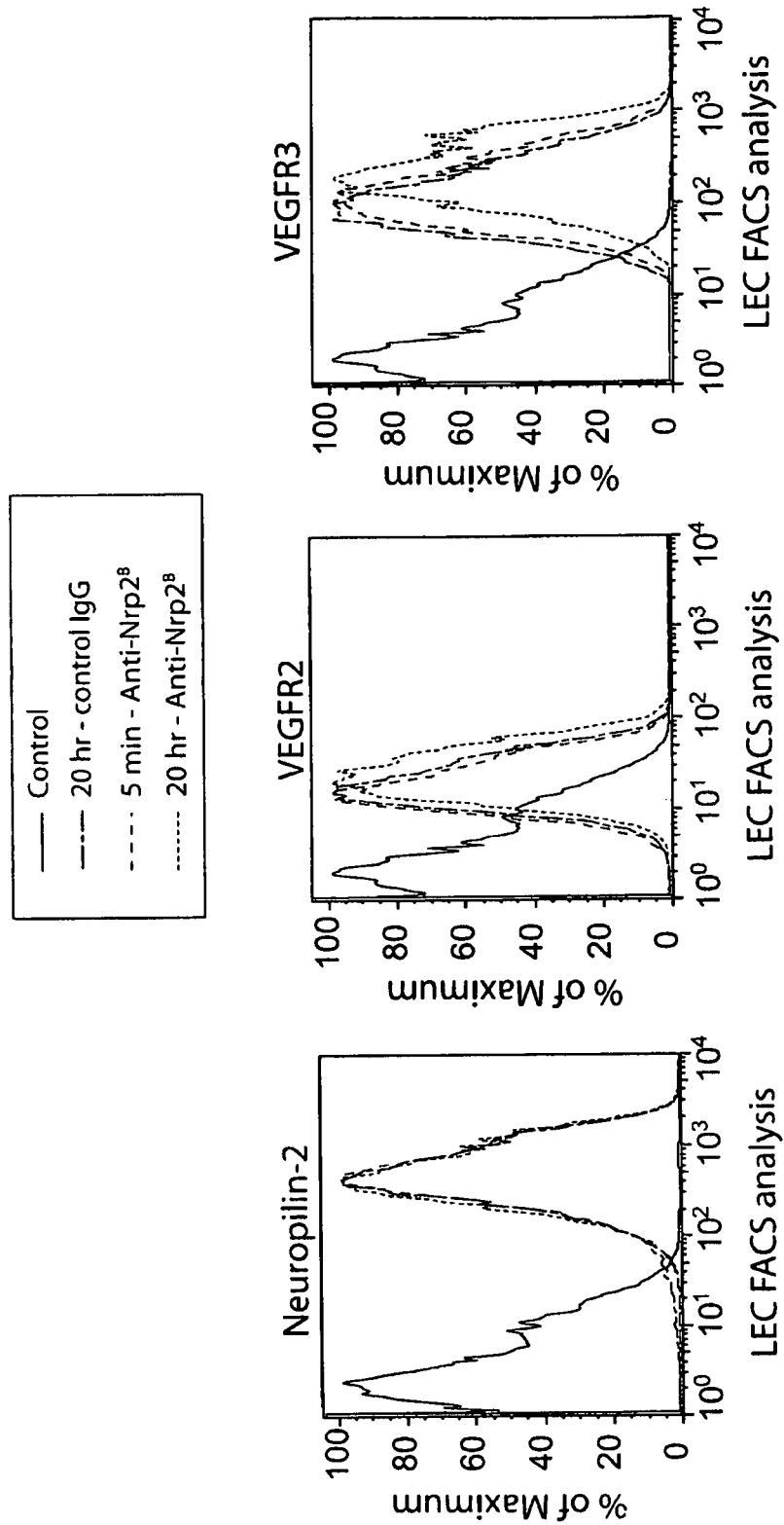
FIG. 3. Nrp2$^B$ treatment results in a reduction in VEGF receptor activation and inhibits Nrp2/VEGF receptor complex formation. (A) FACS analysis of Nrp2, VEGFR2 ad VEGFR3 levels on the surface of LEC after treatment with control antibody (10 μg/ml; green line) or Anti-Nrp2$^B$ (10 μg/ml) for 5 minutes (blue line), or 20 hours (red line). (B) Quantification of LEC migration in response to 20 ng/ml HGF in the presence or absence of Anti-Nrp2$^B$ (50 μg/ml) or VEGFR3 ECD (50 μg/ml). N=6 for each condition. (C) VEGFR2 phosphorylation level in LECs detected by ELISA assay using antibodies that recognized total or tyrosine-phosphorylated VEGFR2. VEGFC (concentration as noted) was added for 10 min in the presence or absence of Anti-Nrp2$^B$ (10 μg/ml) or VEGFR3 ECD (10 μg/ml) to induce the phosphorylation of VEGFR2, n=3 for each condition. VEGFR2 phosphorylation level in anti-Nrp2$^B$ (10 μg/ml) treated cells was significantly different from the VEGFC stimulation at 200 ng/ml and consistently lay between the phosphorylation level induced by 175 ng/nl and 150 ng/ml of VEGFC. (D) Quantification of LEC migration in response to VEGFC (concentration as noted) in the presence or absence of Anti-Nrp2$^B$ (10 μg/ml) or VEGFR3 ECD (10 μg/ml). Significant reductions in migration were noted at 50 ng/ml of VEGFC or when blocked with VEGFR3 ECD. *p<0.05; Error bars represent the standard error of the mean. Each experiment was repeated a minimum of three times. (E) CO-IP FIG. 4. Nrp2 is expressed in the lymphatics of tumor bearing mice. (A-D) LYVE-1 staining (left column—red) labeling lymphatics, Nrp2 staining (middle column—green) and the overlay in the (A) intestine and (B) lymph node of normal adult mouse. Nrp2 signal does not co-localize with LYVE-1 labeled lymphatics in either organ. Rare Nrp2 staining inflammatory cells are present within the fibrostromal core of the intestinal villi and within the lymph node germinal centers (C) In lymph nodes from tumor bearing animals, Nrp2 signal does co-localize with LYVE-1 positive lymphatic vessels lining the LN sinuses. Additional Nrp2 staining inflammatory cells are also present. (D) Strong Nrp2 staining is also seen in lymphatic vessels within 66c14 tumors. (E) Weak membranous staining can be also seen on tumor cells. Seconday only stained controls did not show any signal. Boxed areas are shown at high magnification within insets. Scale bar * for A-C and  for D.
Figure 3B:
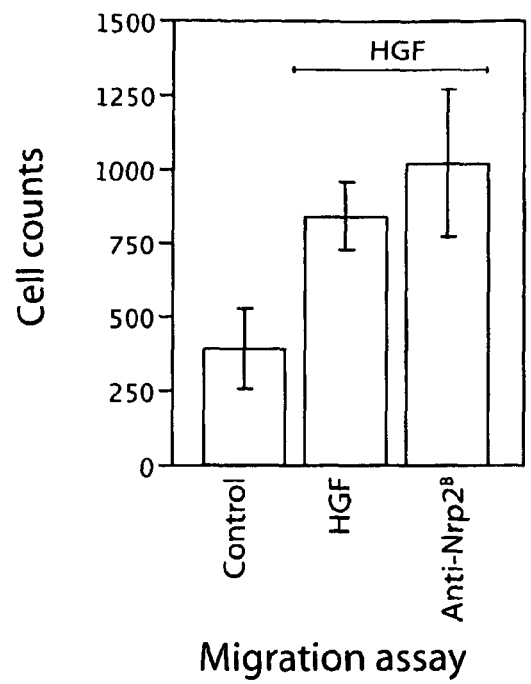

A second possibility is that the Anti-Nrp2$^B$ mAb may cause internalization of Nrp2 (Jaramillo et al., *Exp Cell Res* 312, 2778-2790 (2006)). As Nrp2 forms a complex with VEGFR3, even in the absence of ligand (Favier et al., 2006, supra; Karkkainen and Alitalo, *Semin Cell Dev Biol* 13, 9-18 (2002)), this could result in a selective co-internalization of VEGFR3, affecting specific VEGFC mediated functions. This possibility was further validated by the finding that VEGFC driven vascular permeability is mediated by VEGFR2 and not VEGFR3 (Joukov et al., 1998, supra). To address this possibility, LECs were incubated with Anti-Nrp2$^B$ at 37° C. for 5 minutes, 2 hours or 20 hours and then performed FACS analysis with antibodies against Nrp2, VEGFR2 and VEGFR3 to determine the level of the receptors on the cell surface. No difference was observed between treatments, suggesting that Anti-Nrp2$^B$ did not cause significant internalization of Nrp2, VEGFR2 or VEGFR3 (FIG. 3A).

Figure 3C:
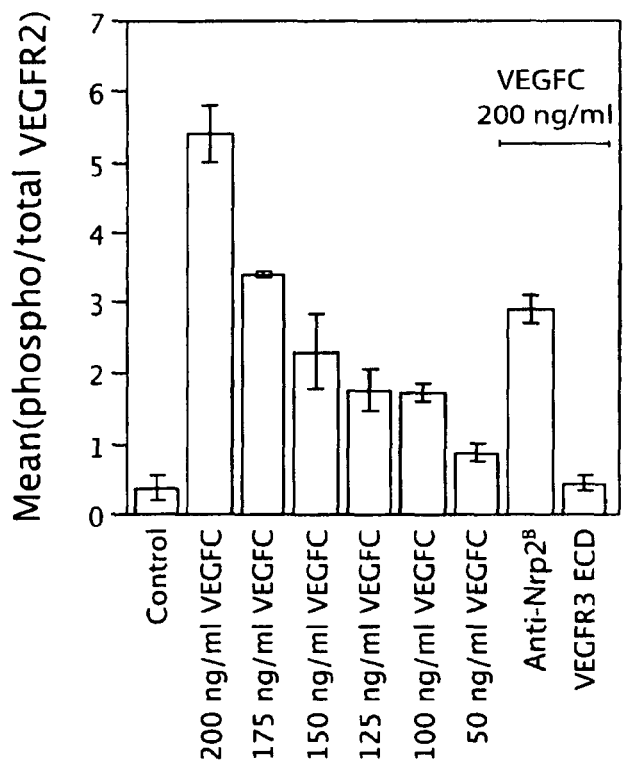
Figures 3D, 3E:
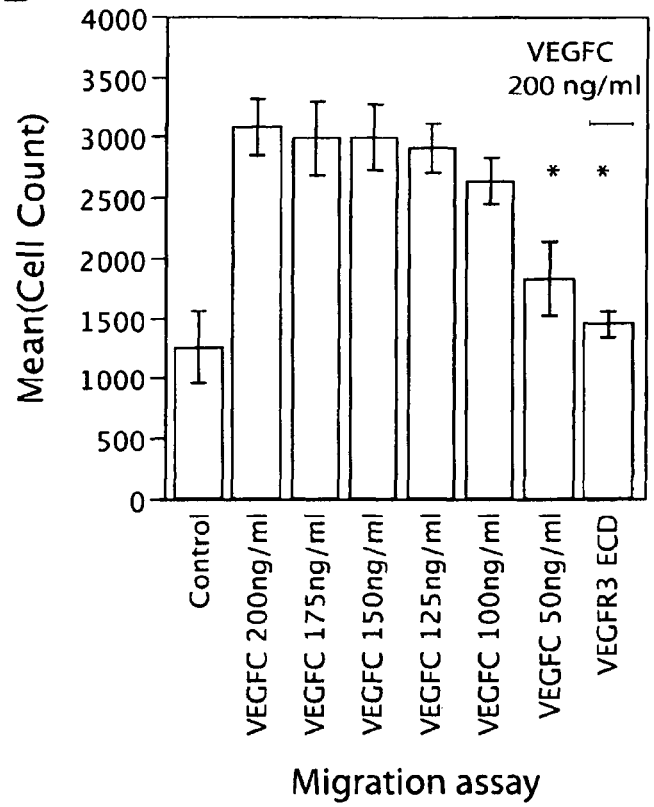

As Nrp2 has been proposed to augment VEGF receptor signaling (Favier et al., 2006, supra), next, the effect of Anti-Nrp2$^B$ on VEGFR2 and VEGFR3 activation was studied, where VEGFC stimulation leads to receptor dimerization and auto-phosphorylation. In agreement with the prior in vitro and in vivo data, VEGFR3 ECD completely blocked VEGFC mediated VEGFR2 (FIG. 3C; p<0.001) and VEGFR3 phosphorylation. Anti-Nrp2$^B$ treatment resulted in a reduction of VEGFR2 (FIG. 3C; p<0.001) and VEGFR3 activation, but to a significantly lesser degree than VEGFR3 ECD treatment (p<0.001). This observation raised the possibility that the selective inhibitory activity of Anti-Nrp2$^B$ could be a result of differential requirements of VEGF receptor activation for migration and proliferation, that migration requires higher levels of receptor activation than proliferation. To address this possibility, the dose response of VEGFR2 phosphorylation to VEGFC stimulation was evaluated (FIG. 3C). It was consistently observed that the reduction of VEGFR2 phosphorylation caused by Anti-Nrp2$^B$ treatment was equivalent to the VEGFR2 phosphorylation obtained by stimulating with 175 ng/ml or 150 ng/ml of VEGFC. Then, a dose response analysis of migration to VEGFC stimulation was performed (FIG. 3D). It has been noted that LECs stimulated with 175 ng/ml or 150 ng/ml of VEGFC migrated equivalently to cells stimulated with 200 ng/ml of VEGFC. Indeed, a significant reduction in migration was not observed till VEGFC levels were reduced to 50 ng/ml. We therefore reasoned that the reduction in VEGFR2 phosphorylation induced by Anti-Nrp2$^B$ was, by itself, insufficient to reduce migration.

We additionally evaluated the effect of Anti-Nrp2$^B$ on downstream signaling events mediated by VEGF receptors. Treatment with Anti-Nrp2$^B$ or stimulation with 175 ng/ml or 150 ng/ml of VEGFC did not significantly reduce Erk1/2, Akt or p38 MAPK activation which modulate VEGFR2 mediated proliferation, permeability and motility respectively, similar to what is observed with Nrp1 (Pan et al., 2007). This indicated that Nrp2 might regulate LEC migration and lymphangiogenesis by a mechanism other than enhancing VEGF receptor activation or downstream signaling.

Lastly, we the effect of Anti-Nrp2$^B$ on Nrp2/VEGF receptor complex formation was tested. As reported previously, Nrp2 can be coimmunoprecipitated with VEGFR2 and VEGFR3 in the presence or absence of VEGFC (Favier et al., 2006 supra; Karpanen et al., 2006, supra) (FIG. 3E). This interaction was dramatically reduced by Anti-Nrp2$^B$ (FIG. 3E). This result suggests that the Nrp2/VEGF receptor complex is important for specific VEGFC mediated functions. Furthermore, the role of Nrp2 is not exclusively to enhance VEGF receptor signaling in response to ligand stimulation.

Example 5

Nrp2 is Expressed in Tumor-Associated Lymphatics

Materials and Methods
Immunohistochemistry

18 µm tissue sections were cut and mounted onto glass slides. The sections were incubated O/N with primary antibody (anti-NRP2$^B$ (1:500 control staining performed in E12.5 mouse spinal cord where expression has been well characterized), anti-LYVE-1 (anti-R&D, 1:200), anti-PECAM-1 (Benton Dickinson, 1:500), anti-PROX-1 (Chemicon, 1:1000), or Ki67 (Neovision 1:100) at 4° C. Samples were then stained with Alexa 488 or Alexa 568 secondary antibodies (1:200; Molecular Probes) for 4 hrs at RT. Staining with secondary only was used as a control. TUNNEL staining was performed with a commercial kit (Roche). Images were captured with a Zeiss Axiophot fluorescence microscope. Blood and lymphatic vessel area was determined from 6 representative images from each of 6 tumors per group, evaluated for mean pixel number by ImageJ.

Results

In order to determine if Nrp2 pays a role in adult lymphatic biology, the expression of Nrp2 in adult lymphatics was evaluated. Within the vascular system, Nrp2 expression has been previously described in veins and lymphatics (Herzog et al., *Mech Dev* 109, 115-119 (2001); Moyon et al., *Development* 128, 3359-3370 (2001); Yuan et al., *Development* 129, 4797-4806 (2002)). As described above, LEC in culture strongly express Nrp2 (FIG. 14). However, we were unable to detect Nrp2 by IHC in colonic, LYVE-1 positive lymphatic vessels of normal adult mice (FIG. 4A; for positive control staining see FIG. 17). The colon was evaluated, as it has a rich plexus of lymphatic vessels with a fairly stereotyped pattern. We were also unable to detect Nrp2 expression by IHC within lymphatic vessels of lymph nodes (FIG. 4B) and skin from normal adult mice. These results were confirmed by Nrp2 in situ hybridization (ISH). In contrast, strong Nrp2 expression was observed in LYVE-1+lymphatic vessels in lymph nodes adjacent to orthotopically or heterotopically transplanted tumors (FIG. 4C). This was observed with a number of tumor lines including the orthotopically transplanted murine breast adenocarcinoma line, 66c14 (Aslakson and Miller, *Cancer Res* 52, 1399-1405 (1992)) and the heterotopically transplanted rat glioblastoma line, C6 (data not sown). Nrp2 was also observed in peri-tumoral and intra-tumoral lymphatics (FIG. 4D) for a number of tumor lines including 66c14, C6 and PC3 (human prostate carcinoma line). This expression was confirmed by ISH in a subset of tumor types.

Example 6

Anti-Nrp2$^B$ Reduces Lung Metastasis in Multiple Tumor Models

Materials and Methods

All animal studies were in accordance with the Guide for the Care and Use of Laboratory Animals, published by the NIH(NIH Publication 85-23, revised 1985). An Institutional Animal Care and Use Committee (IACUC) approved all animal protocols.

Tumor Models

For 66C14, cells were harvested by trypsinization, washed, and resuspended in PBS at a concentration of 2×10$^5$ cells in 10 µl PBS. Mice were anesthetized using 75 mg/kg ketamine and 7.5 mg/kg xylazine, and an incision made underneath the right forelimb. 2×10$^5$ cells in 10 µl PBS was injected directly into the exposed 4$^{th}$ mammary fat pad of 6-8 week old female balb-C mice. For C6, 2×10$^6$ tumor cells in 100 µl PBS were injected subcutaneously into the right flank of 6-8 week old female balb-C nude mice. For both sets of studies, tumor growth was monitored 3 times weekly. When tumors reach an average size of 80-120 mm$^3$, mice were sorted to give nearly identical group mean tumor sizes, and treatment was started. This was considered day 1 of each study. Animals were treated with control antibody (10 mg/kg), Anti-Nrp2$^B$ (10 mg/kg) or VEGFR3 ECD 25 mg/kg IF twice weekly till study termination. All studies were repeated 3 times to ensure reproduceability.

At study end animals were anethetiszed and perfused with 4% PFA. Tumors were harvested, cryoprotected and frozen in OCT (Tissue-Tek). Lungs were inflated via a right ventricular perfusion of 10 ml of PBS followed by 4% PFA, and visual counts of metastatic lesions were performed prior to Micro-CT analysis.

SLN metastasis was evaluated by heterotopic implantation of C6 tumor cells into the ear. Briefly, a cohort of animals were pre-treated with control antibody (10 mg/kg) or Anti- Nrp2$^B$ (10 mg/kg), one day prior to tumor cell implantation, and twice weekly thereafter. 1×10$^5$ C6 lacZ Cells were injected subdermally into the ear of 70 female balb/c nude mice. Mice were sacrificed at day 3, 6, 9, 13 and 15, and sentinel lymph nodes identified by cutaneous lymphangiography and subsequently dissected out. Lymph nodes were homogenized and lysate assayed for β-galactosidase activity (Pierce).

Intradermal lymphangiography was performed on control and tumor bearing mice as follows. 2 µl of evans blue dye (3% by weight) containing 1% 20 nm polystyrene fluorescent microbeads (Molecular Probes) was injected intradermally at the apex of the tumor. Animals were allowed to recover for 2 hours and then sacrificed. Tumors were dissected out with care to not include peritumoral tissue. They were either fixed and then histochemically analyzed or incubated in formamide to extract evans blue and quantified with a OD600 measurement by spectrophotometer.

Micro-CT Analysis of Lungs

Lungs were immersed in 10% NBF for 24 hours, then immersed in a 20% solution of an iodine-based x-ray computed tomography contrast agent, Isovue370 (Bracco Diagnostics Inc, Princeton, N.J.), was diluted with PBS for 24 hours. Lungs were then immersed in and perfused via the trachea cannula with 20 mls of soy bean oil (Sigma-Aldrich, St. Louis, Mo.) at a rate of 0.25 mL/min. The soy bean oil was used to remove excess contrast agent and provide a background media for imaging.

The mouse lungs were imaged ex-vivo with a VivaCT (SCANCO Medical, Basserdorf, Switzerland) x-ray micro-computed tomography (micro-CT) system. A sagittal scout image, comparable with a conventional planar x-ray, was obtained to define the start and end point for the axial acquisition of a series of micro-CT image slices. The location and number of axial images were chosen to provide complete coverage of the lung. The lungs were immersed in soybean oil as the background media. The micro-CT images were generated by operating the x-ray tube at an energy level of 45 kV, a current of 160 µA and an integration time of 450 milliseconds. Axial images were obtained at an isotropic resolution of 21 µm. The lung tumor estimates (number and volume) were obtained by an semi-automated image analysis algorithm that includes an inspection step by a trained reader. Lung tumors appear as a hyper-intense solid mass relative to porous, mesh-like structures of the normal lung. This is due to the absorption of the iodine contrast agent by solid structures (bronchial and aveloi walls, tumors, trachea, medial steinum) contained within the lung, Excess contrast agent was cleared from the filled air spaces by the oil perfusion step. Potential tumor masses were extracted by a series of image processing steps. The image analysis software was developed in-house. It was written in C++ and employed the Analyze (AnalyzeDirect Inc., Lenexa, Kans., USA) image analysis software function libraries. The algorithm employs intensity thresholding, morphological filtering and region-growing to extract all potential tumors masses. An intensity threshold (1480 Hounsfield Units) was determined by histogram analysis of 5 arbitrary lungs employed for algorithm development and the optimal threshold was chosen to include tumor voxels and exclude any background signal. Morphological (erosion, dilation) and region-growing operations were applied to connect hyper-intense regions of voxels and to remove any voxels of similar density found in the thin walls of the bronchioles and aveoli. The region growing step requires a minimum volume of 2300 connected voxels (greater than 0.0231 mm$^3$) to be accepted as an object (mass). The identified objects were then evaluated by a trained reader with the Analyze 3D visualization software. Individual objects were accepted or rejected as possible tumors based on the appearance of the object and its location within the lung. Objects were rejected if they reside outside the lung (ex. mediasteinum, extraneous tissue debris) or resemble a blood-filled vessel. The tumor count, individual tumor volume and total tumor volume were determined for each lung. This analytic technique was validated with a well-established tumor metastasis model. Eleven animals with orthotopic transplantation of 4T1 breast mammary adenocarcinoma tumor cells were evaluated for lung metastasis by this micro-CT technique followed by serial histologic analysis of the lungs. Lung tumor volume estimates were highly correlated (r=0.9, p=0.0002) with histological estimates of tumor size (pixel count; FIG. 18).

Results

Figure 5A:
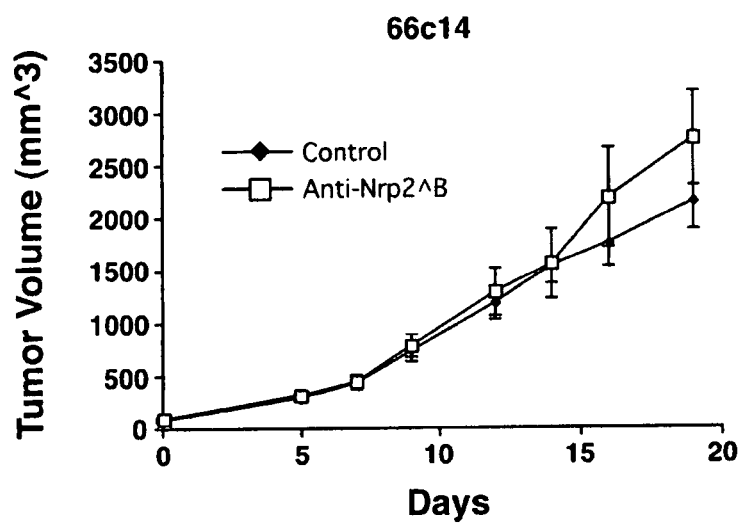
FIG. 5. Anti-Nrp2$^B$ treatment results in a reduction of lung metastasis in the 66c 14 tumor model. (A) Mean tumor volume graph of 66c 14 tumor model study analyzed below. Animals were dosed twice weekly i.p. with 10 mg/kg Anti-Nrp2$^B$ or control antibody once tumors reached an average size of 100 mm$^3$ and were dosed throughout the study. (B) Quantification by visual inspection of the number of metastatic nodules per lung in control and Anti-Nrp2$^B$ treated animals. (C) Representative images of lungs from control (left) and Anti-Nrp2$^B$ (right) treated animals. Lungs were inflated prior to fixation by right cardiac ventricular perfusion. Nodules are highlighted in white to facilitate visualization. (D, E) 3-dimensional renderings of representative micro-CT scanned lungs demonstrating metastatic nodules (red) in control (D) and Anti-Nrp2$^B$ (E) treated animals. The positions of the longitudinal section (top inset) and the cross section (bottom insert) are indicated by the black and red dotted lines respectively. This analysis confirms that most nodules are on the surface of lungs. (F) Quantification of the number of metastatic nodules per lung by Micro-CT analysis of the lungs. (G) FACS analysis of Nrp2 levels on the surface of in vitro cultured 66c 14 tumor cells. (H) H&E staining of a lung nodule demonstrating metastatic tumor cells. Error bars represent standard error of the mean. Scale bar * for C and  for H.
Figure 5B:
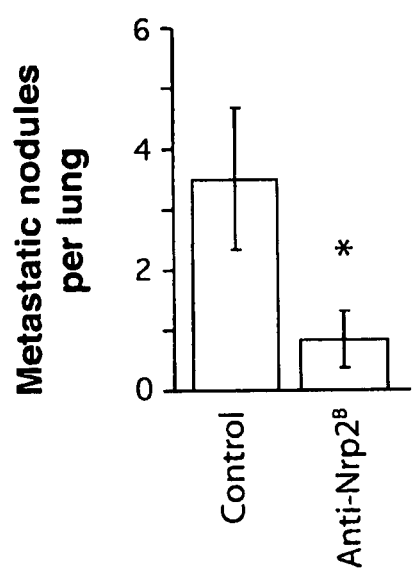
Figure 5C:
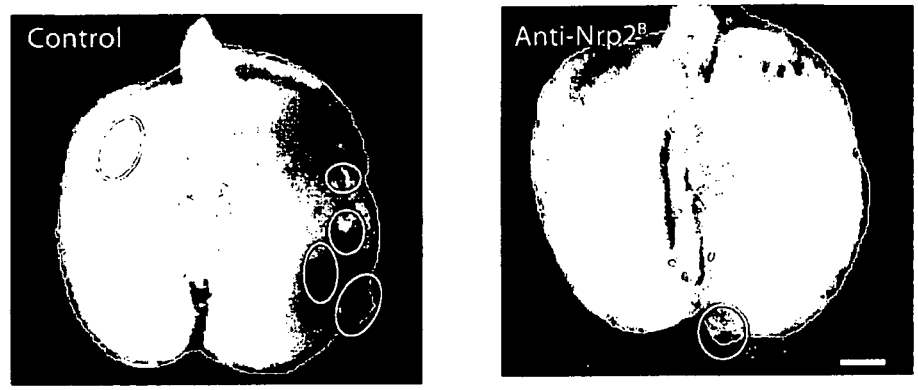
Figure 5D:
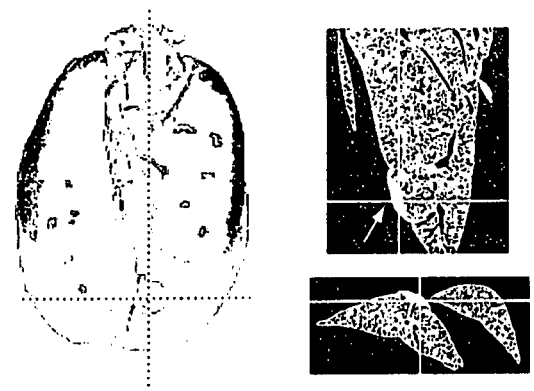
Figure 5E:
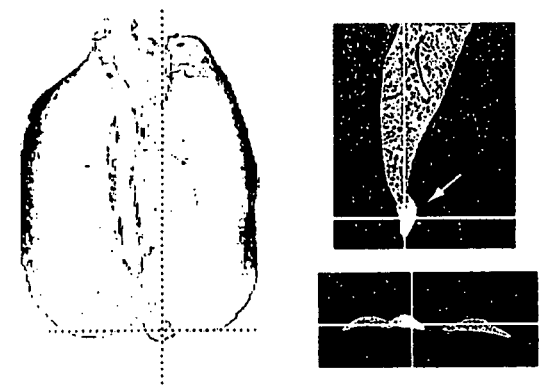
Figure 5F:
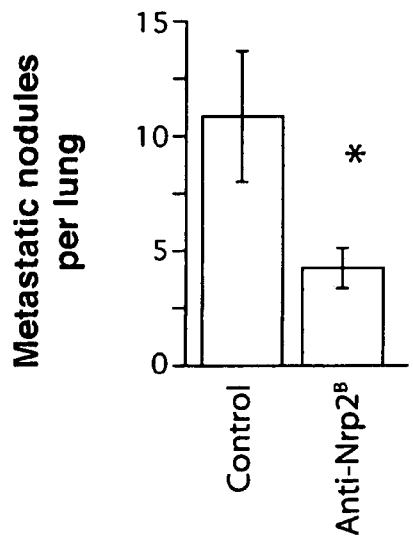
Figure 5G:
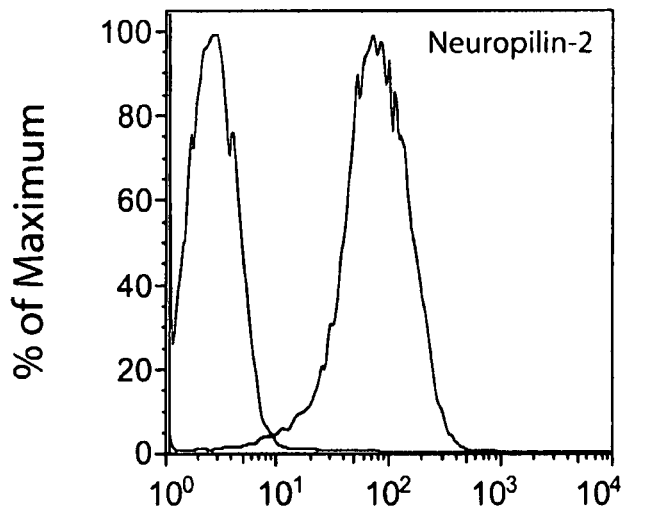

One major approach to inhibiting metastasis has been via inhibition of the VEGFC axis (Chen et al., *Cancer Res* 65, 9004-9011 (2005); He et al., *J Natl Cancer Inst* 94, 819-825 (2002); Krishnan et al., *Cancer Res* 63, 713-722 (2003); Lin et al., *Cancer Res* 65, 6901-6909 (2005)). To determine if blocking Nrp2 function could also modulate the development of metastasis, the effects of Anti-Nrp2$^B$ treatment on the formation of lung metastasis were tested in two different tumor models—the 66c14, breast cancer model, and the C6 glioblastoma model. 66c14 is a murine mammary adenocarcinoma line derived from a spontaneous mammary tumor in a Balb/c mouse (Aslakson and Miller, *Cancer Res* 52, 1399-1405 (1992)). These cells express VEGFC and metastasize via the lymphatic system to the lungs (Aslakson and Miller, 1992, supra). Orthotopic transplantation of these cells in Balb/c mice resulted in reproducible development of tumors and lung metastasis. Anti-Nrp2$^B$ treatment did not affect the primary growth rate of the tumors (FIG. 5A). As VEGFR3 ECD did dramatically reduce primary tumor growth rates it was excluded from any further analysis of metastasis. A cohort of animals (N=6 from each group) with similar sized tumors from both treatment arms were sacrificed concurrently, and the lungs were dissected out and inflated to facilitate analysis for metastatic nodules. Anti-Nrp2$^B$ caused a dramatic reduction in the average number of visually detected metastatic nodules per lung when compared to control IgG treated animals (FIGS. 5B, C), from an average of 3.5 to 0.8 (P=0.03). In order to confirm this result and extend our evaluation to metastasis within the lung parenchyma that were not amenable to visual examination, we performed a micro-CT analysis (Li et al., *Technol Cancer Res Treat* 5, 147-155 (2006)) of the lungs after necropsy. This analysis confirmed that Anti-Nrp2$^B$ treated animals had a reduction in the number of lung metastasis when compared to control treated animals (FIG. 5D-F). However, micro-CT analysis was more sensitive than visual analysis resulting in a larger absolute number of metastatic nodules in both groups. Micro-CT also allowed us to determine the total metastatic burden within the lung. Anti-Nrp2$^B$ treatment also resulted in a reduction of total metastatic volume (0.74 cm$^3$) in comparison to control treatment (1.78 cm$^3$). Additionally, this analysis verified that the vast majority of lesions were on the surface of lungs in both control and Anti-Nrp2$^B$ treated animals. Therefore, Anti-Nrp2$^B$ did not cause a reduction in metastasis by shifting the nodules from the surface to the lung parenchyma.

FACS analysis, performed as described in Example 4, indicated that Nrp2, but not VEGFR2 or VEGFR3 was expressed on 66c14 tumor cells. This raised the possibility that treatment with Anti-Nrp2$^B$ was affecting tumor cell behavior directly to impact metastasis. This was unlikely given the lack of effect on primary tumor growth with Anti-Nrp2$^B$ treatment. Additionally, Anti-Nrp2$^B$ did not have any effect on tumor cell proliferation, apoptosis or migration in vitro. However, to address the possibility that the reduction in metastasis was due to effects of Anti-Nrp2$^B$ on tumor cells, we also evaluated the effect of Anti-Nrp2$^B$ on the C6 rat glioblastoma model. These cells do not express Nrp2 on their surface to an appreciable degree (FIG. 6E), express VEGFC and are thought to metastasize to the lung via the lymphatic system (Bernstein and Woodard, 1995). Additionally, they have been engineered to express bgalactosidase, which can be used as a marker to facilitate detection of tumor cells.

Figure 5H:
Figure 6A:
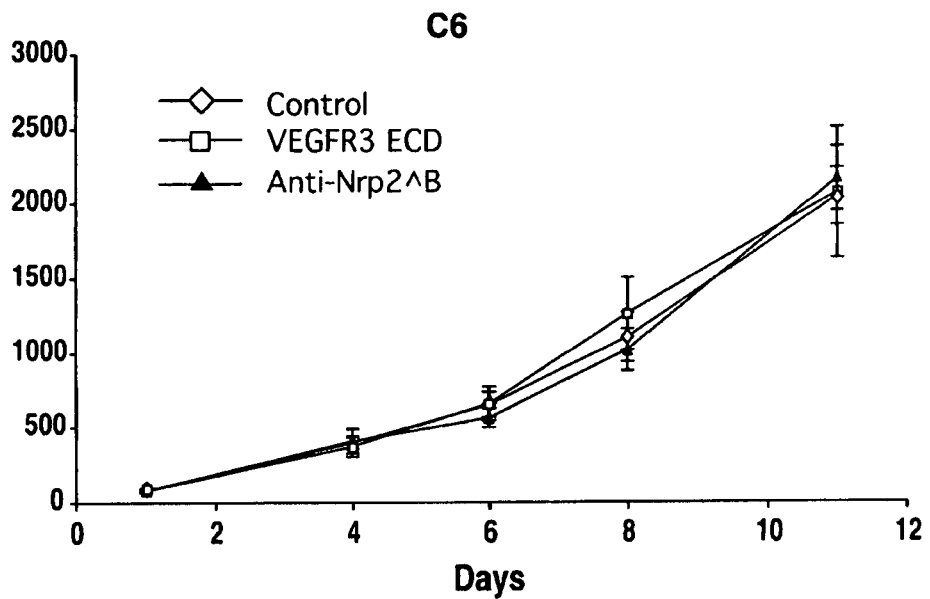
FIG. 6. Anti-Nrp2$^B$ treatment results in a reduction of lung metastasis in the C6 tumor model. (A) Mean tumor volume graph of C6 tumor model study analyzed below. Animals were dosed twice weekly i.p. with Anti-Nrp2$^B$(10 mg/kg), VEGFR3 ECD (25 mg/kg) or control antibody (10 mg/kg) once tumors reached an average size of 100 mm$^3$ and were dosed throughout the study. (B) Quantification by visual inspection of the number of metastatic nodules per lung in control, VEGFR3 ECD and Anti-Nrp2$^B$ treated animals. (C) Representative images of lungs from control (left), VEGFR3 ECD (middle) and Anti-Nrp2$^3$ (right) treated animals. Lungs were inflated prior to fixation by right cardiac ventricular perfusion. Nodules are highlighted in white to facilitate visualization. (D) 3-dimendional renderings of representative micro-CT scanned lungs demonstrating metastatic nodules (red) in control (left) and Anti-Nrp2$^B$ (right) treated animals. The positions of the longitudinal section (top inset) and the cross section (bottom insert) are indicated by the black and red dotted lines respectively. This analysis confirms that most nodules are on the surface of lungs. (E) FACS analysis of Nrp2 levels on the surface of in vitro cultured 66c14 tumor cells. (F) H&E staining of a lung nodule demonstrating metastatic tumor cells. Error bars represent standard error of the mean. Scale bar * for C and  for F.
Figure 6B:
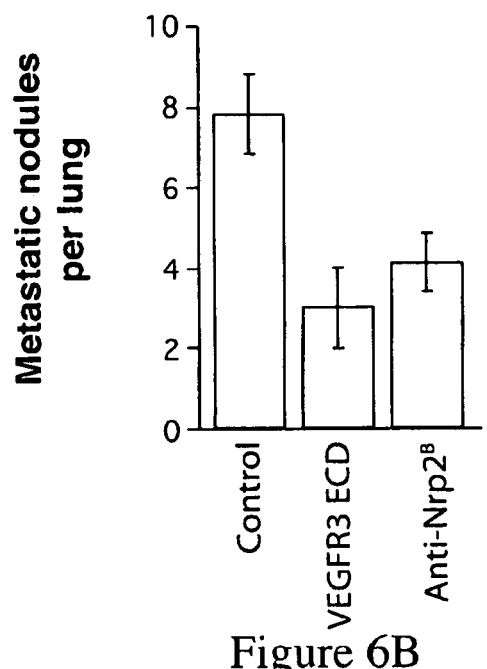
Figure 6C:
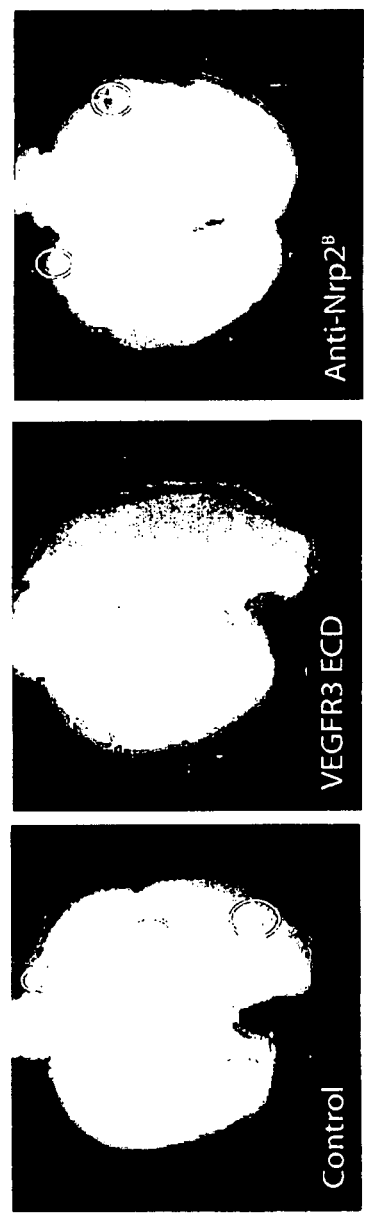
Figure 6D:
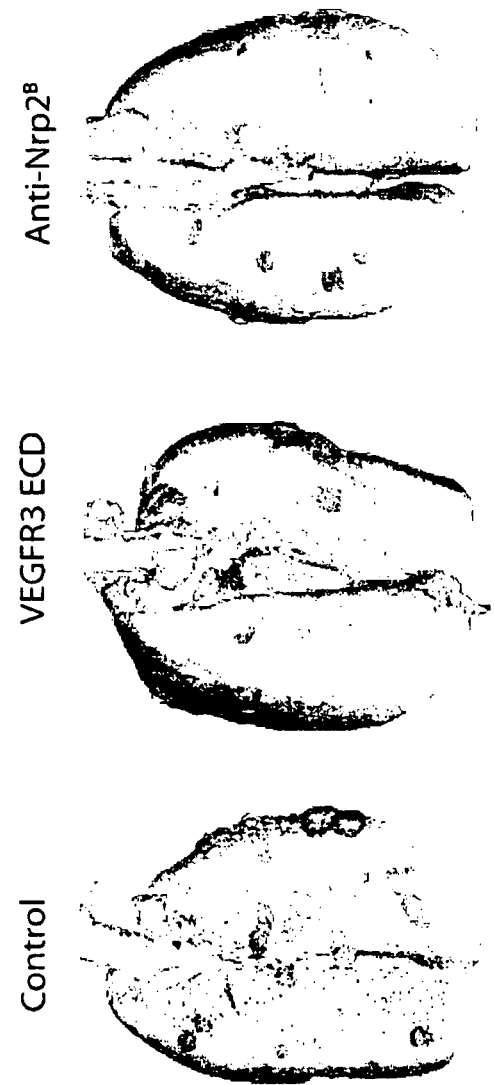
Figure 6E:
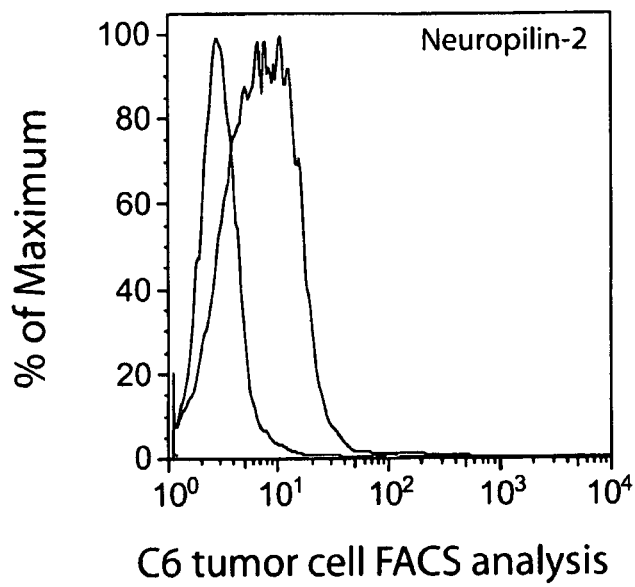
Figure 6F:

Subcutaneous transplantation of these cells in nude mice resulted in consistent development of tumors and lung metastasis. Anti-Nrp2$^B$ treatment did not affect the primary growth rate of these tumors (FIG. 6A). Additionally, VEGFR3 ECD did not dramatically reduce primary tumor growth rate in this tumor model. This allowed for comparisons of the anti-metastatic effects of VEGFR3 ECD and Anti-Nrp2. Again, a cohort of animals (N=10) with similar sized tumors from all treatment arms were sacrificed and the lungs were dissected out and inflated to facilitate analysis for metastatic nodules. Treatment with both, Anti-Nrp2$^B$ and VEGFR3 ECD, caused a reduction in the average number of visually detected metastatic nodules per lung (FIGS. 6B, C). The reduction noted with Anti-Nrp2$^B$ was comparable to that seen with VEGFR3 ECD. Micro-CT analysis of the lungs confirmed these findings (FIG. 6D) and verified that the vast majority of metastasis were localized to the surface of the lungs in all treatment arms. Nodules were confirmed to be metastatic lesions by histology in both tumor models (FIGS. 5H and 6G). Additionally, general necropsy did not reveal nodules on the surface of other organs in either tumor model.

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims.

All references cited throughout the specification, and the references cited therein, are hereby expressly incorporated by reference in their entirety.

What is claimed:

1. An anti-neuropilin2B (anti-Nrp2B) antibody, or an antigen-binding fragment thereof, wherein the antibody or antigen-binding fragment:
   i) comprises complementarity determining region light chain (CDRL)1, CDRL2, and CDRL3 sequences and complementarity determining region heavy chain (CDRH)1, CDRH2, CDRH3 sequences of an antibody selected from the group consisting of YW68.4.2 and YW68.4.2.36;
   ii) is a variant of the antibody of (i) having one to five alterations in the framework regions, wherein the light chain framework regions comprise residues 1-23, 35-49, 57-88 and 98-107 or 1-25, 33-49, 53-90 and 97-107 and the heavy chain framework regions comprise residues 1-30, 36-49, 66-94 and 103-113 or 1-25, 33-52, 56-95 and 102-113; or
   iii) is an affinity matured variant of the antibody of (i).

2. An anti-Nrp2A antibody comprising the heavy and light chain variable region sequences of YW126.20, or an antigen-binding fragment or variant thereof, wherein the variant has one to five alterations in the framework regions or is an affinity matured variant.

3. A pharmaceutical composition for the treatment of tumor metastasis comprising an effective amount of an anti-Nrp2B antibody, wherein the antibody comprises complementarity determining region light chain (CDRL)1, CDRL2, and CDRL3 sequences and complementarity determining region heavy chain (CDRH)1, CDRH2, CDRH3 sequences of an antibody selected from the group consisting of YW68.4.2 and YW68.4.2.36, in admixture with a pharmaceutically acceptable carrier.

4. An anti-Nrp2B antibody for use in the treatment of tumor metastasis, wherein the antibody comprises complementarity determining region light chain (CDRL)1, CDRL2, and CDRL3 sequences and complementarity determining region heavy chain (CDRH)1, CDRH2, CDRH3 sequences of an antibody selected from the group consisting of YW68.4.2 and YW68.4.2.36.

5. An anti-Nrp2B antibody, or an antigen-binding fragment thereof, wherein the antibody or antigen-binding fragment:
   i) comprises the heavy and light chain variable region sequence of an antibody selected from the group consisting of YW68.4.2 and YW68.4.2.36;
   ii) is a variant of the antibody of (i) having one to five alterations in the framework regions, wherein the light chain framework regions comprise residues 1-23, 35-49, 57-88 and 98-107 or 1-25, 33-49, 53-90 and 97-107 and the heavy chain framework regions comprise residues 1-30, 36-49, 66-94 and 103-113 or 1-25, 33-52, 56-95 and 102-113; or
   iii) is an affinity matured variant of the antibody of (i).

6. An anti-Nrp2B antibody which is YW68.4.2.36 (SEQ ID NO: 1), or an antigen-binding fragment thereof.

7. The anti-Nrp2B antibody of claim 5 wherein said variant is an affinity matured variant.

8. The anti-Nrp2B antibody of claim 5 selected from the group consisting of YW68.4.2 and YW68.4.2.36 and antigen-binding fragments thereof.

9. The anti-Nrp2A antibody of claim 2 wherein said variant is an affinity matured variant.

10. The anti-Nrp2A antibody of claim 2 which is YW126.20 or an antigen-binding fragment thereof.

11. A composition comprising an antibody, antigen-binding fragment, or variant of any one of claims 1, 5, and 6, in admixture with a pharmaceutically acceptable carrier.

12. The pharmaceutical composition of claim 3 wherein said anti-Nrp2B antibody is selected from the group consisting of YW68.4.2, YW68.4.2.36, and antigen-binding fragments and variants thereof, wherein the variants have one to five alterations in the framework regions or are affinity matured variants.

13. The anti-Nrp2B antibody or antigen-binding fragment of claim 5 which comprises the sequence of YW68.4.2 (SEQ ID NO: 1) or the sequence of YW68.4.2.36 (SEQ ID NO: 2).

14. The anti-Nrp2B antibody of claim 13 which comprises the sequence of YW68.4.2.36 (SEQ ID NO: 1), or an antigen-binding fragment thereof.

15. The anti-Nrp2B antibody of any one of claims 1, 5, and 6, wherein said antibody, antigen-binding fragment or variant, is chimeric or humanized.

16. The anti-Nrp2B antibody, or antigen-binding fragment or variant, of any one of claims 1, 5, and 6, wherein said fragment is selected from the group consisting of Fab, F(ab')$_2$, and scFv fragments.

17. The anti-Nrp2B antibody, or antigen-binding fragment or variant, of any one of claims 1-2 and 5-6 which is bispecific.

18. The anti-Nrp2B antibody, or antigen-binding fragment or variant, of claim 17 which additionally binds to VEGF.

19. The anti-Nrp2A antibody, or antigen-binding fragment or variant, of any one of claims 2-10 which is bispecific.

20. The anti-Nrp2A antibody, or antigen-binding fragment or variant, of claim 19 which additionally binds to VEGF.

* * * * *